United States Patent
Krajmalnik-Brown et al.

(10) Patent No.: US 12,084,727 B2
(45) Date of Patent: *Sep. 10, 2024

(54) MICROBIOME MARKERS AND THERAPIES FOR AUTISM SPECTRUM DISORDERS

(71) Applicant: Arizona Board of Regents on Behalf of Arizona State University, Tempe, AZ (US)

(72) Inventors: Rosa Krajmalnik-Brown, Chandler, AZ (US); Dae-Wook Kang, Phoenix, AZ (US); Jin Gyoon Park, Phoenix, AZ (US); Joshua Labaer, Chandler, AZ (US); Zehra Ilhan, Tempe, AZ (US)

(73) Assignee: Arizona Board of Regents on Behalf of Arizona State University, Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/147,224

(22) Filed: Dec. 28, 2022

(65) Prior Publication Data

US 2023/0220494 A1    Jul. 13, 2023

Related U.S. Application Data

(60) Continuation of application No. 16/118,061, filed on Aug. 30, 2018, now Pat. No. 11,542,560, which is a continuation of application No. 15/629,962, filed on Jun. 22, 2017, now abandoned, which is a division of application No. 14/403,425, filed as application No. PCT/US2013/032668 on Mar. 15, 2013, now Pat. No. 9,719,144.

(60) Provisional application No. 61/651,846, filed on May 25, 2012.

(51) Int. Cl.
| | |
|---|---|
| *C12Q 1/689* | (2018.01) |
| *A61K 31/437* | (2006.01) |
| *A61K 35/741* | (2015.01) |
| *C12Q 1/6883* | (2018.01) |
| *G01N 33/68* | (2006.01) |

(52) U.S. Cl.
CPC ............ *C12Q 1/689* (2013.01); *A61K 31/437* (2013.01); *A61K 35/741* (2013.01); *C12Q 1/6883* (2013.01); *G01N 33/6896* (2013.01); *C12Q 2600/142* (2013.01); *C12Q 2600/158* (2013.01)

(58) Field of Classification Search
None
See application file for complete search history.

(56) References Cited

U.S. PATENT DOCUMENTS

| | | |
|---|---|---|
| 3,192,116 A | 6/1965 | Möse et al. |
| 3,713,836 A | 1/1973 | Carlsson |
| 4,098,728 A | 7/1978 | Rosenblatt |
| 4,332,790 A | 6/1982 | Sozzi et al. |
| 4,335,107 A | 6/1982 | Snoeyenbos |
| 4,394,377 A | 7/1983 | Spires |
| 4,452,779 A | 6/1984 | Cockerill |
| 4,536,409 A | 8/1985 | Farrell et al. |
| 4,657,762 A | 4/1987 | Mikkola et al. |
| 4,710,379 A | 12/1987 | Kawai et al. |
| 4,892,731 A | 1/1990 | Arai |
| 4,975,286 A | 12/1990 | Hechter |
| 5,213,807 A | 5/1993 | Chemburkar |
| 5,266,315 A | 11/1993 | Taguchi et al. |
| 5,443,826 A | 8/1995 | Borody |
| 5,599,795 A | 2/1997 | McCann |
| 5,728,380 A | 3/1998 | Allen et al. |
| 5,800,821 A | 9/1998 | Acheson et al. |
| 5,837,238 A | 11/1998 | Casas et al. |
| 5,858,356 A | 1/1999 | Wolf et al. |

(Continued)

FOREIGN PATENT DOCUMENTS

| | | |
|---|---|---|
| CA | 2391422 A1 | 1/2004 |
| CN | 201441672 U | 4/2010 |

(Continued)

OTHER PUBLICATIONS

Gerding, "Management of Clostridium difficile infection: thinking inside and outside the box," Clin Infect Dis., 51 (11):1306-13 (2010).

(Continued)

*Primary Examiner* — Vera Afremova
(74) *Attorney, Agent, or Firm* — POLSINELLI PC

(57) ABSTRACT

The present disclosure provides for characterization of normal flora and identifying biomarkers in the gut of healthy, neurotypical subjects. Aspect of the disclosure provide for the characterization of the gut microbiome in ADS subjects, characterized by reduced richness and significant loss of the '*Prevotella*-like enterotype' compared to neurotypical subjects. The relative abundance of genera *Prevotella, Coprococcus, Prevotellaceae* and *Veillonellaceae* are significantly lower in autistic children than in neurotypical children. Further, *Prevotella*, is one of the three main classifiers for the human enterotypes, along with Bacteroides and *Ruminococcus*. These three core genera are among main contributors in the principle component analysis. '*Prevotella*-like enterotype' was absent in the autistic group, while neurotypical samples showed an even distribution among the three enterotypes. The present disclosure provides for an understanding the association between gut microbiota, health, and disease states, and provides for potential diagnostic and therapeutic targets.

9 Claims, 12 Drawing Sheets

Specification includes a Sequence Listing.

(56) References Cited

U.S. PATENT DOCUMENTS

| | | |
|---|---|---|
| 5,902,578 A | 5/1999 | Halpin-Dohnalek et al. |
| 5,902,743 A | 5/1999 | Luchansky et al. |
| 6,087,386 A | 7/2000 | Chen et al. |
| 6,162,464 A | 12/2000 | Jacob et al. |
| 6,245,740 B1 | 6/2001 | Goldenberg et al. |
| 6,284,274 B1 | 9/2001 | Merrill et al. |
| 6,428,783 B1 | 8/2002 | Khachatrian et al. |
| 6,514,531 B1 | 2/2003 | Alaux et al. |
| 6,649,397 B1 | 11/2003 | Nakamura |
| 6,756,032 B1 | 6/2004 | Tepper et al. |
| 6,926,907 B2 | 8/2005 | Plachetka |
| 6,984,513 B2 | 1/2006 | Brown et al. |
| 7,018,629 B2 | 3/2006 | Jacob et al. |
| 7,374,753 B1 | 5/2008 | Farmer et al. |
| 7,541,091 B2 | 6/2009 | Sisson et al. |
| 7,749,509 B2 | 7/2010 | Cobb et al. |
| 7,763,276 B1 | 7/2010 | Shodai et al. |
| 7,799,341 B2 | 9/2010 | Porzio et al. |
| 7,815,956 B2 | 10/2010 | Lee et al. |
| 7,846,475 B2 | 12/2010 | Shiraishi et al. |
| 7,888,062 B1 | 2/2011 | Garner et al. |
| 7,998,510 B2 | 8/2011 | Caswell |
| 8,168,171 B2 | 5/2012 | Mogna et al. |
| 8,637,297 B2 | 1/2014 | Vieites Fernandez et al. |
| 8,658,153 B2 | 2/2014 | Daube et al. |
| 8,771,673 B2 | 7/2014 | Cobb et al. |
| 9,707,207 B2 * | 7/2017 | Finegold ............... A61K 35/745 |
| 9,719,144 B2 * | 8/2017 | Krajmalnik-Brown ...................... G01N 33/6896 |
| 9,848,760 B2 * | 12/2017 | Bangera ................. G16H 10/40 |
| 11,542,560 B2 * | 1/2023 | Krajmalnik-Brown ...................... A61K 31/437 |
| 2001/0014322 A1 | 8/2001 | Chen |
| 2002/0013270 A1 | 1/2002 | Bolte |
| 2002/0022019 A1 | 2/2002 | Laulund |
| 2002/0039599 A1 | 4/2002 | Lin |
| 2003/0092163 A1 | 5/2003 | Collins |
| 2003/0092724 A1 | 5/2003 | Kao |
| 2003/0147858 A1 | 8/2003 | Renaud |
| 2004/0062757 A1 | 4/2004 | Finegold |
| 2004/0170617 A1 | 9/2004 | Finegold |
| 2004/0223956 A1 | 11/2004 | Naidu et al. |
| 2006/0076536 A1 | 4/2006 | Barshied |
| 2006/0099197 A1 | 5/2006 | Farmer |
| 2006/0115465 A1 | 6/2006 | Macfarlane |
| 2006/0275223 A1 | 12/2006 | Burr |
| 2007/0059296 A1 | 3/2007 | Chen |
| 2008/0299197 A1 | 12/2008 | Toneguzzo et al. |
| 2010/0178349 A1 | 7/2010 | Kolter et al. |
| 2010/0178413 A1 | 7/2010 | Gorris |
| 2010/0184785 A1 | 7/2010 | Kolter et al. |
| 2010/0222311 A1 | 9/2010 | Thommes et al. |
| 2010/0226866 A1 | 9/2010 | Yamashiro et al. |
| 2010/0233278 A1 | 9/2010 | Ookawa |
| 2010/0239667 A1 | 9/2010 | Hemmingsen et al. |
| 2010/0247665 A1 | 9/2010 | Takahashi |
| 2010/0255231 A1 | 10/2010 | Chau et al. |
| 2010/0255307 A1 | 10/2010 | Gonze et al. |
| 2010/0278930 A1 | 11/2010 | Okumura et al. |
| 2010/0285164 A1 | 11/2010 | Schaible et al. |
| 2010/0297031 A1 | 11/2010 | beda Perez et al. |
| 2011/0008554 A1 | 1/2011 | Chen et al. |
| 2011/0045222 A1 | 2/2011 | Peters |
| 2011/0081320 A1 | 4/2011 | Westall et al. |
| 2011/0091431 A1 | 4/2011 | Olmstead |
| 2011/0200570 A1 | 8/2011 | Mosbaugh et al. |
| 2011/0218216 A1 | 9/2011 | Vivek |
| 2012/0039853 A1 | 2/2012 | Corveleyn et al. |
| 2012/0064133 A1 | 3/2012 | Chauhan |
| 2012/0087895 A1 | 4/2012 | Mazmanian |
| 2012/0129773 A1 | 5/2012 | Geier |
| 2012/0183612 A1 | 7/2012 | Brogmann et al. |
| 2012/0252775 A1 | 10/2012 | Finegold |
| 2013/0022622 A1 | 1/2013 | Ben-Ari |
| 2013/0266539 A1 * | 10/2013 | Borody ................. A61K 9/19 424/93.3 |
| 2013/0316394 A1 | 11/2013 | Stimpson |
| 2014/0065132 A1 | 3/2014 | Hsiao et al. |
| 2014/0147425 A1 | 5/2014 | Henn et al. |
| 2014/0255351 A1 | 9/2014 | Berstad et al. |
| 2014/0328803 A1 | 11/2014 | McKenzie et al. |
| 2014/0341921 A1 | 11/2014 | Honda et al. |
| 2015/0050246 A1 | 2/2015 | Jones et al. |
| 2015/0224152 A1 | 8/2015 | Littman |
| 2015/0238544 A1 | 8/2015 | Jones et al. |
| 2015/0374761 A1 | 12/2015 | Sadowsky et al. |
| 2016/0089363 A1 | 3/2016 | Borody |

FOREIGN PATENT DOCUMENTS

| | | |
|---|---|---|
| DE | 2134179 A1 | 1/1973 |
| EP | 0303426 A2 | 2/1989 |
| EP | 0456418 A2 | 11/1991 |
| EP | 1514572 A2 | 3/2005 |
| EP | 1800688 A1 | 6/2007 |
| FR | 1275 M | 5/1962 |
| FR | 2427 M | 3/1964 |
| FR | 2828 M | 11/1964 |
| FR | 5528 M | 11/1967 |
| FR | 2244464 A2 | 4/1975 |
| GB | 1271674 A | 4/1972 |
| JP | H05306221 A | 11/1993 |
| JP | H07242539 A | 9/1995 |
| JP | H07242557 A | 9/1995 |
| JP | 2008106066 A | 5/2008 |
| WO | 1990001335 A1 | 2/1990 |
| WO | 1995033046 A1 | 12/1995 |
| WO | 1996011014 A1 | 4/1996 |
| WO | 1998013068 A1 | 4/1998 |
| WO | 2000007571 A2 | 2/2000 |
| WO | 2000015760 A1 | 3/2000 |
| WO | 2000042168 A2 | 7/2000 |
| WO | 2002007741 A1 | 1/2002 |
| WO | 2003033681 A1 | 4/2003 |
| WO | 2005017095 A2 | 2/2005 |
| WO | 2006127355 A2 | 11/2006 |
| WO | 2008077614 A2 | 7/2008 |
| WO | 2008105715 A1 | 9/2008 |
| WO | 2008117266 A2 | 10/2008 |
| WO | 2008117267 A2 | 10/2008 |
| WO | 2009026306 A2 | 2/2009 |
| WO | 2009055362 A1 | 4/2009 |
| WO | 2010040020 A1 | 4/2010 |
| WO | 2011033310 A1 | 3/2011 |
| WO | 2011094027 A1 | 8/2011 |
| WO | 2011110347 A2 | 9/2011 |
| WO | 2011151941 A1 | 12/2011 |
| WO | 2012016287 A2 | 2/2012 |
| WO | 2012045150 A1 | 4/2012 |
| WO | 2012122478 A1 | 9/2012 |
| WO | 2013037067 A1 | 3/2013 |
| WO | 2013090825 A1 | 6/2013 |
| WO | 2013176774 A1 | 11/2013 |
| WO | 2014078911 A1 | 5/2014 |
| WO | 2014152338 A1 | 9/2014 |
| WO | 2014152484 A1 | 9/2014 |
| WO | 2015006355 A2 | 1/2015 |
| WO | 2015051323 A1 | 4/2015 |
| WO | 2015077794 A1 | 5/2015 |
| WO | 2015095241 A2 | 6/2015 |
| WO | 2016191356 A1 | 12/2016 |
| WO | 2017218681 A1 | 12/2017 |
| WO | 2018089794 A1 | 5/2018 |

OTHER PUBLICATIONS

Geuking et al., "Intestinal Bacterial Colonization Induces Mutualistic Regulatory T Cell Respones," Immunity, 34:794-806 (2011).

Gilbert J et al. (2013). "Towards effective probiotics for autism and other neurodevelopmental disorders," Cell, 155: 1446-1448.

Gill et al.; "Metagenomic Analysis of the Human Distal Gut Microbiome"; Science, 2006, vol. 312, pp. 1355-1359.

(56) References Cited

OTHER PUBLICATIONS

Gitlin et al., "*Mycobacterium avium* ss paratuberculosis-associated Diseases: Piecing the Crohn's Puzzle Together," J Clin Gastroenterol, 46(8):649-655 (2012).
Goehler et al.; "Campylobacter jejuni infection increases anxiety-like behavior in the holeboard: possible anatomical substrates for viscerosensory modulation of exploratory behavior"; Brain Behavior Immunology, 2008, vol. 22, No. 3, pp. 354-366.
Gondalia et al.; "Faecal microbiota of individuals with autism spectrum disorder"; Electronic Journal of Applied Psychology, vol. 6, No. 2, pp. 24-29 (2010).
Gough et al., "Systematic review of intestinal microbiota transplantation (fecal bacteriotherapy) for recurrent Clostridium difficile infection," Clin. Infect. Dis., 53(10):994-1002 (2011).
Gregersen et al., "Duodenal administered seal oil for patients with subjective food hypersensitivity: an explorative open pilot study," International Journal of General Medicine, 2010(3):383-92 (2010).
Grehan et al., "Durable alteration of the colonic microbiota by the administration of donor fecal flora," Journal of Clinical Gastroenterology, 44(8):551-561 (2010).
Guarner et al., "Gut flora in health and disease," Lancet, 361(9356):512-519 (2003).
Gustafsson et al., "Faecal Short-Chain Fatty Acids in Patients with Antibiotic-Associated Diarrhoea, before and after Faecal Enema Treatment," Scand J Gastroenterol, 33:721-727 (1998).
Gustafsson et al., "The Effect of Faecal Enema on Five Microflora-Associated Characteristics in Patients with Antibiotic-Associated Diarrhoea," Scandinavian Journal of Gastroenterology, 34:580-586 (1999).
Hamilton et al., "Change in microbial community composition of in patients with recalcitrant Clostridium difficile colitis treated with fecal bacteriotherapy," International Human Microbiome Congress, Poster and Presentation, Vancouver, ON, Canada, Mar. 9-11, 2011.
Hamilton et al., "High-throughput DNA sequence analysis reveals stable engraftment of gut microbiota following transplantation of gut microbiota following transplantation of previously frozen fecal bacteria," Gut Microbes, 4(2):1-11 (2013).
Hamilton et al., "Standardized Frozen Preparation for Transplantation of Fecal Microbiota for Recurrent Clostridium difficile Infection," Article and Supplementary Material, Am. J. Gastroenterol., 107(5):761-767 (2012).
Hanley et al.; "The Meaning and Use of the Area under a Receiver Operating Characteristic (ROG) Curve"; Radiology, Apr. 1982, vol. 143, pp. 29-36.
Hayashi et al., "Phylogenetic Analysis of the Human Gut Microbiota Using 16S rDNA Clone Libraries and Strictly Anaerobic Culture-Based Methods," Microbiol. Immunol., 46(8):535-548 (2002).
Hayashi et al.; "*Prevotella copri* sp. nov. and *Prevotella stercorea* sp. nov., isolated from human faeces"; 57 International Journal of Systematic and Evolutionary Microbiology, 2007; pp. 947-946.
Hecker et al., "Fecal Microbiota Transplantation by Freeze-Dried Oral Capsules for Recurrent Clostridium difficile Infection," Open Forum Infect Dis, 3(2): 1-2 (2016).
Hellemans et al., "Fecal transplantation for recurrent Clostridium difficile colitis, an underused treatment modality," Acta Gastroenterol Belg., 72(2):269-70 (2009).
Henriksson et al., "Probiotics under the regulatory microscope," Expert Opin. Drug Saf., 4(6):1-9 (2005).
Hensel et al., "Vagal Ascent and Distribution of 125 I-Tetanus Toxin after Injection into the Anterior Wall of the Stomach," Naunyn-Schmiedeberg's Arch. Pharmacol, 276:395-402 (1973).
Hollister E et al. (2014). "Compositional and Functional Features of the Gastrointestinal Microbiome and Their Effects on Human Health," Gastroenterology, 146(6): 1449-1458.
Holmes E et al. (2012). "Therapeutic Modulation of Microbiota-Host Metabolic Interactions," Science Translational Medicine, 4(137): 137rv6.
Holst et al.; "Biochemistry and cell biology of bacterial endotoxins"; FEMS Immunology and Medical Microbiology, 1996, vol. 16, pp. 83-104.
Honda et al., "Regulation of T Cell Responses by Intestinal Commensal Bacteria," Journal of Intestinal Microbiology, vol. 25, 2nd Edition:104 (2011).
Hooper et al., "How host-microbial interactions shape the nutrient environment of the mammalian intestine," Annu. Rev. Nutr., 22:283-307 (2002).
Hope et al., "Sporadic colorectal cancer-role of the commensal microbiota," FEMS Microbiol. Lett., 244:1-7 (2005).
Horvath et al.; "Gastrointestinal abnormalities in children with autistic disorder"; Journal of Pediatrics, 1999, vol. 135, No. 5, pp. 559-563.
Hota et al., "Determining Mortality Rates Attributable to Clostridium difficile Infection," Emerg. Infect. Dis., 18 (2):305-307 (2012).
Hota et al., "Oral Vancomycin Followed by Fecal Transplant Versus Tapering Oral Vancomycin," U.S. National Institutes of Health, Clinical Study No. NCT01226992, Oct. 20, 2010, last updated Jan. 14, 2013, Web, May 20, 2014, pp. 1-4 <http://clinicaltrials.gov/ct2/show/NCT01226992>.
Hsiao E et al. (2013). "Microbiota Modulate Behavioral and Physiological Abnormalities Associated with Neurodevelopmental Disorders," Cell 155: 1451-1463.
Hu et al., "Prospective derivation and validation of a clinical prediction rule for recurrent Clostridium difficile infection," Gastroenterology, 136:1206-1214 (2009).
Huang et al., "Once-daily propranolol extended-release tablet dosage form: formulation design and in vitro/in vivo investigation," European J. of Pharm. & Biopharm., 58:607-614 (2004).
Huttenhower et al., "Structure, function and diversity of the healthy human microbiome," The Human Microbiome Project Consortium, Nature, 486:207-214 (2012).
Huws et al.; "As yet uncultured bacteria phylogenetically classified as Prevotella, Lachnospiraceae incertae sedis and unclassifed Bacteriodales, Clostridiales and Ruminococcaceae may play a predominant role in ruminal biohydrogenationemion"; Environmental Microbiology, 2011, vol. 13, No. 6, pp. 1500-1512.
Immunology in the 21st Century: Defeating Infection, Autoimmunity, Allergy, and Cancer, ICI 2010 Wrap-up Report, 14th International Congress of Immunology, pp. 1 (2010).
Inflammatory Bowel Disease Facts, Disease Prevention and Treatment Strategies, Crohn's Disease and Inflammatory Bowel Disease (IBD), HealingWithNutrition.com, pp. 1-4, n.d., Web, Oct. 23, 2005 <http://www.HealingWithNutrition.com/disease/inflambowels/chrohns.html>.
International Preliminary Examination Report completed Nov. 19, 2002, in International Application No. PCT/AU2001/000907, 19 pgs.
International Preliminary Report on Patentability completed Dec. 12, 2012, in International No. PCT/AU2011/000987, 35 pgs.
International Preliminary Report on Patentability completed Mar. 12, 2015, in International Application No. PCT/AU2013/001362, 29 pgs.
International Preliminary Report on Patentability dated Sep. 10, 2013, in International Application No. PCT/US2012/028484, 10 pgs.
International Search Report and Written Opinion dated Aug. 22, 2016 in International Application No. PCT/US2016/033747.
International Search Report and Written Opinion dated Aug. 8, 2016, in International Application No. PCT/US2016/032695, 10 pgs.
International Search Report and Written Opinion dated Feb. 5, 2014, in International Application No. PCT/AU2013/001362, 17 pgs.
International Search Report and Written Opinion dated Jul. 31, 2014, in International Application No. PCT/US2014/027391, 16 pgs.
International Search Report and Written Opinion dated Oct. 28, 2011, in International No. PCT/AU2011/000987, 18 pgs.
International Search Report and Written Opinion of International Searching Authority for PCT/US2013/032668, dated Jul. 5, 2013 (11 pages).
International Search Report dated Aug. 10, 2012, in International Application No. PCT/US2012/028484, 7 pgs.

(56) References Cited

OTHER PUBLICATIONS

Collins et al., "The Phylogeny of the Genus Clostridium: Proposal of Five New Genera and Eleven New Species Combinations," International Journal of Systematic Bacteriology, pp. 812-826 (1994).
Collins et al.; "The Relationship Between Intestinal Microbiota and the Central Nervous System in Normal Gastrointestinal Function and Disease"; Gastroenterology, 2003 (2009), 136, pp. 2003-2014.
Colman R et al. (2014). "Fecal microbiota transplantation as therapy for inflammatory bowel disease: A systematic review and meta-analysis," Journal of Crohn's and Colitis, 8(12): 1569-1581.
Constantino et al., "Validation of Brief Quantitative Measure of Autistic Traits: Comparison of the Social Responsiveness Scale with the Autism Diagnostic Interview-Revised," Journal of Autism and Developmental Disorders, 33(4): 427-433 (2003).
Critchfield J et al. (2011). "The Potential Role of Probiotics in the Management of Childhood Autism Spectrum Disorders," Gastroenterology Research and Practice, 1(1): 1-8.
Crohn's Disease, Prevention, Health Guide A-Z, WebMDHealth, pp. 1-2, n.d., Web, Oct. 23, 2005 <http://mywebmd.com/hw/inflammatory.sub.--bowel/uf6012.asp>.
Crowther, "Transport and Storage of Faeces for Bacteriological Examination," Journal of Applied Bacteriology, 34 (2):477-483 (1971).
Cutolo et al., "Fecal feedings as a therapy in *Staphylococcus enterocolitis*," NY State J Med, 59:3831-3833 (1959).
Dale et al., "Molecular interactions between bacterial symbionts and their hosts," Cell, 126(3):453-465 (2006).
Damman C (2012). "The microbiome and inflammatory bowel disease: is there a therapeutic role for fecal microbiota transplantation?" The American Journal of Gastroenterology 107(10): 1452.
Dan et al., "Comparison of preservation media and freezing conditions for storage of specimens of faeces," J. Med Microbiology, 28:151-154 (1989).
Darrien et al.; "*Akkermansia muciniphila* gen. nov., sp. nov., a human intestinal mucin-degrading bacterium"; International Journal of Systematic and Evolutionary Microbiology; 2004; vol. 54, pp. 1469-1476.
De Angelis, M, et al., (2013). "Fecal Mircrobiota and Metabolome of Children with Autism and Pervasive Development Disorder Not Otherwise Specified," PLOS One. 8(10); e76993.
De Giulio et al., "Use of Algiinate and Cryo-Protective Sugars to Improve the Viability of Lactic Acid Bacteria After Freezing and Freeze-Drying," World Journal of Microbiology & Biotechnology, 21:739-746 (2005).
Defang et al., "In vitro and in vivo evaluation of two extended release preparations of combination metformin and glipizide," Drug Develop. & Indust. Pharm., 31:677-685 (2005).
Dendukuri et al., "Probiotic therapy for the prevention and treatment of Clostridium difficile-associated diarrhea: a systematic review," CMAJ, 173(2):167-170 (2005).
Derwent Abstract Accession No. 98-230427/20, WO 98/13068 A, (Kuperman VB) Apr. 2, 1998.
Dethlefsen et al., "An ecological and evolutionary perspective on human-microbe mutualism and disease," Nature, 449 (7164):811-818 (2007).
Deufemia et al.; "Abnormal intestinal permeability in children with autism"; Acta Pediatric, 1996, vol. 85, p. 1076.
Dewhirst et al., "Phylogeny of the Defind Murine Microbiota: Altered Schaedler Flora," Applied and Environmental Microbiology, 65(8):3287-3292 (1999).
Dieterie et al.; "Renal biomarker qualification submission: a dialog between the FDA-EMEA and Predictive Safety Testing Consortium"; Nature Biotechnology, 2010, vol. 28, No. 5, pp. 455-462.
Dorn et al.; "Invasion of Human Oral Epithelial Cells by Prevotella intermedia"; Infection and immunity, Dec. 1998, vol. 56, No. 12, pp. 6054-6057.
Duncan et al.; "Acetate Utilization and Butyryl Coenzyme A (CoA): Acetate-CoA Transferase in Butyrate-Producing Bacteria from the Human Large Intestine"; Applied and Environmental Microbiology, 2002, vol. 68, No. 10, pp. 5186-5190.

DuPont, "The search for effective treatment of Clostridium difficile infection," N Engl J Med., 364(5):473-475 (2011).
Eckberg et al.; "Diversity of the Human Intestinal Microbial Flora"; Science, vol. 308, p. 1635 (2005).
Edgar; Search and clustering orders of magnitude faster than BLAST; Bioinformatics, 2010, vol. 26, No. 19, p. 2640.
Eiseman et al., "Fecal enema as an adjunct in the treatment of pseudomembranous enterocolitis," Surgery, 44 (5):854-859 (1958).
Extended European Search Report dated Apr. 3, 2014, in European Patent Application No. 11813951.8.
Extended European Search Report dated Nov. 30, 2016, in European Patent Application No. 16193790.9.
Faust et al., "Treatment of recurrent pseudomembranous colitis (RPMC) with stool transplantation (ST): Report of six (6) cases," Can J Gastroenterol., 16:A43 (2002).
Fenton et al., "Pseudomembranous colitis associated with antibiotic therapy—an emerging entity," Can Med Assoc J., 111(10):1110-1111 (1974).
Ferre-Aracil C et al. (2015). "Fecal microbiota transplantation: something more than merely a therapeutic curiosity," Revista Espanola de Enfermedades Digestivas. 107(7): 399-401.
Finegold et al.; "Gastrointestinal Microflora Studies in Lafe-Onset Autism"; Clinical Infectious Diseases, 2002; vol. 35, pp. S6-S16.
Finegold et al.; "Pyrosequencing study of fecal microflora of autistic and control children"; Anaerobe 16, pp. 444-453 (2010).
Finegold, S, et al., (2012). "Microbiology of regressive autism," Anaeribe, 18:260-262.
Floch et al., "Probiotics and Dietary Fiber, The Clinical Coming of Age of Intestinal Microecology," J. Gin Gastroenterology, 27(2):99-100 (1998).
Floch, "Fecal Bacteriotherapy, Fecal Transplant, and the Microbiome," J. Clin. Gastroenterol., 44(8):529-530 (2010).
Flotterod et al., "Refractory Clostridium difficile infection. Untraditional treatment of antibiotic-induced colitis," Tidsskr Nor Laegeforen, 111:1364-1365 (1991).
Fogarty et al., "Comparison of Bacteroides-Prevotella 16S rRNA Genetic Markers for Fecal Samples from Different Animal Species," Applied and Environmental Microbiology, 71(10): 5999-6007 (Oct. 2005).
Frank et al., "Molecular-phylogenetic characterization of microbial community imbalances in human inflammatory bowel diseases," PNAS, 104(34):13780-13785 (2007).
Frantzen et al., "Empirical evaluation of preservation methods for faecal DNA," Molecular Ecology, 7(10):1423-1428 (1998).
Freeman et al., "The changing epidemiology of Clostridium difficile infections," Clin Microbiol. Rev., 23(3):529-549 (2010).
Frese et al., "The evolution of host specialization in the vertebrate gut symbiont Lactobacillus reuteri," PloS Genet., 7 (2):e1001314 (2011).
Gaboriau-Routhiau et al., "The Key Role of Segmented Filamentous Bacteria in the Coordinated Maturation of Gut Helper T Cell Responses," Immunity, 31(4):677-689 (2009).
Garborg et al., "Results of faecal donor instillation therapy for recurrent Clostridium difficile-associated diarrhoea," Scand J Infect Dis., 42(11-12):857-61 (2010).
Garcia-Pena et al.; "Anaerobic digestion and co-digestion processes of vegetable and fruit residues: Process and microbial ecology"; Bioresource Technology, 2011, vol. 102, pp. 9447-9455.
Garey et al., "Meta-analysis to assess risk factors for recurrent Clostridium difficile infection," J. Hosp. Infect., 70 (4):298-304 (2008).
Garrett W et al. (2010). "Homeostasis and Inflammation in the Intestine," Cell, 140(6): 859-870.
Geier et al., "A Comparison of the Autism Treatment Evaluation Checklist (ATEC) and the Childhood Autism Rating Scale (CARS) for the Quantitative Evaluation of Autism," Journal of Mental Health Research in Intellectual Disabilities, 6:255-67 (2013).
Borody et al., "Treatment of Severe Crohn's Disease (CD)—Using Rifabutin-Macrolide-Clofazimine Combination: Results at 30-37 Months," Gastroenterology, 118(4):A1334 Abstract (2000).
Borody et al., "Treatment of Severe Crohn's disease using antimycobacterial triple therapy—approaching a cure?," Digest Liver Dis, 34(1):29-38 (2002).

(56) References Cited

OTHER PUBLICATIONS

Borody et al., "Treatment of ulcerative colitis using fecal bacteriotherapy," J. Clin. Gastroenterol., 37(1):42-47 (2003).
Borody et al., Reversal of Idiopathic Thrombocytopenia Purpura [ITP] with Fecal Microbiota Transplantation [FMT], Am J Gastro, 106(S2):A941 (2011).
Borody et al., Treatment of Severe Crohn's Disease Using Rifabutin-Macrolide-Clofazimine Combination—Results at 38-43 Months, J Gastroenterol & Hepatol, 15(Suppl.):J102 (2000).
Borody T et al. (2013). "Therapeutic Potential of the Human Gastrointestinal Microbiome," Drug Development Research 74: 385-392.
Borody, "Bacteriotherapy for Chronic Fatigue Syndrome—A Long Term Follow-Up Study," Proceedings of ACMA Complementary Medicine Sydney, p. 1 (1995).
Borody, "Flora Power—Fecal Bacteria Cure Chronic C. difficile Diarrhoea," Am J Gastroenterol, 95(11):3028-3029 (2000).
Borody, "Is the Infected Patient too 'Difficile' to Treat?," The Australian Society for Microbiology 2009 Perth, SY03 & SY03.1, p. 27 & 56, (2009).
Borody, "Letter to the Editor—Response to Drs. Famularo et al.," AJG, 96(7):2262-2264 (2001).
Bowden et al., "Pseudomembraneous enterocolitis: mechanism of restoring floral homeostasis," Am Surg., 47 (4):178-183 (1981).
Brandt et al., "Endoscopic Fecal Microbiota Transplantation: "First-Line" Treatment for Severe Clostridium difficile Infection?" J. Clin. Gastroenterol., 45(8):655-657 (2011).
Brandt et al., "Fecal microbiota transplantation for recurrent Clostridium difficile infection," J Clin Gastroenterol., 45 (Suppl):S159-S167 (2011).
Brandt et al., "Long-Term Follow-Up Study of Fecal Microbiota Transplantation (FMT) for Ulcerative Colitis (UC)," Am. J. Gastroenterol., 107(Suppl 1):S657 (2012).
Brandt et al., Safety of Fecal Microbiota Transplantation (FMT) in Immunocompromised (IC) Patients with Inflammatory Bowel Disease (IBD), Am J Gastroenterol, 108(Suppl 1):S556 (2013).
Browne et al., "Culturing of 'unculturable' human microbiota reveals novel taxa and extensive sporulation," Nature, 533 (7604):543-546 (2016).
Bryant et al.; "Bacteroides Ruminicola N. Sp. and the New Genus and Species *Succinnimonas amylolylica*"; Journal of Bacteriol. vol. 76, pp. 15-23; 1958.
Bryant R et al. (2014). "Systematic review: Histological remission in inflammatory bowel disease. Is 'complete' remission the new treatment paradigm? An IOIBD initiative," Journal of Crohn's and Colitis, 8(12): 1582-1597.
Bueche et al., "Quantification of Endospore-Forming Firmicutes by Quantitative PCR with the Functional Gene spo0A," Applied and Environmental Microbiology, 79(17):5302-5312 (2013).
Buie et al.; "Evaluation, Diagnosis, and Treatment of Gastrointestinal Disorders in Individuals With ASDs: A Consensus Report"; Pediatrics, vol. 125, pp. S1-S18; 2010.
Cammarota G (2016). "Principles of DNA-Based Gut Microbiota Assessment and Therapeutic Efficacy of Fecal Microbiota Transplantation in Gastrointestinal Diseases," Digestive Diseases 34(3): 279.
Cammorata et al., "Review article: biofile formation by Helicobacter pylori as a target for eradication of resistant infection," Aliment Pharmacol Ther, 36:222-30 (2012).
Campbell et al., "The many faces of Crohn's Disease: Latest concepts in etiology," OJIM, 2(2):107-115 (2012).
Cangelosi et al., "Dead or Alive: Molecular Assessment of Microbial Viability," Applied and Environmental Microbiology, 80(19):5884:5891 (2014).
Cano et al., "Revival and identification of bacterial spores in 25-40 million year old Dominican Amber Science," Science, 268(5213):1060-1064 (1995).
Cato et al., "Clostridium oroticum comb. nov. amended description," International Journal of Systematic Bacteriology, 17(1):9-13 (1968).
Celik et al., "Factors influencing the stability of freeze-dried stress-resilient and stress-sensitive strains of bifidobacteria," J. Dairy Sci., 96(6):3506-16 (2013).
Cenit M et al. (2014). "Rapidly expanding knowledge on the role of the gut microbiome in health and disease," Biochimica et Biophysica Acta—Molecular Basis of Disease, 1842(10): 1981-1992.
Center for Disease Control, "Severe Clostridium difficile-associated disease in populations previously at low risk—four states, 2005." Morbidity and Mortality Weekly Report, 54(47):1201-1205 (2005).
Chaidez, V., et al.. (2014). "Gastrointestinal Problems in Children with Autism, Development Delays or Typical Development." J. Autism Dev Disord, 44:1117-1127.
Chamberlain et al., "MAP-associated Crohn's Disease, MAP, Koch's postulates, causality and Crohn's Disease," Digestive and Liver Disease, 39:790-794 (2007).
Chamberlin et al., "Primary treatment of Crohn's disease: combined antibiotics taking center stage," Expert Rev. Clin. Immunol., 7(6):751-760 (2011).
Chang et al., "Decreased diversity of the fecal Microbiome in recurrent Clostridium difficile-associated diarrhea," J. Infect. Dis., 197(3):435-438 (2008).
Chao et al.; "Estimating the Number of Classes via Sample Coverage"; Journal of the American Statistical Association; 1992; vol. 87, No. 417, pp. 210-217.
Chen et al., "A mouse model of Clostridium difficile-associated disease," Gastroenterology, 135(6):1984-1992 (2008).
Cherif et al., "Thuricin 7: a novel bacteriocin produced by Bacillus thuringiensis BMG1.7, a new strain isolated from soil," Letters in Applied Microbiology, 32:243-7 (2001).
Choi et al., "Fecal Microbiota Transplantation: Current Applications, Effectiveness, and Future Perspectives," Clin. Endosc., 49:257-265 (2016).
Chopra et al., "Recent epidemiology of Clostridium difficile infection during hematopoietic stem cell transplantation," Clin Transplant., 25(1):E82-E87 (2011).
Chu et al., "Profiling Living Bacteria Informs Preparation of Fecal Microbiota Transplantations," PLOS One, 1-16 (2017).
Citron et al., "In Vitro Activities of CB-183,315, Vancomycin, and Metronidazole against 556 Strains of Clostridium difficile, 445 Other Intestinal Anaerobes, and 56 *Enterobacteriaceae* Species," Antimicrob Agents Chemother., 56 (3):1613-1615 (2012).
Claesson et al., "Comparison of two next-generation sequencing technologies for resolving highly complex microbiota composition using tandem variable 16S rRNA gene regions," Nucleic Acids Research, 38(22):1-13 (2010).
Clancy et al., "Anti-MAP Therapy Induces and Maintains Remission in Severe Crohn's Disease," Ann NY Acad Sci, p. 1 (2005).
Claus et al., "Colonization-induced host-gut microbial metabolic interaction," MBio, 2(2):e00271-00210 (2011).
Claus et al., "Systemic multicompartmental effects of the gut microbiome on mouse metabolic phenotypes," Mol. Syst. Biol., 4(1):219 (2008).
Clemente J et al. (2012). "The Impact of the Gut Microbiota on Human Health: An Integrative View," Cell, 148(6):1258-1270.
Cohen et al., "Clinical practice guidelines for Clostridium difficile infection in adults: 2010 update by the society for healthcare epidemiology of America (SHEA) and the infectious diseases society of America (IDSA)," Infect Control Hosp Epidemiol., 31(5):431-55 (2010).
Cohen et al., "The PDD Behavior Inventory: A Rating Scale for Assessing Response to Intervention in Children with Pervasive Developmental Disorder," Journal of Autism and Developmental Disorders, (33)1:31-45 (2003).
Cole et al.; "Psychological Risk Factors for HIV Pathogenesis: Mediation by the Autonomic Nervous System"; Society of Biological Psychiatry, 2003, vol. 54, pp. 1444-1456.
Cole et al.; "The Ribosomal Database Project {RDP-11): previewing a new autoaligner that allows regular updates and the new prokaryotic taxonomy"; Nucleic Acids Research; 2009; vol. 31, No. 1, pp. 442-443.
Cole et al.; "The Ribosomal Database Project: improved alignments and new tools for rRNA analysis"; Nucleic Acids Research, 2008, vol. 37, pp. D141-D145.

(56) References Cited

OTHER PUBLICATIONS

Schwan et al., "Relapsing Clostridium Difficile Enterocolitis Cured by Rectal Infusion of Homologous Faeces," The Lancet, 322(8354):845 (1983).
Schwan et al., "Relapsing Clostridium difficile Enterocolitis Cured by Rectal Infusion of Normal Faeces," Scand. J. Infect. Dis., 16(2):211-215 (1984).
Seeff et al., "How many endoscopies are performed for colorectal cancer screening? Results from CDC's survey of endoscopic capacity," Gastroenterology, 127:1670-1677 (2004).
Sekirov et al., "Gut microbiota in health and disease," Physiol. Rev., 90(3):859-904 (2010).
Setlow, "I Will Survive: Protecting and Repairing Spore DNA," Journal of Bacteriology, 174(9):2737-2741 (1992).
Setlow, "The bacterial spore: nature's survival package," Culture, 26(2):1-4 (2005).
Sghir et al., "Quantification of Bacterial Groups within Human Fecal Flora by Oligonucleotide Prode Hybridization," Applied and Environmental Microbiology, 66(5):2263-2266 (2000).
Shah et al. International Journal of Systematic Bacteriology 1990, vol. 40, No. 2, pp. 205-208.
Shanahan F et al. (2014). "Manipulation of the Microbiota for Treatment of IBS and IBD—Challenges and Controversies," Gastroenterology, 146(6): 1554-1563.
Shim et al., "Primary symptomless colonisation by Clostridium difficile and decreased risk of subsequent diarrhea," The Lancet, 351(9103):633-666 (1998).
Silverman et al., "Success of self-administered home fecal transplantation for chronic Clostridium difficile infection," Clin. Gastroenterol. Hepatol., 8(5):471-473 (2010).
Simor et al., "Clostridium difficile in long-term-care facilities for the elderly," Infect Control Hosp Epidemiol., 23 (11):696-703 (2002).
Singh et al., "Do NSAIDs, antibiotics, infections, or stress trigger flares in IBD?" Am J Gastroenterol., 104(5):1298-1313 (2009).
Sleator, "The human superorganism—of microbes and men," Med. Hypotheses, 74(2):214-215 (2010).
Smits et al., "Therapeutic potential of fecal microbiota transplantation," Gastroenterology, 145:946-953 (2013).
Sokol et al., "Low Counts of Faecalibacterium prausnitzii in Colitis Microbiota," Inflamm. Bowel Dis., pp. 1-7 (2009).
Sokol et al., Faecalibacterium prausnitzii is an anti-inflammatory commensal bacterium identified by gut microbiota analysis of Crohn disease patients, Proceedings of the National Academy of Sciences, 105(43):16731-16736 (2008).
Song et al.; "Real-Time PCR Quantitation of Clostridia in Feces of Autistic Children"; Applied and Environmental Microbiology; Nov. 2004; vol. 70, No. 11, pp. 6459-6465.
Sparrow et al., "Vineland Adaptive Behavior Scales," 2nd Edition American Guidance Service, 3 (2005).
Stocks, "Mechanism and Use of Commercially Available Viability Stain, BacLight," Cytometry Part A, 61(A):189-195 (2004).
Sun et al.; "Tag-Encoded FLX Amplicon Pyrosequencing forthe Elucidation of Microbial and Functional Gene Diversity in Any Environment"; Methods and Applications, Methods in Molecular Biology; 2011; vol. 733, pp. 129-141.
Sun J et al. (2014). "Exploring gut microbes in human health and disease: Pushing the envelope," Genes & Diseases, 1(2): 132-139.
Sunil et al., "Design and evaluation of lornoxicam bilayered tablets for biphasic release," Brazilian Journal of Pharmaceutical Sciences, 48(4):609-19 (2012).
Surawicz et al., "Treatment of refractory and recurrent Clostridium difficile infection," Nat. Rev. Gastroenterol. Hepatol., 8(6):330-339 (2011).
Surawicz, "Reining in Recurrent Clostridium difficile Infection—Who's at Risk?," Gastroenterology, 136:1152-1154 (2009).
Sutherland et al., "Lyophilized Clostridium perfringens 3 alpha- and Clostridium bifeimentans 7 alpha-hydroxysteroid dehydrogenases: two new stable enzyme preparations for routine bile acid analysis," Biochim Biophys Acta, 962 (1):116-121 (1988).

Swidsinski A et al. (2002). "Mucosal flora in inflammatory bowel disease," Gastroenterology, 122(1): 44-54.
Takaishi et al., "Imbalance in intestinal microflora constitution could be involved in the pathogenesis of inflammatory bowel disease," J. Med. Microbiol., 298:463-472 (2008).
Takeda et al., "Serum Haloperidol Levels of Schizophrenics Receiving Treatment for Tuberculosis," Clinical Neuropharmacology, 9(4):386-397 (1986).
Tannock et al., "A new macrocyclic antibiotic, fidaxomicin (OPT-80), causes less alteration to the bowel microbiota of Clostridium difficile-infected patients than does vancomycin," Microbiology, 156(11):3354-3359 (2010).
Tap et al.; "Towards the human intestinal microbiota phylogenetic code"; Environmental Microbiology; 2009; vol. 11 (10), pp. 2574-2584.
Taras et al., "Reclassification of Eubacterium formicigenerans Holdeman and Moore 1974 as *Dorea formicigenerans* gen. nov., comb, nov., and description of *Dorea longicatena* sp. nov., isolated from human faeces," International Journal of Systematic and Evolutionary Microbiology, 52:423-428 (2002).
Teasley et al., "Prospective randomised trial of metronidazole versus vancomycin for Clostridium-difficile-associated diarrhoea and colitis," The Lancet, 2(8358):1043-1046 (1983).
Tilg et al., "Gut microbiome, obesity, and metabolic dysfunction," J. Clin. Invest., 121(6):2126-2132(2011).
Trent et al.; "Diversity of endotoxin and its impact on pathogenesis"; Journal Endotoxin Research; 2006; vol. 12, No. 4, pp. 205-223.
Turnbaugh et al.; "A core gut microbiome in obese and lean twins"; Nature; Jan. 22, 2009; vol. 457, pp. 480-484.
Tvede et al., "Bacteriotherapy for chronic relapsing Clostridium difficile diarrhea in six patients," The Lancet, 1:1156-1160 (1989).
U.S. Securities and Exchange Commission, Form 8-K Report, Assembly Bioscience, Inc., Feb. 24, 2015.
Udall et al.; "Development of Gastrointestinal Mucosal Barrier. I. The Effect of Age on Intestinal Permeability to Macromolecules"; Journal of Pediatric Research; 1981; vol. 15, pp. 241-244.
Ursell L et al. (2014). "The Intestinal Metabolome: An Intersection Between Microbiota and Host," Gastroenterology 146:1470-1476.
Van Andel et al., "Interleukin-12 Has a Role in Mediating Resistance of Murine Strains to Tyzzer's Disease," Infect. Immun., 66(10):4942-4946 (1998).
Van der Waaij et al., "Direct Flow Cytometry of Anaerobic Bacteria in Human Feces," Cytometry, 16:270-279 (1994).
Van Immerseel et al., "Butyric acid-producing anaerobic bacteria as a novel probiotic treatment approach for inflammatory bowel disease," Journal of Medical Microbiology, 59:141-143 (2010).
Van Nood et al., "Struggling with Recurrent Clostridium difficile Infections: Is Donor Faeces the Solution?," Euro Surveill., 14(34):1-6 (2009).
Van Nood, "Duodenal infusion of donor feces for recurrent Clostridium difficile," New England Journal of Medicine, 368 (5):407-415 (2013).
Veldhuyzen van Zanten et al., "Drug Treatment of Functional Dyspepsia: A Systematic Analysis of Trial Methodology with Recommendations for Design of Future Trials," Am. J. Gastroenterol., 91(4):660-673 (1996).
Veldhuyzen van Zanten et al., "Validation of a 7-point Global Overall Symptom scale to measure the severity of dyspepsia symptoms in clinical trials," Ailment Pharmacol. Ther., 23(4):521-529 (2006).
Venugopal et al., "Fidaxomicin: A Novel Macrocyclic Antibiotic Approved for Treatment of Clostridium difficile Infection," Clin Infect Dis, 54(4):568-74 (2012).
Vidhyalakshmi et al.; "Encapsulation 'The Future of Probiotics'—A Review"; Advances in Biological Research 3 (3-4), pp. 96-103; 2009.
Vrieze et al., "The environment within: how gut microbiota may influence metabolism and body composition," Diabetologia, 53(4):606-613 (2010).
Martin, "Development and Delivery of a Treatment for Clostridium difficile," Bacteriotherapy, pp. 1-2, n.d., Web, Feb. 10, 2012 <www.bacteriotherapy.org>.

(56) References Cited

OTHER PUBLICATIONS

Martin-Dejardin et al., "A way to follow the viability of encapsulated Bifidobacterium bifidum subjected to a freeze-drying process in order to target the colon: Interest of flow cytometry," European Journal of Pharmaceutical Sciences, 49:166-74 (2013).
Maslowski et al., "Diet, gut microbiota and immune responses," Nat Immunol., 12(1):5-9 (2011).
McDonald et al., "An Epidemic, Toxin Gene-Variant Strain of Clostridium difficile," N Engl J Med., 353(23):2433-41 (2005).
McDonald et al., "Clostridium difficile Infection in Patients Discharged from US Short-stay Hospitals, 1996-2003" Emerg. Infect. Dis, 12(3):409-415 (2006).
McFarland et al., "Implications of the changing face of Clostridium difficile disease for health care practitioners," Am J Infect Control., 35(4):237-253 (2007).
McFarland et al., "Meta-Analysis of Probiotics for the Prevention of Antibiotic Associated Diarrhea and the Treatment of Clostridium difficile Disease," Am J Gastroenterol., 101(4):812-22 (2006).
McFarland et al., "Nosocomial Acquisition of Clostridium Difficile Infection," N Engl J Med., 320(4):204-210 (1989).
McFarland et al., "Recurrent Clostridium Difficile Disease: Epidemiology and Clinical Characteristics," Infect Control Hosp Epidemiol., 20(1):43-50 (1999).
McFarland et al., "Renewed interest in a difficult disease: Clostridium difficile infections—epidemiology and current treatment strategies," Curr Opin Gastroenterol., 25(1):24-35 (2008).
McGarland et al., "Breaking the Cycle: Treatment Strategies for 163 Cases of Recurrent Clostridium difficile Disease," Am. J. Gastroenterol., 97(7):1769-1775 (2002).
Meadows; "Gut Bacteria May Override Genetic Protections Against Diabetes"; PLOS Biology, Dec. 2011, vol. 9, No. 12, e1001215 (1 page).
Miller et al., "Health care-associated Clostridium difficile infection in Canada: patient age and infecting strain type are highly predictive of severe outcome and mortality," Clin Infect Dis., 50(2):194-201 (2010).
Miller et al., "Long-term follow-up of patients with fulminant Clostridium difficile colitis," J. Gastroint. Surg., 13 (5):956-959 (2009).
Miller et al., "Morbidity, mortality, and healthcare burden of nosocomial Clostridium difficile-associated diarrhea in Canadian hospitals," Infect Control Hosp Epidemiol., 23(3):137-40 (2002).
Miller, "The fascination with probiotics for Clostridium difficile infection: lack of evidence for prophylactic or therapeutic efficacy," Anaerobe, 15(6):281-284 (2009).
Minami et al.; "Effects of lipopolysaccharide and chelator on mercury content in the cerebrum of thimerosal administered mice"; Environmental Toxicology and Pharmacology 24 (2007), pp. 316.
Minami et al.; "Roles of nitric oxide and prostaglandins in the increased permeability of the blood-brain barrier caused by lipopolysaccharide"; Environmental Toxicology and Pharmacology 5 (1998), pp. 35-41.
Moayyedi et al., "Fecal Microbiota Transplantation Induces Remission in Patients With Active Ulcerative Colitis in a Randomized Controlled Trial," Gastroenterology, 149(1):102-9 (2015).
Molecular Studies in Autism, 2004 Funding Cycle, Cure Autism Now, Cure Autism Now Foundation, pp. 1-7 (2005) <www.cureautismnow.org>.
Molloy et al.; "Prevalence of chronic gastrointestinal symptoms in children with autism and autistic spectrum disorders" Autism, vol. 7, No. 2, pp. 165-171; 2003.
Momose et al., "16S rRNA gene sequence-based analysis of Clostridia related to conversion of germfree mice to the normal state," Journal of Applied Microbiology, 107:2088-2097 (2009).
Morris et al., "Clostridium difficile Colitis: An Increasingly Aggressive Iatrogenic Disease?" Arch Surg., 137 (10):1096-1100 (2002).
Mullard, "Microbiology: The Inside Story," Nature, 453:578-580 (2008).

Mulloy et al.; "Gluten-free and casein-free diets in the treatment of autism spectrum disorders: A systematic review"; Research in Autism Spectrum Disorders; 2010; vol. 4, pp. 328-339.
Mutaflor, "Brief Summary of Therapeutic Principles," Ardeypharm GmbH 0796 D-58313 Herdecke Germany, 6 pgs (2006).
Mutaflor, "For Functional and Inflammatory Bowel Diseases for Extraintestinal Manifestations for Activation of the Body's In-Built Defences," Ardeypharm GmbH 0796, D-58313 Herdecke Germany, 8 pgs (2006).
Mutaflor, "Safety of Therapy," Ardeypharm GmbH 0796, D-58313 Herdecke Germany, 4 pgs (1988).
Muto et al., "A Large Outbreak of Clostridium difficile-Associated Disease with an Unexpected Proportion of Deaths and Colectomies at a Teaching Hospital Following Increased Fluoroquinolone Use," Infect Control Hosp Epidemiol., 26 (3):273-80 (2005).
Neish A (2009). "Microbes in Gastrointestinal Health and Disease," Gastroenterology, 136(1): 65-80.
Niehaus et al.; "Early Medical History of Children with Autism Spectrum Disorders"; Journal of Development and Behavioral Pediatrics; Apr. 2006; vol. 27, No. 2, pp. S120-S127.
Nieuwdorp et al., ["Treatment of recurrent Clostridium difficile-associated diarrhoea with a suspension of donor faeces"], Ned Tijdschr Geneeskd, 152(35):1927-32 (2008) (English absract).
Niu et al., "Prevalence and Impact of Bacteriophages on the Presence of Escherichia coli O157 :H7 in Feedlot Cattle and Their Environment," Applied and Environmental Microbiology, 75(5): 1271-8 (2009).
O'Brien et al., "The emerging infectious challenge of Clostridium difficile-associated disease in Massachusetts hospitals: clinical and economic consequences," Infect Control Hosp Epidemiol., 28(11):1219-27 (2007).
Ochoa-Reparaz et al.; "Gut, Bugs, and Brain: Role of Commensal Bacteria in the Control of Central Nervous System Disease"; Annals Neurology, 2011; vol. 69, pp. 240-247.
O'Connor et al., "Clostridium difficile Infection Caused by the Epidemic BI/NAP1/027 Strain," Gastroenterology, 136 (6):1913-1924 (2009).
Office Action dated Sep. 18, 2015, in European Patent Application No. 11 728 077.6.
O'Garra et al., "IL-10-producing and naturally occuring CD4+ Tregs: limiting collateral damage," The Journal of Clinical Investigation, 114:1372-1378 (2004).
O'Hara et al., "The gut flora as a forgotten organ," EMBO Rep., 7(7):688-693 (2006).
O'Hara et al.; "Functional modulation of human intestinal epithelial cell responses by Bifidobacterium infantis and Lactobacillus salivarius"; Immunology, 2006, vol. 118, pp. 202-215.
Okada et al., "Effects of Fecal Microorganisms and Their Chloroform-Resistant Variants Derived from Mice, Rats, and Humans on Immunological and Physiological Characteristics of the Intestines of Ex-germfree Mice," Infection and Immunity, 62(12):5442-5446 (1994).
Ott et al., "Efficacy of Sterile Fecal Filtrate Transfer for Treating Patients With Clostridium difficile Infection," Gastroenterology, 152(4):799-811 (2017).
Owyang C et al. (2014). "The Gut Microbiome in Health and Disease," Gastroenterology, 146(6): 1433-1436.
Paramsothy et al., "Gastroenterologist perceptions of faecal microbiota transplantation," World J Gastroenterol, 21(38): 10907-10914 (2015).
Paramsothy et al., "Multidonor intensive faecal microbiota transplantation for active ulcerative colitis: a randomised placebo-controlled trial," The Lancet, published online, 11 pages (2017).
Parracho et al.; "Differences between the gut microflora of children with autistic spectrum disorders and that of healthy children"; Journal of Medical Microbiology; 2005; vol. 54, pp. 987-991.
Passel et al.; "The Genome of Akkermansia muciniphila, a Dedicated Intestinal Mucin Degrader, and Its Use in Exploring Intestinal Metagenomes"; Mar. 2011; Plos One vol. 6, Issue 3, e16876 (8 pages).
Patterson et al., "Special organism isolation: attempting to bridge the gap," Infect Control Hosp Epidemiol., 15 (5):335-338 (1994).
Pearce et al., "Modification of the colonic microflora using probiotics: The way forward?," Gut, 41(Suppl 3):A63 (1997).

(56) References Cited

OTHER PUBLICATIONS

Pearce et al., "The use of probiotic therapy as a novel approach to the management of irritable bowel syndrome: a preliminary study," J Gastroenterol & Hepatol, 12(Suppl):A129 (1997).
"ARGF—'Autologous Rehabilitation of Gastrointestinal Flora,'" Medipex Report for Medilink NW, pp. 1-42, n.d., Web, Feb. 10, 2012 <http://www.bacteriotherapy.org/docs/medipex-report.pdf>.
"Autoimmune Disease List," American Autoimmune Related Diseases Association, pp. 1-4 (2017) <https://www.aarda.org/diseaselist/>.
"Certain infectious and parasitic diseases (A00-B99)," International Statistical Classification of Diseases and Related Health Problems, 10th Revision (ICD-10)—WHO Version, Chapter 1, pp. 1 (2016) <www.apps.who.int/classifications/icd10/browse/2016/en#/I>.
"Frequently Asked Questions about Clostridium difficile for Healthcare Providers," Healthcare-associated Infections (HAIs), Centers for Disease Control and Prevention, pp. 1-6, Nov. 25, 2010, updated Mar. 6, 2012, Web, May 19, 2014 <http://www.cdc.gov/HAI/organisms/cdiff/Cdiff_faqs_HCP.html>.
"Functional Anatomy of Prokaryotic and Eukaryotic Cells," printed Mar. 16, 2017 <http://classes.midlandstech.edu/carterp/courses/bio225/chap04/lecture2.htm>.
"Monilia," Def. 1, Stedman's Medical Dictionary, n.d., Web, Nov. 22, 2005.
"Probiotic," Def. 1, MSN Encarta—Dictionary, Encarta, n.d., Web, Dec. 1, 2005.
"Spore-Forming Gram-Positive Bacilli: *Bacillus* and *Clostridium* Species," Jawetz, Melnick, & Adelberg's Medical Microbiology, 26th Edition, Chapter 11, pp. 1-15 (2012).
Aas et al., "Recurrent Clostridium difficile Colitis: Case Series Involving 18 Patients Treated with Donor Stool Administered via a Nasogastric Tube," Clinical Infectious Diseases, 36(5):580-585 (2003).
Abrams, "Open-Label, Uncontrolled Trial of Bowel Sterilization and Repopulation with Normal Bowel Flora for Treatment of Inflammatory Bowel Disease," Current Therapeutic Research, 58(12):1001-1012 (1997).
Abstract Book. IHMC: 5th International Human Microbiome Congress. (2015).
Acha et al., "Changes of viability and composition of the *Escherichia coli* flora in faecal samples during long time storage," Journal of Microbiological Methods, Elsevier, 63(3):229-238 (2005).
Adams et al., "Effect of a Vitamin/Mineral Supplement on Children and Adults with Autism" BMC Pediatrics, 11:111, 30 pages (2011).
Adams et al., "The Severity of Autism is Associated with Toxic Metal Body Burden and Red Blood Cell Glutathione Levels," J. Toxicol, 2009:532640, 7 pages (2009).
Adams et al.; "Gastrointestina flora and gastrointestinal status in children with autism-comparisons to typical children and correlation with autism severity"; Bmc Gastroenterol., 2011, 11 :22, pp. 1-13.
Adams, J., et al., "Gut Bacteria in Children with Autism," 1st International Symposium on the Microbiome in Health and Disease with a Special Focus on Autism, 2014.
Agrawal et al., "'Global warming' to *Mycobacterium avium* subspecies *paratuberculosis*," Future Microbiol, 9 (7):829-832 (2014).
Agrawal et al., "A Long-Term Follow-Up Study of the Efficacy and Safety of Fecal Microbiota Transplant (FMT) for Recurrent/Severe/Complicated C. difficile Infection (CDI) in the Elderly," Gastroenterol, 146(5)(Suppl 1):S42-43 (2014).
Aitken et al., "Demonstration of Intracellular Mycobacterium Species in Crohn's Disease Using Novel Technologies," Poster Presentation—2015 ACG Annual Scientific Meeting, Honolulu, Hawaii, USA (2015).
Akao et al., "A Purgative Action of Barbaloin Is Induced by Eubacterium sp. Strain BAR, a Human Intestinal Anaerobe, Capable of Transforming Barbaloin to Aloe-Emodin Anthrone," Biol. Pharm., 19(1):136-138 (1996).
Al-Eidan et al., "Clostridium difficile-associated diarrhoea in hospitalised patients," J. Clin. Pharm. Ther., 25(2):101-109 (2000).

Al-Nassir et al., "Comparison of Clinical and Microbiological Response to Treatment of Clostridium difficile-Associated Disease with Metronidazole and Vancomycin," Clin Infect Dis., 47(1):56-62 (2008).
Aman et al., "Psychometric Characteristics of the Aberrant Behavior Checklists," Am. J. Ment. Deffic., 89(5):492-502 (1985).
Anand et al., "Epidemiology, clinical manifestations, and outcome of Clostridium difficile-associated diarrhea," Am J Gastroenterol., 89(4):519-23 (1994).
Ananthakrishnan et al., "Excess hospitalisation burden associated with Clostridium difficile in patients with inflammatory bowel disease," Gut, 57(2):205-210 (2007).
Anderson et al., "Systematic review: faecal microbiota transplantation in the management of inflammatory bowel disease," Aliment. Pharmacol. Ther., 36:503-16 (2012).
Andoh et al., "Terminal restriction fragment polymorphisum analyses of fecal microbiota in five siblings including two with ulcerative colitis," Journal of Clinical Gastroenterology, 2:343-345 (2009).
Andrews et al., "'Putting back the bugs': Bacterial Treatment Relieves Chronic Constipation and Symptoms of Irritable Bowel Syndrome," Med. J. Aust., 159(9):633-634 (1993).
Andrews et al., "Bacteriotherapy for Chronic Constipation—A Long Term Follow-Up," Gastroenterol, 108:A563 Abstract (1995).
Andrews et al., "Chronic Constipation (CC) may be reversed by Bacteriotherapy," Gastroenterol, 106:A459 (1994).
Andrews et al., "Chronic constipation reversed by restoration of bowel flora. A case and a hypothesis," European Journal of Gastroenterology & Hepatology, 4:245-247 (1992).
Anorexia nervosa, Encyclopedia Index A, healthAtoZ, Medical Network, Inc., pp. 1-7, n.d., Web, Nov. 23, 2005 <http://www.healthatoz.com/healthatoz/Atoz/ency/anorexia_nervosa.jsp>.
Arkkila et al., "Fecal Bacteriotherapy for Recurrent Clostridium difficile Infection," Gastroenterology, 138(5):S1-S5 (2010).
Aroniadis et al., "Intestinal Microbiota and the Efficacy of Fecal Microbiota Transplantation in Gastrointestinal Disease," Gastroenterology and Hepatology, 10(4):230-7 (2014).
Aroniadis et al., "Long-Term Follow-up Study of Fecal Microbiota Transplantation (FMT) for Severe or Complicated Clostridium difficile Infection (CDI)," Gastroenterol, 144(Suppl 1):S185 (2013).
Arumugam et al.; "Enterotypes of the human gut microbiome"; Nature, 2011, vol. 473, pp. 174-180.
Atarashi et al., "Treg induction by a rationally selected mixture of Clostridia strains from the human microbiota," Nature, 500(7461):232-236 (2013).
Atarashi et al., "WS/PP-064-03 Regulation of colonic regulatory T cells by *Clostridium* species," International Immunology, 22(Suppl 1, Part 3), pp. 1-3 (2010).
Atarashi et al., WS-064 Mucosal immunity: homeostasis, 14th ICIC Abstract book, 14th International Congress of Immunology, pp. iii131-iii133 (2010).
Atarashi et al.; "Induction of Colonic Regulatory T Cells by Indigenous *Clostridium* Species"; 331, Science, 2011, pp. 337-341.
Autism, Health Encyclopedia—Diseases and Conditions, The Health Scout Network, pp. 1-5, n.d., Web, Nov. 22, 2005 <www.healthscout.com>.
Autism, Treatment, Prognosis, Healthcommunities.com, Inc., pp. 1-4, n.d., Web. Jan. 28, 2009 <http://www.neurologychannel.com/common/PrintPage.php>.
Autism: Mayo Clinic.com, Mayo Foundation for Medical Education and Research, pp. 1-7, May 31, 2008, Web. Jan. 28, 2009 <http://www.mayoclinic.com/print/autism/DS00348/METHOD=print&DSECTION=all>.
Backhed et al., "Host-bacterial mutualism in the human intestine," Science, 307(5717):1915-1920 (2005).
Backhed et al., "Mechanisms underlying the resistance to diet-induced obesity in germ-free mice," PNAS USA, 104 (3):979-984 (2007).
Backhed et al., "The gut microbiota as an environmental factor that regulates fat storage," PNAS USA, 101 (44):15718-15723 (2004).
Bakken et al., "Fecal bacteriotherapy for recurrent Clostridium difficile infection," Anaerobe, 15(6):285-289 (2009).

(56) References Cited

OTHER PUBLICATIONS

Bakken et al., "Treating Clostridium difficile Infection with Fecal Microbiota Transplantation," Clinical Gastroenterology and Hepatology, 9(12):1044-1049 (2011).
Kuijper et al. "Update of Clostridium difficile Infection due to PCR Ribotype 027 in Europe, 2008," Euro. Surveill., 13 (31):Article 5 (2008).
Kuksal et al., "Formulation and In Vitro, In Vivo Evaluation of Extended-release Matrix Tablet of Zidovudine: Influence of Combination of Hydrophilic and Hydrophobic Matrix Formers," AAPS Pharm., 7(1):E1-E9 (2006).
Kunde et al., "Safety, Tolerability, and Clinical Response After Fecal Transplantation in Children and Young Adults With Ulcerative Colitis," JPNG, 56(6):597-601 (2013).
Kushak et al.; "Intestinal disaccharidase activity in patients with autism"; Autism, 2011, vol. 15, No. 3, pp. 285-294.
Kyne et al., "Association between antibody response to toxin A and protection against recurrent Clostridium difficile diarrhea," Lancet, 357(9251):189-93 (2001).
Kyne et al., "Asymptomatic carriage of Clostridium difficile and serum levels of IgG antibody against toxin A," N Engl J Med., 342(6):390-397 (2000).
Kyne et al., "Factors associated with prolonged symptoms and severe disease due to Clostridium difficile," Age and Ageing, 28(2):107-13 (1999).
Kysela et al., "Serial analysis of V6 ribosomal sequence tags (SARST-V6): a method for efficient, high-throughput analysis of microbial community composition," Environmental Microbiology, 7(3):356-364 (2005).
Kyselova et al.; "Alterations in the Serum Glycome Due to Metastatic Prostate Cancer"; Journal of Proteome Research, Apr. 14, 2007, vol. 6, pp. 1822-1832.
Labbé et al., "Clostridium difficile infections in a Canadian tertiary care hospital before and during a regional epidemic associated with the BI/NAP1/027 strain," Antimicrob Agents Chemother., 52(9):3180-7 (2008).
Lamontagne et al., "Impact of emergency colectomy on survival of patients with filminant Clostridium difficile colitis during an epidemic caused by a hypervirulent strain," Ann. Surg., 245(2):267-272 (2007).
Larsen et al., "Gut Microbiota in Human Adults with Type 2 Diabetes Differs from Non-Diabetic Adults," PLoS ONE, 5 (2): e9085-e9095 (2010).
Lau et al., "Bacteraemia caused by Anaerotruncus colihominisand emended description of the species," J Clin Pathol, 59:748-752 (2006).
Lawson et al., "*Anaerotruncus colihominis* gen. nov., sp. nov., from human faeces," International Journal of Systematic and Evolutionary Microbiology, 54:413-417 (2004).
Lawson et al., "Anaerotruncus," Bergey's Manual of Systematics of Archae and Bacteria, pp. 1-4 (2009).
Lederberg; "Infectious history"; Science (2000), 288 (5464): 287 (18 pages).
Lee et al.; "Discriminative prediction of mammalian enhancers from DNA sequence"; 2011 Genome Research, vol. 21, pp. 2167-2180.
Lee et al.; "Has the Microbiota Played a Critical Role in the Evolution of the Adaptive Immune System?"; Dec. 24, 2010; Science, vol. 330, pp. 1768-1773 (7 pages).
Lee et al.; "Prioritizing candidate disease genes by network-based boosting of genome-wide association data"; Genome Research, 2011, 21:1, pp. 1109-1121.
Lee, "A Prospective Randomized Multi-Centre Trial of Fresh vs. Frozen-and-Thawed Human Biotherapy (Fecal Transplant) for Recurrent Clostridium difficile Infection," U.S. National Institutes of Health, Clinical Study No. NCT01398969, pp. 1-4, last updated Feb. 27, 2014, Web, May 20, 2014 <http://clinicaltrials.gov/ct2/show/NCT01398969>.
Leis et al., "Fecal microbiota transplantation: A 'How-To' guide for nurses," Collegian, 22:445-451 (2015).
Lewis et al., "Stool form scale as a useful guide to intestinal transit time," Scand. J. Gastroenterol., 32(9):920-924 (1997).
Ley et al., "Ecological and evolutionary forces shaping microbial diversity in the human intestine," Cell, 124:837-848 (2006).
Ley et al., "Evolution of mammals and their gut microbes," Science, 320(5883):1647-1651 (2008).
Ley et al., "Microbial ecology: human gut microbes associated with obesity," Nature, 444(7122):1022-3 (2006).
Ley et al., "Worlds within worlds: evolution of the vertebrate gut microbiota," Nat. Rev. Microbiol., 6(10):776-788 (2008).
Li Q (2014). "Therapeutic modulation and reestablishment of the intestinal microbiota with fecal microbiota transplantation resolves sepsis and diarrhea in a patient," The American Journal of Gastroenterology 109(11): 1832.
Li Q et al. (2016). "The microbiota-gut-brain axis and its potential therapeutic role in autism spectrum disorder," Neuroscience, 324: 131-139.
Lin et al., "Twelve Week Storage Trial of Microbial Viability in Lyophilized and Frozen Fecal Microbiota Preparations," Poster Presentation—Digestive Disease Week 2015, Washington, D.C. USA.
Liu X et al. (2015). "Modulation of Gut Microbiota-Brain Axis by Probiotics, Prebiotics, and Diet," J. Agric. Food Chem., 63(36):7885-7895.
Longstreth, "Irritable bowel syndrome: A multibillion-dollar problem," Gastroenterology, 109(6):2029-2031 (1995).
Lonsdale et al.; "Treatment of autism spectrum children with thiamine tetrahydrofurfuryl disulfide: A pilot study"; Neuroendocrinology Letters, 2002, vol. 23, pp. 303-308.
Loo et al., "A predominantly clonal multiinstitutional outbreak of Clostridium difficile-associated diarrhea with high morbidity and mortality," N Engl J Med, 353(23):2442-9 (2005).
Loo et al., "Host and pathogen factors for Clostridium difficile infection and colonization," N Engl J Med, 365 (18):1693-703 (2011).
Louie et al., "Fidaxomicin versus vancomycin for Clostridium difficile infection," N. Engl. J. Med., 364(5):422-431 (2011).
Louie et al., "Home-based fecal flora infusion to arrest multiply-recurrent C. difficile infection," ICAAC/IDSA Conference, Abstract #K-4201 (2008).
Louis et al., "Diversity, metabolism and microbial ecology of butyrate-producing bacteria from the human large intestine," FEMS Microbiology Letters, 294:1-8 (2009).
Lu, "Taboo transplant: How new poo defeats superbugs," Science News, 1:90-91 (2011).
Ludwig et al., "Taxonomic outline of the phylum Firmicutes," Bergey's Manual of Systematic Bacteriology, 3:15-17 (2009).
Lund-Tonnesen et al., "Clostridium difficile-associated diarrhea treated with homologous faeces," Tidsskr Nor Lageforen, 118:1027-1030 (1998).
Lund-Tonnesen et al., "Clostridium difficile-associated diarrhea treated with homologous feces," Tidsskr Nor Lageforen, 118:1027-1030 (1998).
MacConnachie et al., "Faecal transplant for recurrent Clostridium difficile-associated diarrhoea: a UK case series," QJM, 102(11):781-784 (2009).
MacDonald et al., "Formation of Ursodeoxycholic Acid from Chenodeoxycholic Acid by a 7β-Hydroxysteroid Dehydrogenase-Elaborating Eubacterium aerofaciens Strain Cocultured with 7α-Hydroxysteroid Dehydrogenase-Elaborating Organisms," Applied and Environmental Microbiology, 44(5):1187-1195 (1982).
MacFabe et al.; "Short-chain fatty acid fermentation products of the gut microbiome: implications in autism spectrum disorders"; Microbial Ecology in Health & Disease, 2012, vol. 23: 19260 (24 pages).
Macpherson et al., "Induction of Protective IgA by Intestinal Dendritic Cells Carrying Commensal Bacteria," Science, 303:1662-1665 (2004).
Madsen, "The use of probiotics in gastrointestinal disease," Can J Gastroenterol, 15(12):817-22 (2001).
Magistris et al.; "Alterations of the Intestinal Barrier in Patients with Autism Spectrum Disorders and in Their First Degree Relatives"; Gastroenterology, 2010, vol. 51, No. 4, pp. 418-424.

(56) References Cited

OTHER PUBLICATIONS

Maizels et al., "Regulatory T cells in Infection," Advances in Immunology, Chapter 3, 112:73-136 (2011).
Mangiola F et al. (2016). "Gut microbiota in autism and mood disorders," World J Gastroenterol., 22(1): 361-368.
Marchesi et al., "The normal intestinal microbiota," Curr. Opin. Infect. Dis., 20(5):508-513 (2007).
Pépin et al., "Clostridium difficile-associated diarrhea in a region of Quebec from 1991 to 2003: a changing pattern of disease severity," CMAJ, 171(5):466-472 (2004).
Pépin et al., "Emergence of Fluoroquinolones as the Predominant Risk Factor for Clostridium difficile-Associated Diarrhea: A Cohort Study During an Epidemic in Quebec," Clin Infect Dis., 41(9):1254-1260 (2005).
Pépin et al., "Management and Outcomes of a First Recurrence of Clostridium difficile-Associated Disease in Quebec, Canada," Clin. Infect. Dis., 42:758-764 (2006).
Persky et al., "Treatment of recurrent Clostridium difficile-associated diarrhea by administration of donated stool directly through a colonoscope," Am J Gastroenterol., 95(11):3283-3285 (2000).
Petrof E (2013). "Microbial ecosystems therapeutics: a new paradigm in medicine?" Beneficial Microbes, 4(1): 53-65.
Petrof E et al. (2014). "From Stool Transplants to Next-Generation Microbiota Therapeutics," Gastroenterology, 146(6): 1573-1582.
Petrof et al., "Stool substitute transplant therapy for the eradication of Clostridium difficile infection: 'RePOOPulating' the gut," Microbiome, 1:3 (2013).
Petrof, "Harnessing the healthy gut microbiota to cure patients with recurrent C. difficile infection," U.S. National Institutes of Health, Clinical Study No. NCT01372943, pp. 1-2, last updated Nov. 6, 2013, Web, May 22, 2014 <http://clinicaltrials.gov/ct2/show/NCT01372943>.
Pillai et al., "Probiotics for treatment of Clostridium difficile-associated colitis in adults (Review)," Cochrane Database Syst Rev., (1):CD004611 (2008).
Porter, "Coating of pharmaceutical dosage forms," In D.B. Troy (Ed.), Remington: The Science and Practice of Pharmacy, Chapter 46, pp. 929-938 (2005).
Prakash et al., "Colon-targeted delivery of live bacterial cell biotherapeutics including microencapsulated live bacterial cells," Biologies: Targets & Therapy, 2(3):355-378 (2008).
Prevention of Sudden Infant Death Syndrome, Healthtouch.com, Thomson Micromedex, pp. 1-4, n.d., Web, Nov. 23, 2005.
Qin et al.; "A human gut microbial gene catalogue established by metagenomic sequencing"; Nature, Mar. 4, 2010; vol. 464, pp. 59-67.
Qiu et al., "Faecalibacterium prausnitzii upregulates regulatory T cells and anti-inflammatory cytokines in treating TNBS-induced colitis," Journal of Crohn's and Colitis, 7:e558-e568 (2013).
Rabeneck et al., "Bleeding and perforation after outpatient colonoscopy and their risk factors in usual clinical practice," Gastroenterology, 135(6):1899-1906 (2008).
Rager et al., "Evaluation of rumen transfaunation after surgical correction of left-sided displacement of the abomasum in cows," J. Am. Vet. Med. Assoc., 225(6):915-920 (2004).
Ramesh et al., "Prevention of Clostridium difficile-induced ileocecitis with Bacteriophage," Anaerobe, 5:69-78 (1999).
Rao et al., "Evaluation of gastrointestinal transit in clinical practice: position paper of the American and European Neurogastroenterology and Motility Societies," Neurogastroenterol. Motil., 23(1):8-23 (2011).
Rea et al., "Gut solutions to a gut problem: bacteriocins, probiotics and bacteriophage for control of Clostridium difficile infection," Journal of Medical Microbiology, 62:1369-1378 (2013).
Reddy B (2015). "Autism and our intestinal microbiota," Journal of Mol. Microbio. and Biotech. 25(1): 51.
Redelings et al., "Increase in Clostridium difficile-related mortality rates, United States, 1999-2004," Emerg Infect Dis., 13(9):1417-1419 (2007).
Response to Office Action filed Feb. 25, 2014, in European Patent Application No. 11 728 077.6.
Response to Office Action filed Jan. 28, 2015, in European Patent Application No. 11 728 077.6.
Response to Office Action filed Nov. 18, 2015, in European Patent Application No. 11 728 077.6.
Rex et al., "American College of Gastroenterology guidelines for colorectal cancer screening 2008," Am. J. Gastroenterol., 104(3):739-750 (2009).
Ricciardi et al., "Increasing prevalence and severity of Clostridium difficile colitis in hospitalized patients in the United States," Arch Surg., 142(7):624-631 (2007).
Roberts, Generation and Development Microbial Drug Products, CSO Vedanta Biosciences, 1st Microbiome Drug Development Summit, pp. 1-17 (2016).
Robertson et al.; "Intestinal Permeability and Glucagon-like peptide-2 in Children with Autism: A Controlled Pilot Study"; Journal of Autism Development Disorder; Feb. 28, 2008; vol. 38, pp. 1066-1071.
Robinson et al.; "Characterization of the Cecal Bacteria of Normal Pigs"; Applied and Environmental Microbiology, Apr. 1981, vol. 41, No. 4, pp. 950-955.
Rodemann et al., "Incidence of Clostridium difficile infection in inflammatory bowel disease," Clin Gastroenterol Hepatol., 5(3):339-344 (2007).
Rohlke et al., "Fecal flora reconstitution for recurrent Clostridium difficile infection: results and methodology," J Clin Gastroenterol., 44(8):567-570 (2010).
Roid et al., Leiter International Performance Scale-Revised, Stoelting (1997).
Rolfe et al., "Bacterial interference between Clostridium difficile and normal fecal flora," J Infect Dis., 143(3):470-475 (1981).
Rosenfeld C (2015). "Microbiome Disturbances and Autism Spectrum Disorders," Drug Metabolism and Disposition, 43 (10): 1557.
Rossen et al., "Findings From a Randomized Controlled Trial of Fecal Transplantation for Patients with Ulcerative Colitis," Gastroenterology, 149(1):110-8 (2015).
Round et al., "The gut microbiota shapes intestinal immune responses during health and disease," Nat. Rev. Immunol., 9(5):313-323 (2009).
Round et al.; "The Toll-like receptor pathway establishes commensal gut colonization"; Science; May 20, 2011; vol. 332(6032), pp. 974-977.
Rupnik et al., "Clostridium difficile infection: new developments in epidemiology and pathogenesis," Nat. Rev. Microbiol., 7(7):526-536 (2009).
Russell et al., "Fecal bacteriotherapy for relapsing Clostridium difficile infection in a child: a proposed treatment protocol," Pediatrics, 126(1):e239-42 (2010).
Salazar et al.; "Exopolysaccharides Produced by Intestinal Bifidobacterium Strains Act as Fermentable Substrates for Human Intestinal Bacteria"; Applied Environmental Microbiology, 2008, vol. 74, No. 15, pp. 4737-4745.
Sambol et al., "Colonization for the prevention of Clostridium difficile disease in hamsters," J. Infect. Dis., 186 (12):1781-1789 (2002).
Sanchez et al., "The Role of Natural Regulatory T cells in Infection," Immunol Res., 49(0):124-134 (2011).
Sandler et al., "Possible Gut-Brain Interaction Contributing to Delayed Onset Autism Symptomatology," Fourth Int. Symp. Brain-Gut Interactions, Blackwell Science Ltd., 10(4):33 (1998).
Sandler et al.; "Short-Term Benefit From Oral Vancomycin Treatment of Regressive-Onset Autism"; Journal of Child Neurology; Jul. 2000; vol. 15, No. 7, pp. 429-435.
Sartor, "Therapeutic correction of bacterial dysbiosis discovered by molecular techniques," PNAS, 105 (43):16413-16414 (2008).
Schauer et al.; "Attaching and Effacing Locus of a Citrobacterfreundii Biotype That Causes Transmissible Murine Colonic Hyperplasia"; Infectious Immunology; Jun. 1993; vol. 61, No. 6, pp. 2486-2492.
Schiller, "Review article, the therapy of constipation," Ailment Pharmacol. Ther., 15:749-763 (2001).
Schloss et al.; "Introducing mothur: Open-Source, Platform-Independent, Community-Supported Software for Describing and

(56) References Cited

OTHER PUBLICATIONS

Comparing Microbial Communities"; Applied and Environmental Microbiology; Dec. 2009; vol. 75, No. 23, pp. 7537-7541.
Schneider et al.; "Oral Human Immunoglobulin for Children with Autism and Gastrointestinal Dysfunction: A Prospective, Open-Label Study"; Journal of Autism Development Disorder; Jul. 15, 2006; vol. 36, pp. 1053-1064.
Schopler et al., Childhood autism rating scale-second edition (CARS2), Western Psychological Service, 4-5, 93 (2010).
International Search Report dated Jul. 29, 2014, in International Application No. PCT/AU2014/000478, 7 pgs.
International Search Report dated Sep. 22, 2017, in International Application No. PCT/US2017/040591, 12 pgs.
Irrgang et al., "The historical Development of Mutaflor therapy," Ardeypharm GmbH, pp. 1-38 (1988) <http://www.ardeypharm.de/pdfs/en/mutaflor_historical_e.pdf?>.
Irritable Bowel Syndrome (IBS), Health A to Z, InteliHealth, pp. 1-4, n.d., Web, Oct. 23, 2005 <http://www.intelihealth.com>.
Issa et al., "Clostridium difficile and Inflammatory Bowel Disease," Inflamm Bowel Dis., 14(10): 1432-1442 (2008).
Issa et al., "Impact of Clostridium difficile on inflammatory bowel disease," Clin. Gastroenterol. Hepatol., 5(3):345-351 (2007).
Itoh et al., "Characterization of Clostridia isolated from faeces of limited flora mice and their effect on caecal size when associated with germ-free mice," Laboratory Animals, 19:111-118 (1985).
Itoh et al., "Intestinal bacteria antagonistic to Clostridium difficile in mice," Laboratory Animals, 21:20-25 (1987).
Ivanov et al., "Specific Microbiota Direct the Differentiation of IL-17-Producing T-Helper Cells in the Mucosa of the Small Intestine," Cell Host & Microbe, 4:337-349 (2008).
Ivanov et al.; "Induction of intestinal Th17 cells by segmented filamentous bacteria"; Cell, 2009, vol. 139., No. 3, pp. 185-498.
Jacob et al., "Single Delivery of High-Diversity Fecal Microbiota Preparation by Colonoscopy Is Safe and Effective in Increasing Microbial Diversity in Active Ulcerative Colitis," Inflamm Bowel Dis., 0(0):1-9 (2017).
James et al.; "Metabolic biomarkers of increased oxidative stress and impaired methylation capacity in children with autism"; Journal of Clinical Nutrition, 2004, vol. 80, pp. 1611-1617.
Janeway et al., "Adaptive Immunity to Infection," Immunobiology, 6th Edition, Chapter 10, pp. 414 (2005).
Janeway, Jr. et al., "Autoimmune responses are directed against self antigens," Immunobiology: The Immune System in Health and Disease, 5th Edition, pp. 1-4 (2001).
Jarvis et al., "National point prevalence of Clostridium difficile in US health care facility inpatients, 2008," Am. J. Infect. Control, 37:263-270 (2009).
Jia et al.; "Gut microbiota: a potential new territory for drug targeting"; Nature Reviews—Drug Discovery, 2008; vol. 7, pp. 123-129.
Johnson et al., "Interruption of Recurrent Clostridium difficile-Associated Diarrhea Episodes by Serial Therapy with Vancomycin and Rifaximin," Clin. Infect. Dis., 44(6):846-848 (2007).
Johnson et al., "Rifaximin Redux: Treatment of recurrent Clostridium difficile infections with Rifaximin immediately post-vancomycin treatment," Anaerobe, 15(6):290-291 (2009).
Kageyama et al., "Emendation of genus *Collinsella* and proposal of *Collinsella stercoris* sp. nov. and *Collinsella intestinalis* sp. nov.," International Journal of Systematic and Evolutionary Microbiology, 50:1767-1774 (2000).
Kageyama et al., "Phylogenetic and phenotypic evidence for the transfer of Eubacterium aerofaciens to the genus *Collinsella* as *Collinsella aerofaciens* gen. nov., comb. nov.," International Journal of Systematic Bacteriology, 49:557-565 (1999).
Kakihana et al., "Fecal microbiota transplantation for patients with steroid-resistant acute graft-versus-host disease of the gut," Blood, 128(16):2083-2088 (2016).
Kamboj et al., "Relapse versus reinfection: surveillance of Clostridium difficile infection," Clin Infect Dis., 53 (10):1003-1006 (2011).

Kang et al., "Microbiota Transfer Therapy alters gut ecosystem and improves gastrointestinal and autism symptoms: an open-label study," Microbiome, 5:10, 16 pages (2017).
Kang et al., "Reduced Incidence of Prevotella and Other Fermenters in Intestinal Microflora of Autistic Children," PLOS One, 8(7):e68322, 14 pages (2013).
Kantarcioglu A et al. (2016). "Microbiota-Gut-Brain Axis: Yeast Species Isolated from Stool Samples of Children with Suspected or Diagnosed Autism Spectrum Disorders and In Vitro Susceptibility Against Nystatin and Fluconazole," Mycopathologia, 181(1):1-7.
Kaper et al.; "Pathogenic *Escherichia coli*"; Nature Reviews—Microbiology, Feb. 2004; vol. 2, pp. 123-140.
Karas et al., "A review of mortality due to Clostridium difficile infection," J Infect., 61(1):1-8 (2010).
Kassam et al., "Fecal transplant via retention enema for refractory or recurrent Clostridium difficile infection," Arch Intern Med., 172(2):191-193 (2012).
Kelly et al., "Clostridium difficile colitis," N. Engl. J. Med., 330(4):257-62 (1994).
Kelly et al., "Clostridium difficile—more difficult than ever," N. Engl. J. Med., 359(18):1932-1940 (2008).
Kelly et al., "Commensal gut bacteria: mechanisms of immune modulation," Trends in Immunology, 26(6):326-333 (2005).
Kelly et al., "Fecal Microbiota Transplant for Treatment of Clostridium difficile Infection in Immunocompromised Patients," Am J Gastroenterol, 109:1065-1071 (2014).
Kelly et al., "Fecal microbiota transplantation for relapsing Clostridium difficile infection in 26 patients: methodology and results," J. Clin. Gastroenterol., 46(2):145-149 (2012).
Keynan et al., "The Role of Regulatory T Cells in Chronic and Acute Viral Infections," Clinical Infectious Diseases, 46:1046-1052 (2008).
Khanna et al., "A Novel Microbiome Therapeutic Increases Gut Microbial Diversity and Prevents Recurrent Clostridium difficile Infection," The Journal of Infectious Diseases, 214:173-81 (2016).
Khanna et al., "The epidemiology of community-acquired Clostridium difficile infection: a population-based study," Am J Gastroenterol., 107(1):89-95 (2012).
Khanna et al., "The growing incidence and severity of Clostridium difficile infection in inpatient and outpatient settings," Expert Rev Gastroenterol Hepatol., 4(4):409-16 (2010).
Kharidia et al., "The Activity of a Small Lytic Peptide PTP-7 on *Staphylococcus aureus* Biofilms," J. Microbiol., 49 (4):663-668 (2011).
Khoruts A et al. (2014). "Emergence of fecal microbiota transplantation as an approach to repair disrupted microbial gut ecology," Immunol Lett. 162(2A):77-81.
Khoruts et al., "Changes in the composition of the human fecal microbiome after bacteriotherapy for recurrent Clostridium difficile-associated diarrhea," J. Clin. Gastroenterol., 44(5):354-360 (2010).
Khoruts et al., "Therapeutic transplantation of the distal gut microbiota," Mucosal Immunol., 4(1):4-7 (2011).
Kim et al., "Effect of Rifampin on the Plasma Concentration and the Clinical Effect of Haloperidol Concomitantly Administered to Schizophrenic Patients," Journal of Clinical Psychopharmacology, 16(3):247-252 (1996).
Kim et al., "In Vitro Culture Conditions for Maintaining a Complex Population of Human Gastrointestinal Tract Microbiota," Journal of Biomedicine and Biotechnology, 2011(Article ID 838040):1-10 (2011) <http://www.hindawi.com/journals/bmri/2011/838040/>.
Kitajka et al.; "Effects of dietary omega-3 polyunsaturated fatty acids on brain gene expression"; PNAS, Jul. 27, 2004; vol. 101, No. 30, pp. 10931-10936.
Klaenhammer, "Bacteriocins of lactic acid bacteria," Biochimie, 70:337-49 (1988).
Kleiman et al., "Comparison of two coprological methods for the veterinary diagnosis of fasciolosis," Arquivo Brasileiro de Medicina Veterinária e Zootécnica, 55(2):181-185 (2005).
Kobashi et al., "Metabolism of Sennosides by Human Intestinal Bacteria," Journal of Medicinal Plant Research, 40 (3):225-236 (1980).
Koch, "What size should a bacterium be? A question of scale," Annu. Rev. Microbiol., 50:317-48 (1996).

(56) References Cited

OTHER PUBLICATIONS

Kostic et al.; "Genomic analysis identifies association of Fusobacterium with colorectal carcinoma"; Genome Research 2011, vol. 22, pp. 292-298.
Krogius-Kurikka et al., "Sequence analysis of percent G+C fraction libraries of human faecal bacterial DNA reveals a high number of Antinobacteria," BMC Microbiology, 9(68):1-13 (2009).
Balfour Sartor R (2004). "Therapeutic manipulation of the enteric microflora in inflammatory bowel diseases: antibiotics, probiotics, and prebiotics," Gastroenterology, 126(6): 1620-1633.
Bartlett et al., "Clinical recognition and diagnosis of Clostridium difficile infection," Clin Infect Dis., 46(Suppl 1):S12-S18 (2008).
Bartlett, "Clostridium difficile-associated Enteric Disease," Curr Infect Dis Rep., 4(6):477-483 (2002).
Baumgart D et al. (2007). "Inflammatory bowel disease: cause and immunobiology," The Lancet, 369(9573): 1627-1640.
Belkaid et al., "Natural regulatory T cells in infectious disease," Nature Immunology, 6(4):353-360 (2005).
Bengmark et al., "Bioecological control of inflammatory bowel disease," Clinical Nutrition, 26(2):169-181 (2007).
Bennet et al., "Treatment of ulcerative colitis by implantation of normal colonic flora," Lancet, 333(8630):164 (1989).
Benson et al., "Changing epidemiology of Clostridium difficile-associated disease in children," Infect Control Hosp Epidemiol., 28(11):1233-1235 (2007).
Berg; "The indigenous gastrointestinal microflora"; Trends Microbiol., 1996, vol. 4, pp. 430-435.
Blaser et al., "What are the consequences of the disappearing human microbiota?" Nat. Rev. Microbiol., 7(12):887-894 (2009).
Blaser, "Who are we? Indigenous microbes and the ecology of human diseases," EMBO Rep, 7(10):956-960 (2006).
Bolte, "Autism and Clostridium tetani," Medical Hypotheses, 51(2):133-144 (1998).
Bolte, "Therapies for Gastrointestinal and Neurological Disorders." U.S. Appl. No. 60/214,813, filed Jun. 28, 2000.
Bordello; "Clostridial Disease of the Gut"; Clinical Infectious Diseases; 1995; vol. 20, pp. S242-S250.
Borody et al., "Anti-MAP Rescues Anti-TNF Failures for Over 4 Years," Gastroenterol, 136(5)Suppl 1:A-681 (2009).
Borody et al., "Anti-MAP Therapy for Pediatric Crohn's Disease," Am J Gastroenterol, 108(Suppl 1):S516 (2013).
Borody et al., "Anti-MAP Therapy in the Treatment of Active Crohn's Disease," J Gastroenterol & Hepatol, 20 (Suppl):A2 (2005).
Borody et al., "Anti-mycobacterial therapy in Crohn's disease heals mucosa with longitudinal scars," Digestive & Liver Disease, 39(5):438-444 (2007).
Borody et al., "Anti-*Mycobacterium avium* SS Paratuberculosis (MAP) Therapy and Fistula Closure in Patients with Severe Crohn's Disease," Am J Gast, A101:S440 (2006).
Borody et al., "Bacteriotherapy in Chronic Fatigue Syndrome (CFS): A retrospective review," Am J Gastro, 107 (S1):A1481 (2012).
Borody et al., "Bacteriotherapy Using Fecal Flora: toying with human motions" J. Clin. Gastroenterol., 38(6):475-483 (2004).
Borody et al., "Bowel-flora alteration: a potential cure for inflammatory bowel disease and irritable bowel syndrome?" Med. J. Aust., 150:604 (1989).
Borody et al., "Changes in Crohn's Disease Activity Index and C-Reactive Protein Levels During Anti-MAP Therapy," Am J Gastro, 104(S3):A1293 (2009).
Borody et al., "Clostridium difficile Complicating Inflammatory Bowel Disease: Pre- and Post-Treatment Findings," Gastroenterol, 134(4)Suppl 1:A-361 (2008).
Borody et al., "Could fecal microbiota transplantation cure all Clostridium difficile infections?," Future Microbiol, 9:1-3 (2014).
Borody et al., "Entamoeba histolytica: another cause of Crohn's Disease," Am J Gastro, 104(S3):A990 (2009).
Borody et al., "Faecal bacteriotherapy (FB) for chronic C. difficile (Cd) syndromes," J Gastroenterol Hepatol, 18 (Suppl.):B8 (Abstract) (2003).
Borody et al., "Fecal bacteriotherapy in the treatment of recurrent C. difficile infection," UpToDate, pp. 1-6 (2006).
Borody et al., "Fecal Microbiota Transplantation (FMT) in Multiple Sclerosis (MS)," Am J Gastro, 106(S2):A942 (2011).
Borody et al., "Fecal microbiota transplantation and emerging applications," Nat. Rev. Gastroenterol. Hepatol., 9 (2):88-96 (2011).
Borody et al., "Fecal microbiota transplantation for Clostridium difficile infection: A surgeon's perspective" Seminars in Colon and Rectal Surgery, 25:163-166 (2014).
Borody et al., "Fecal microbiota transplantation in gastrointestinal diseases—What practicing physicians should know," Polish Archives of Internal Medicine, 125(11):852-858 (2015).
Borody et al., "Fecal microbiota transplantation in the treatment of recurrent Clostridium difficile infection," UpToDate, pp. 1-4, (2015).
Borody et al., "Fecal Microbiota Transplantation in Ulcerative Colitis: Review of 24 Years Experience," Am J Gastro, 107(Supp 1):A1644 (2012).
Borody et al., "Fecal microbiota transplantation: a new standard treatment option for Clostridium difficile infection," Expert Rev Anti Infect Ther., 11(5):447-449 (2013).
Borody et al., "Fecal microbiota transplantation: current status and future directions," Expert Review of Gastroenterology & Hepatology, 5(6):653-655 (2011).
Borody et al., "Fecal Microbiota Transplantation: Expanding Horizons for Clostridium difficile Infections and Beyond," Antibiotics, 4:254-266 (2015).
Borody et al., "Fecal Microbiota Transplantation: Indications, Methods, Evidence, and Future Directions," Curr Gastroenterol Rep, 15:337-344 (2013).
Borody et al., "Fecal Microbiota Transplantation: Techniques, Applications, and Issues," Gastroenterol Clin North Am, 41:781-803 (2012).
Borody et al., "Irritable Bowel Syndrome and Dientamoeba Fragilis," ASM Sydney National Conference, pp. 4-5 (2002).
Borody et al., "Is Crohn's Disease Ready for Fecal Microbiota Transplantation?," J Clin Gastroenterol, 48(7):582-583 (2014).
Borody et al., "Myoclonus-dystonia affected by GI Microbiota?," Am J Gastro, 106(S2):A940 (2011).
Borody et al., "Novel appearance of healing mucosa following anti-*Mycobacterium avium* paratuberculosis therapy for Crohn's disease," J Gastroenterol Hepatol, 19(Suppl):A210 (2004).
Borody et al., "Reversal of Inflammatory Bowel Disease (IBD) with Recurrent Faecal Microbiota Transplants (FMT)," Am J Gastro, 106(S2):A979 (2011).
Borody et al., "Severe recurrent Crohn's Disease of ileocolonic anastomosis and antimicrobial (anti-mycobacterial therapy)," Gut, 55:1211 (2006).
Borody et al., "The GI Microbiome and its Role in Chronic Fatigue Syndrome: a Summary of Bacteriotherapy," ACNEM Journal, 31(3):3-8 (2012).
Borody et al., "Therapeutic faecal microbiota transplantation: current status and future developments," Curr Opin Gastroenterol, 30:97-105 (2014).
Borody et al., "Treatment of chronic constipation and colitis using human probiotic infusions," Proceedings of Prebiotics and Probiotics and the New Foods Conference, 2-4:228 Abstract (2001).
Borody et al., "Treatment of First-time Clostridium difficile Infection with Fecal Microbiota Transplantation," Poster Presentation, 2015 ACG Annual Scientific Meeting, Honolulu, Hawaii, USA (2015).
Borody et al., "Treatment of Severe Constipation Improves Parkinson's Disease (PD) Symptoms," Am J Gastro, 104 (S3):A999 (2009).
Vulevic et al., "Modulation of the fecal microflora profile and immune function by a novel trans-galactooligosaccharide mixture (B-GOS) in healthy elderly volunteers," Am J Clin Nutr, 88:1438-46 (2008).
Wachsmann et al., "Characterization of an Orotic Acid Fermenting Bacterium, *Zymobacterium oroticum*, nov. gen., nov. spec.," Journal of Bacteriology, 68(4):400-404 (1954).
Walter et al., "Host-microbial symbiosis in the vertebrate gastrointestinal tract and the Lactobacillus reuteri paradigm," PNAS USA, 108(Suppl 1):4645-4652 (2011).

(56) References Cited

OTHER PUBLICATIONS

Wang et al.; "Low Relative Abundances of the Mucolytic Bacterium Akkermansia muciniphila and *Bifidobacterium* spp. in Feces of Children with Autism"; Applied Environmental Microbiology; Sep. 2011; vol. 77, No. 18, pp. 5718-6721.
Warnock et al.; "A roadmap for biomarker qualification"; Nature; May 2010; vol. 28, No. 5, pp. 444-445.
Warny et al., "Toxin production by an emerging strain of Clostridium difficile associated with outbreaks of severe disease in North America and Europe," Lancet, 366(9491):1079-84 (2005).
Warren et al., "*Clostridium aldenense* sp. nov. and *Clostridium citroniae* sp. nov. Isolated from Human Clinical Infections," Journal of Clinical Microbiology, 44(7):2416-2422 (2006).
Wasfy et al., "Comparison of Preservation Media for Storage of Stool Samples," Journal of Clinical Microbiology, 33 (8):2176-2178 (1995).
Weingarden et al., "Dynamic changes in short- and long-term bacterial composition following fecal microbiota transplantation for recurrent Clostridium difficile infection," Microbiome, 3(10), 8 pages (2015).
Weissman et al., "Stool Transplants: Ready for Prime Time?," Current Gastroenterology Reports, 14:313-316(2012).
Wells et al., "Clostridia: Sporeforming Anaerobic Bacilli," Medical Microbiology—NCBI Bookshelf, 4th Edition, Chapter 18, pp. 1-20 (1996) <https://www.ncbi.nlm.nih.gov/books/NBK8219/?report=printable>.
Wenisch et al., "Comparison of Vancomycin, Teicoplanin, Metronidazole, and Fusidic Acid for the Treatment of Clostridium difficile-Associated Diarrhea," Clin Infect Dis., 22(5):813-818 (1996).
West, C., et al., "The gut microbiota and inflammatory noncommunicable diseases: Associations and potentials for gut microbiota therapies" Journal of Allergy and Clinical Immunology, vol. 135, Issue 1, Jan. 2015, pp. 3-13.
Wettstein et al., "Fecal Bacteriotherapy—An effective Treatment for Relapsing Symptomatic Clostridium difficile Infection," Abstract, 15th United European Gastroenterology Week (UEGW) Poster presentations, United European Gastroenterology Federation, France, A303 (2007).
Wettstein et al., "Skewered diverticulum: another cause of abdominal pain," Internal Med J, 31(8):495-496 (2001).
Wikoff et al., "Metabolomics analysis reveals large effects of gut microflora on mammalian blood metabolites," PNAS, 106(10):3698-3703 (2009).
Williams et al.; "Impaired Carbohydrate Digestion and Transport and Mucosal Dysbiosis in the Intestines of Children with Autism and Gastrointestinal Disturbances"; Sep. 2011; Plos One, vol. 6, Issue 9, e24585 (21 pages).
Willing et al.; "Shifting the balance: antibiotic effects on host-microbiota mutualism"; Nature Review of Microbiology; Apr. 2011; vol. 9, pp. 233-243.
Wilson et al., "Human Colonic Biota Studied by Ribosomal DNA Sequence Analysis," Appl. Environ. Microbiol., 62 (7):2273-2278 (1996).
Wolcott et al.; "Evaluation of the bacterial diversity among and within individual venous leg ulcers using bacterial tag-encoded FLX and Titanium aplicon pyrosequencing and metagenomic approaches"; Oct. 27, 2009; BMC Microbiology; vol. 9:226 (11 pages).
Wu et al.; "Focused Evolution of HIV-1 Neutralizing Antibodies Revealed by Structures and Deep Sequencing"; Science, Sep. 16, 2011; vol. 333, pp. 1593-1602.
Yarandi S et al. (2016). "Modulatory Effects of Gut Microbiota on the Central Nervous System: How Gut Could Play a Role in Neuropsychiatric Health and Diseases," J Neurogastroenterol Motil., 22(2): 201-212.
Yoon et al., "Treatment of Refractory/Recurrent C. difficile-associated Disease by Donated Stool Transplanted Via Colonoscopy: A Case Series of 12 patients," J Clin Gastroenterol., 44(8):562-566 (2010).
You et al., "Successful treatment of fulminant Clostridium difficile infection with fecal bacteriotherapy," Ann Intern. Med., 148(8):632-633 (2008).
Yue et al., "Similarity Measure Based on Species Proportions," Commun. Stat. Theor. Methods, 34(11):2123-2131 (2005).
Zar et al., "A Comparison of Vancomycin and Metronidazole for the Treatment of Clostridium difficile-Associated Diarrhea, Stratified by Disease Severity," Clin Infect Dis., 45(3):302-307 (2007).
Zhang et al.; "Human gut microbiota in obesity and after gastric bypass"; PNAS, Feb. 17, 2009; vol. 106, No. 7, pp. 2365-2370.
Zhou et al., "Total fecal microbiota transplantation alleviates high-fat diet-induced steatohepatitis in mice via beneficial regulation of gut microbiota," Scientific Reports (Nature), 7(1529):1-11 (2017).
Zhu et al.; "Altered glutathione homeostasis in animals prenatally exposed to lipopolysaccharide"; Neurochemistry International, Mar. 2007, 50(4), 671-680 (21 pages).
Zilberberg et al., "Clostridium difficile Infections among Hospitalized Children, United States, 1997-2006," Emerg. Infect. Dis, 16(4):604-609 (2010).
Zilberberg et al., "Clostridium difficile-related Hospitalizations among US Adults, 2006," Emerg. Infect. Dis, 15 (1):122-124 (2009).
Zilberberg et al., "Increase in Adult Clostridium difficile-related Hospitalizations and Case-Fatality Rate, United States, 2000-2005," Emerg. Infect. Dis, 14(6):929-931 (2008).
Zilberberg et al., "Increase in Clostridium difficile-related Hospitalizations Among Infants in the United States, 2000-2005," Pediatr Infect Dis J., 27(12):1111-1113.
Zoppi et al., "Oral Bacteriotherapy in Clinical Practice," Eur J. Pediatr, 139(1):18-21 (1982).
Zoppi et al., "The Intestinal Ecosystem in Chronic Functional Constipation," ACTA Paediatr, Scandinavian University Press, p. 836-841 (1998).

\* cited by examiner

MICROBIOME MARKERS AND THERAPIES FOR AUTISM SPECTRUM DISORDERS

CROSS-REFERENCE TO RELATED APPLICATION

This application is continuation of U.S. application Ser. No. 16/118,061 filed Aug. 30, 2018 (now U.S. Pat. No. 11,542,560 issued Jan. 3, 2023) that is a continuation of U.S. application Ser. No. 15/629,962 filed Jun. 22, 2017 that is a divisional of U.S. application Ser. No. 14/403,425 filed Nov. 24, 2014 (now U.S. Pat. No. 9,719,144, issued Aug. 1, 2017), which is a U.S. national stage of International Application No. PCT/US2013/032668, filed Mar. 15, 2013, which claims the benefit of U.S. Provisional Patent Application 61/651,846, filed on May 25, 2012, which is hereby incorporated by reference in their entireties.

INCORPORATION OF SEQUENCE LISTING

The present application contains a Sequence Listing which has been submitted in .XML format via PatentCenter and is hereby incorporated herein by reference in its entirety. Said WIPO Sequence Listing was created on Mar. 28, 2023 named 055743-742813.xml and is 3.9 kilobytes in size.

FIELD OF THE INVENTION

The present invention relates to microbiology, neurology, and nutritional physiology.

BACKGROUND OF THE INVENTION

The human gut hosts millions of bacteria, which harmoniously balance the immune system, help digest food, produce vitamins, and promote gastrointestinal (GI) motility. Loss of homeostasis in the gut may contribute to an imbalance associated with disease states, such as immune and neurological disorders, and cause GI problems, which can exacerbate other disorders or symptoms. For example, Autism Spectrum Disorders (ASDs) are complex neurobiological disorders whose chief manifestations are qualitative impairment in social interaction and communication and restricted repetitive and stereotyped patterns of behavior, interests, and activities. There has been a world-wide increase in the diagnosis of ASD, which has reached epidemic level. ASD subjects and their families face difficulties in treatment because ASD does not share a common etiology. Both genetic and environmental factors are important in the etiology of autism, with a recent large twin concordance study suggesting that environmental factors are at least as important, if not more important, than genetic ones. A potentially important environmental factor is abnormal intestinal flora that often interacts with other factors such as intestinal permeability and transport of toxic substances. Hence, there remains a need for understanding the role of the microbiome in the healthy gut versus the unhealthy gut, and, in particular in the context of ASD subjects.

SUMMARY OF THE INVENTION

In at least one aspect, an assay includes subjecting nucleic acid extracted from a test sample of a human subject to a genotyping assay that detects at least one of *Prevotella, Coprococcus, Prevotellaceae*, or *Veillonellaceae* bacteria, the test sample including microbiota from a gut of the subject; determining a relative abundance of the at least one of *Prevotella, Coprococcus, Prevotellaceae*, or *Veillonellaceae* bacteria that is below a predetermined abundance; and selecting, when the relative abundance is below the predetermined abundance, a treatment regimen that comprises at least one of modifying microbiota of the gut of the subject using at least one of a prebiotic, probiotic, or pharmaceutical, or applying a therapeutic regimen for treating autism spectrum disorders.

In at least one aspect, an assay includes subjecting protein extracted from a test sample of a human subject to a protein assay that determines at least one protein indicative of at least one of *Prevotella, Coprococcus, Prevotellaceae*, or *Veillonellaceae* bacteria, the test sample including microbiota from a gut of the subject, determining a relative abundance of the at least one of *Prevotella, Coprococcus, Prevotellaceae*, or *Veillonellaceae* bacteria that is below a predetermined abundance, and selecting, when the relative abundance is below the predetermined abundance, a treatment regimen that comprises at least one of modifying microbiota of a gastrointestinal tract of the subject, or applying a therapeutic regimen for treating autism spectrum disorders.

In at least one aspect, a method of selecting a treatment regimen for a human subject, includes subjecting a test sample from the human subject, including microbiota from a gut of the subject, to at least one of nucleic acid extraction, or protein extraction; detecting, using at least one of the extracted nucleic acid or protein, a relative abundance of at least one of *Prevotella, Coprococcus, Prevotellaceae*, or *Veillonellaceae* bacteria in the gut of the subject; comparing the detected relative abundance of the at least one of *Prevotella, Coprococcus, Prevotellaceae*, or *Veillonellaceae* bacteria to a predetermined abundance of the at least one of *Prevotella, Coprococcus, Prevotellaceae*, or *Veillonellaceae* bacteria; and selecting, when the relative abundance is below the predetermined abundance, the treatment regimen comprising at least one of modifying microbiota of a gastrointestinal tract of the subject, or applying a therapeutic regimen for treating autism spectrum disorders.

In at least one aspect, a method of increasing balance of a microbiome of a gut of a human subject having autism spectrum disorder (ASD) includes determining a relative abundance of at least one of *Prevotella, Coprococcus, Prevotellaceae*, or *Veillonellaceae* bacteria in the gut of the subject; and administering, when the relative abundance is below a predetermined amount, at least one of a prebiotic, probiotic, or pharmaceutical capable of modifying the relative abundance of the at least one of *Prevotella, Coprococcus, Prevotellaceae*, or *Veillonellaceae* bacteria in the gut.

In at least one aspect, a method of treating a human subject with autism spectrum disorder gut-related symptoms, includes administering, to the subject, a prebiotic to stimulate growth of at least one of *Prevotella, Coprococcus, Prevotellaceae*, or *Veillonellaceae* bacteria in a gut of the subject, wherein a relative abundance of the at least one of *Prevotella, Coprococcus, Prevotellaceae*, or *Veillonellaceae* bacteria in the gut of the subject is below a predetermined abundance.

In at least one aspect, a method of selecting a human subject with autism spectrum disorders (ASD) or gut-related symptoms for inclusion in or exclusion from a clinical trial, comprising subjecting a test sample from a human subject, including microbiota from a gut of the subject, to at least one of nucleic acid extraction, or protein extraction; detecting, using at least one of the extracted nucleic acid or protein, a relative abundance of at least one of *Prevotella, Coprococcus, Prevotellaceae*, or *Veillonellaceae* bacteria in the gut of the subject; and selecting the subject for inclusion in the clinical trial when the relative abundance of the at least one of *Prevotella, Coprococcus, Prevotellaceae,* or *Veillonellaceae* bacteria is below a first predetermined abundance, the first predetermined abundance being an upper-limit for indicating at least one of ASD or gut-related symptoms, and selecting the subject for exclusion from the clinical trial when the relative abundance is above a second predetermined abundance, the second predetermined abundance being a lower limit for indicating at least one of a neurotypical subject or no gut-related symptoms.

In at least one aspect, a computer system for detecting the relative abundance of *Prevotella, Coprococcus, Prevotellaceae,* or *Veillonellaceae* bacteria includes one or more display devices; one or more processors; and at least one memory device storing instructions that, when executed by at least one of the one or more processors, cause the computer system to: subject, via at least one assay module, at least one of: nucleic acid extracted from a test sample of a human subject to a genotyping assay that determines a genus-level genotype of the extracted nucleic acid, the test sample including microbiota from a gut of the subject, or protein extracted from a test sample of a human subject to a protein assay that determines at least one protein indicative of at least one of *Prevotella, Coprococcus, Prevotellaceae,* or *Veillonellaceae* bacteria, the test sample including microbiota from a gut of the subject; and determine, via at least one determination module, a relative abundance of the at least one of *Prevotella, Coprococcus, Prevotellaceae,* or *Veillonellaceae* bacteria that is below a predetermined abundance; display, via at least one of the one or more display devices, at least one determined relative abundance.

In at least one aspect, a computer system for selecting a treatment regimen for a patient includes one or more display devices, one or more processors, and at least one memory device storing instructions that, when executed by at least one of the one or more processors, cause the computer system to: subject, via at least one testing module, a test sample from the human subject, including microbiota from a gut of the subject, to at least one of nucleic acid extraction or protein extraction; detect, via at least one detecting module, at least one of the extracted nucleic acid or protein, a relative abundance of at least one of *Prevotella, Coprococcus, Prevotellaceae,* or *Veillonellaceae* bacteria in the gut of the subject; and compare, via at least one comparing module, the detected relative abundance of the at least one of *Prevotella, Coprococcus, Prevotellaceae,* or *Veillonellaceae* bacteria to a predetermined abundance of the at least one of *Prevotella, Coprococcus, Prevotellaceae,* or *Veillonellaceae* bacteria; select, when the relative abundance is decreased, the treatment regimen comprising at least one of: modifying microbiota of a gastrointestinal tract of the subject, or applying a therapeutic regimen for treating autism spectrum disorders.

DETAILED DESCRIPTION OF PREFERRED EMBODIMENTS

Figure 1A:
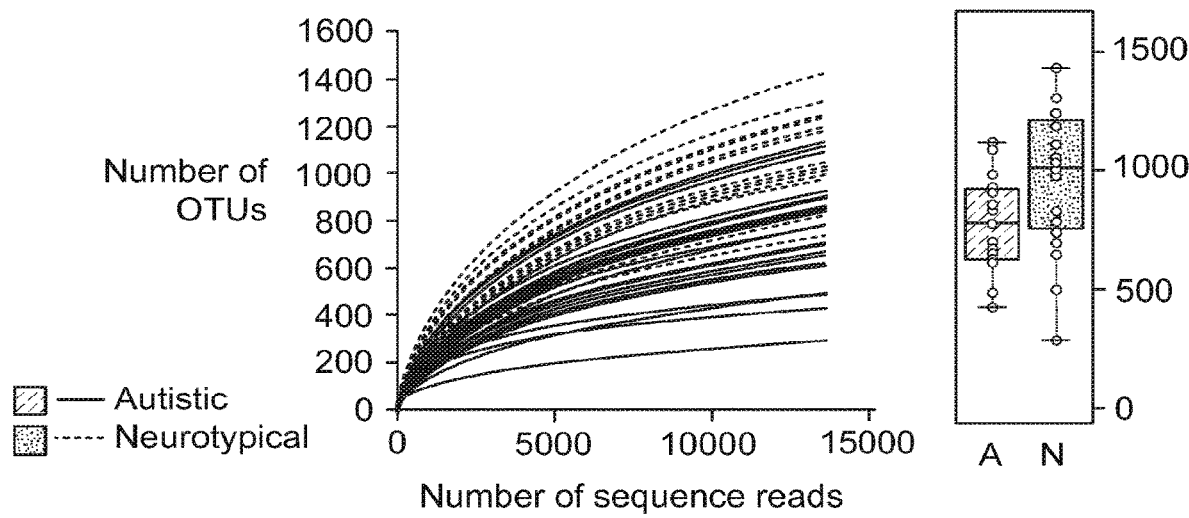
FIG. 1A illustrates rarefaction curves showing unique operating taxonomic units (OTUs) at the 95% threshold, as well as a box graph at the rarefied sequence number for autistic (A) and neurotypical (N) subjects.

It should be understood that this invention is not limited to the particular methodology, protocols, reagents, etc., described herein and, as such, may vary. The terminology used herein is for the purpose of describing particular embodiments only and is not intended to limit the scope of the present invention, which is defined solely by the claims. Unless defined otherwise, all technical and scientific terms used herein have the same meaning as those commonly understood to one of ordinary skill in the art to which this invention pertains.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about."

All patents and other publications identified are expressly incorporated by reference herein for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The human intestine hosts up to $10^{14}$ bacteria, which harmoniously balance the immune system, help digest food, produce vitamins, and promote GI motility. Hence, loss of homeostasis in the gut may contribute to the imbalance of disease states, such as ASD-associated immune and neurological systems, and cause GI problems, which can exacerbate autistic symptoms. The present embodiments provide for the characterization of the healthy gut microbiome and for the characterization of the gut microbiome in Autism spectrum disorders (ASD) subjects. ASDs are complex neurobiological disorders. ASD-diagnosed children have increased noticeably, and ASD has entered into world-wide epidemic level. Both genetic and environmental factors are important in the etiology of autism, but one potentially important environmental factor that has not been deeply explored is abnormal intestinal flora, which often interacts with other factors such as intestinal permeability and transport of toxic substances. Many autistic children and adults suffer from gastrointestinal (GI) problems, and it is likely that abnormal intestinal flora may contribute to those problems. Considering the interactions of intestinal microflora and the central nervous system, human intestinal microbes might also contribute to the autistic symptoms regardless of the manifestation as GI problems.

Techniques for characterizing the microbiome include use of nucleic acid and/or proteins. Nucleic acid analysis includes analysis of, for example, DNA, RNA, mRNA, rRNA, and/or tRNA, and can be accomplished using, for example, pyrosequencing, qPCR, RT-qPCR, clone libraries, DGGE, T-RFLP, ARISA, microarrays, FIFH, dot-blot hybridization, next generation sequencing, and any other DNA hybridization methods that will detect a specific sequence. Protein analysis includes, for example, 2-Dimensional Gel Electrophoresis, 2-Dimensional Difference Gel Electrophoresis (2D-DIGE), MALDI TOF-MS, (2D-) LC-ESI-MS/MS, AQUA, and iTRAQ. These characterizations can be combined with rigorous statistical analysis to determine the constituents of the microbiome. In one non-limiting example, parallel pyrosequencing, provides for high-capacity, low-cost sequencing. The present disclosure uses different statistical tests and the use of rigorous correction methods for multiple testing that strengthen the interpretation of the present data. Bioinformatics provides for the efficient definition of the characteristics and distributions of intestinal microflora between subjects.

A strong positive correlation exists between GI problems and ASD severity ($r=0.6$, $p<0.001$). Human intestinal microbes might also contribute to autistic symptoms because of the interactions of intestinal microbes and the central nervous system. Autistic children use oral antibiotics at an increased rate compared to neurotypical children, and increased use of antibiotics may eliminate beneficial bacteria and help pathogenic bacteria colonize the intestinal walls.

Many gram-negative bacteria work as pathogens because their cell wall contains lipopolysaccharide (LPS), which stimulates host immune systems to cause fever and neurological dysfunction. LPS can increase the permeability of the blood-brain barrier and increase mercury levels in the cerebrum, which may aggravate ASD. LPS also tends to decrease levels of glutathione, an important antioxidant involved in heavy metal detoxification. Lower levels of glutathione may increase the vulnerability of children to ASD and other neurologic disorders such as Parkinson's and Alzheimer's diseases. Pyrosequencing analysis revealed that *Desulfovibrio* and Bacteroides vulgatus, two bacterial species that have LPS in their cell walls, were detected at higher levels in autistic children than in neurotypical children. The gram-positive *Clostridium* is also of interest in the context of ASD because it may have an opportunistic role as endotoxin producer. *Clostridium boltae, C. histolyticum*, and subgroups I and XI also tend to be more abundant in autistic children than in neurotypical children. Enterotoxins from the *Clostridium* species may damage intestinal tissues, which may result in diarrhea and/or may increase absorption of large molecules such as casein and gluten. *Clostridium* species may also produce propionate, which may worsen ASD-like behavior in rat experiments. Additionally, oral vancomycin, an antibiotic that is generally effective against gram-positive bacteria including *Clostridium*, resulted in substantial temporary improvements in gastrointestinal and autistic symptoms in children with late-onset autism.

The human intestine also embraces numerous protective commensal microbes. Microbes domesticate the host and tend to survive together in the long run. *Bifidobacterium* and *Lactobacillus* are good examples of beneficial bacteria in the human intestine, and are often used as probiotics to promote motility. It has been observed that *Bifidobacterium* were less abundant in autistic children, but *Lactobacillus* were more abundant. Many *Clostridium* species are pathogenic, but it has been reported that the sub-group of *Clostridium* IV/XIVa have a beneficial role in maintaining a balanced immune system, similar to the segmented filamentous bacteria.

Molecular techniques such as those based on parallel sequencing enable thorough and systematic identification of intestinal microorganisms. From this, alterations in gut microbe composition can be linked to various human disorders. Despite the linkage between ASD and GI problems, however, no autism-related gut microbe composition profiles and their potential associations to disorder progress and diagnosis were previously observed. Therefore, a pilot study with neurotypical and autistic children was designed, as described herein, accompanied by comprehensive surveys on their GI problems and autistic symptoms. The intestinal microflora of the children enrolled was characterized using 454 GS FLX Titanium pyrosequencing. In-depth analyses revealed that there were significant differences in microbial diversity as well as in composition between the groups. Notably, the differences were more pronounced between neurotypical and autistic children than between autistic children with and without GI problems. The present disclosure provides an association between ASD and/or gut-related problems and gut microflora, which can be potential targets for therapeutics or diagnosis of ASD.

Stool samples were collected from neurotypical and autistic subjects (n=20 each after gender balancing), with the mean (±SD) ages of 8.3 (±4.4) and 7.1 (±3.2) years, respectively, as shown in Table 13 (see Example 1). Among all subjects, there were five female subjects (three neurotypical and two autistic subjects). To estimate the severity of GI symptoms, six categories of GI problems were surveyed, and each subject was scored for the total GI symptom index (6-GSI). In general, the 6-GSI scores in the autistic group were relatively higher (4.6±2.2) than those of neurotypical group (0.5±0.8).

Additionally, the severity of GI problems was compared with autism severity, but the 6-GSI score did not have a significant correlation with the ADOS score (sum of communication and social score), 1=0.35, ATEC (r=0.24), or PDD-BI (r=0.12). Autistic subjects were further divided into two roughly equal-sized groups based on their GI symptoms: autistic-GI+(6-GSI≥6, n=8) and autistic-GI−(6-GSI<6, n=12), with an arbitrary score cutoff.

Figure 1B:
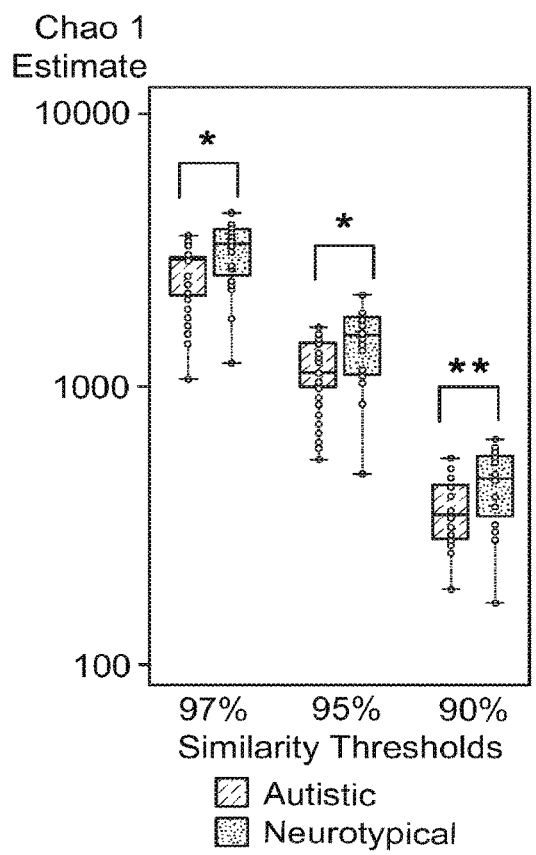
FIG. 1B illustrates Chao1 estimators between neurotypical (right-side box for each similarity threshold) and autistic (left-side box for each similarity threshold) groups at different similarity thresholds (*: $P<0.05$, **: $P<0.01$ by one-tailed Mann-Whitney test).
Figure 5A:
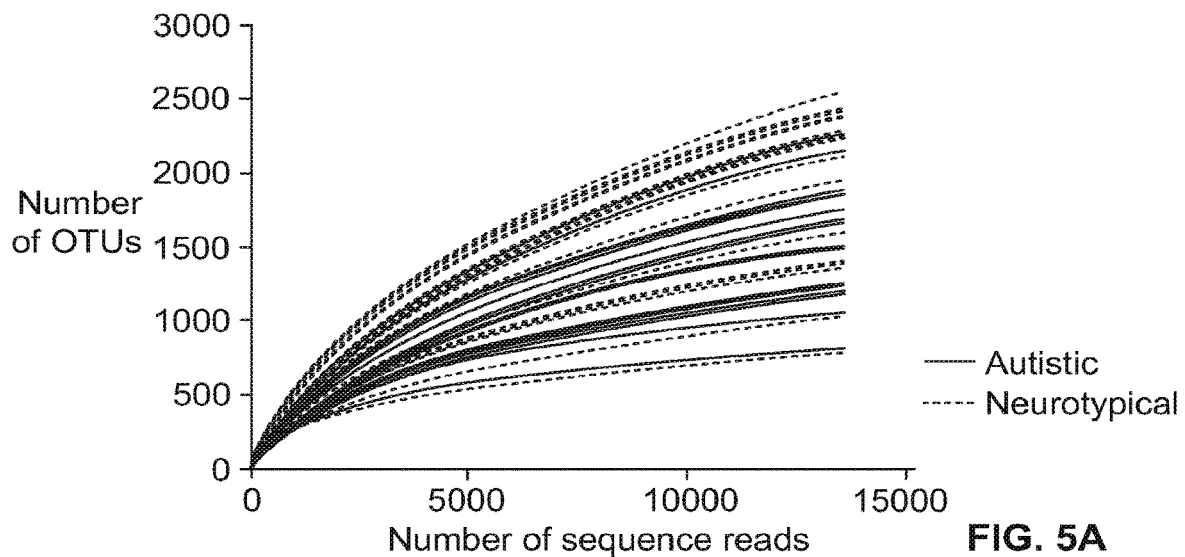
FIG. 5A presents rarefaction curves showing sequencing numbers and OTUs obtained by the UCLUST algorithm with a 97% sequence similarity threshold.
Figure 5B:
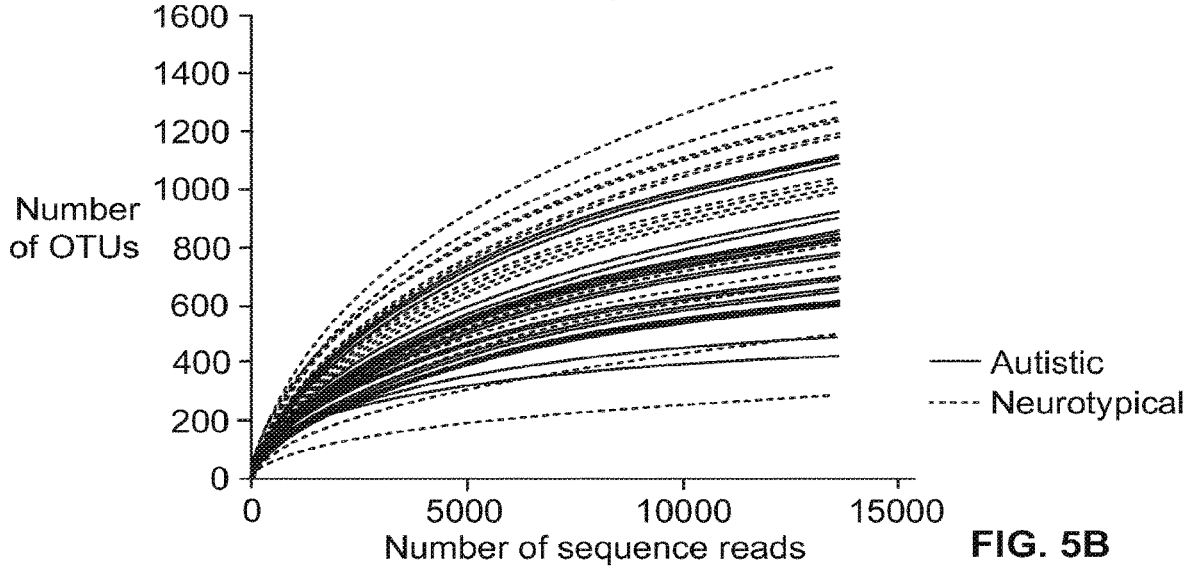
FIG. 5B presents rarefaction curves showing sequencing numbers and OTUs obtained by the UCLUST algorithm with a 95% sequence similarity threshold.
Figure 5C:
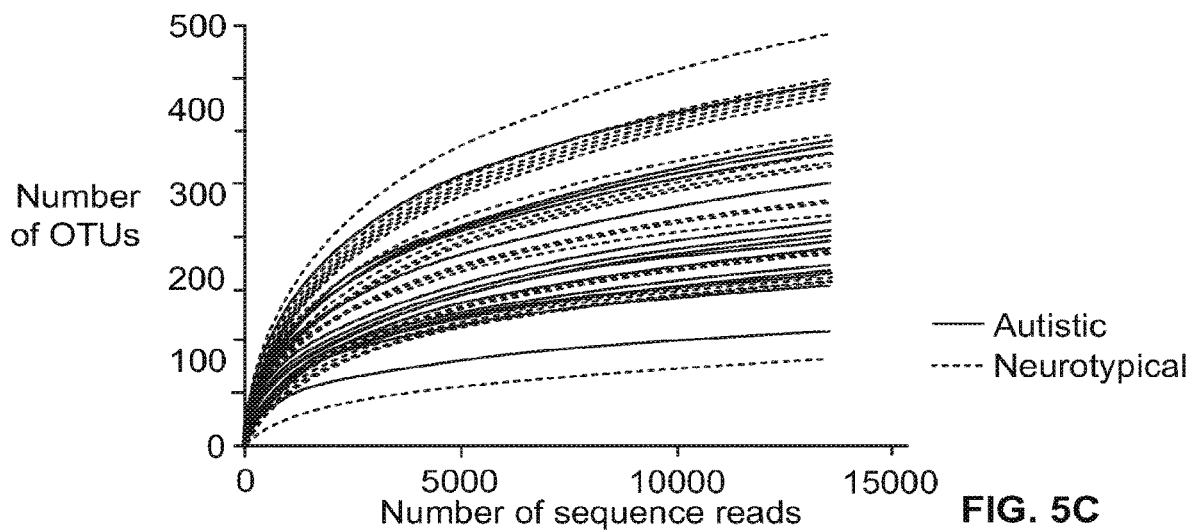
FIG. 5C presents rarefaction curves showing sequencing numbers and OTUs obtained by the UCLUST algorithm with a 90% sequence similarity threshold.

Autism-associated changes in intestinal microbial diversity were characterized. Maintaining sufficient bacterial richness and diversity is important for providing gut microbiota (alternatively, "microflora") with functional redundancy, adaptability, and, thus, systematic robustness against environmental changes. Therefore, with the sequences of 16S rRNA genes, bacterial richness and diversity between groups were compared. An average of about 24,600 sequence-reads per child (about 985,500 sequences in total) was obtained after quality control, and the sequences were classified into OTUs based on their sequence similarities. Rarefaction curves at the 95% (FIG. 1A) and 97% (FIG. 5B) sequence similarity levels showed that neurotypical individuals had a higher number of observed bacterial species than autistic individuals. As an alternative method to estimate the richness and diversity, the nonparametric Chao1 estimator was employed. Similar to the rarefaction data, the neurotypical group had a significantly higher number of estimated OTUs at the 90%, 95%, and 97% thresholds (see FIG. 1B and Table 1), which indicates that the neurotypical group had higher bacterial richness and diversity than the autistic group.

TABLE 1

Microbial diversity indices with OTUs obtained by UCLUST Chao1 estimator

| | UCLUST threshold | | |
|---|---|---|---|
| | 90% | 95% | 97% |
| Neurotypical | 451 | 1453 | 3088 |
| Autistic | 364 | 1165 | 2533 |
| P values (Student's Meg/ Mann-Whitney test) | 0.013/0.010 | 0.010/0.008 | 0.014/0.008 |

TABLE 2

Microbial diversity indices with OTUs obtained by UCLUST Shannon diversity index (H)

| | UCLUST threshold | | |
|---|---|---|---|
| | 90% | 95% | 97% |
| Neurotypical | 3.32 | 4.57 | 5.63 |
| Autistic | 3.27 | 4.43 | 5.38 |
| P values (Student's t-test/ Mann-Whitney test) | 0.42/0.10 | 0.295/0.12 | 0.12/0.08 |

TABLE 3

Microbial diversity indices with OTUs obtained by UCLUST Shannon evenness index (E)

| | UCLUST threshold | | |
|---|---|---|---|
| | 90% | 95% | 97% |
| Neurotypical | 0.57 | 0.66 | 0.74 |
| Autistic | 0.58 | 0.66 | 0.73 |
| P values (Student's t-test/ Mann-Whitney test) | 0.35/0.38 | 0.46/0.21 | 0.25/0.14 |

TABLE 4

Microbial diversity indices with OTUs obtained by UCLUST Phylogenetic Diversity (PD)

| | UCLUST threshold | | |
|---|---|---|---|
| | 90% | 95% | 97% |
| Neurotypical | 29.4 | 59.7 | 71.5 |
| Autistic | 24.9 | 51.2 | 62.8 |
| P values (Student's t-test/ Mann-Whitney test) | 0.018/0.021 | 0.039/0.021 | 0.062/0.031 |

Figure 1C:
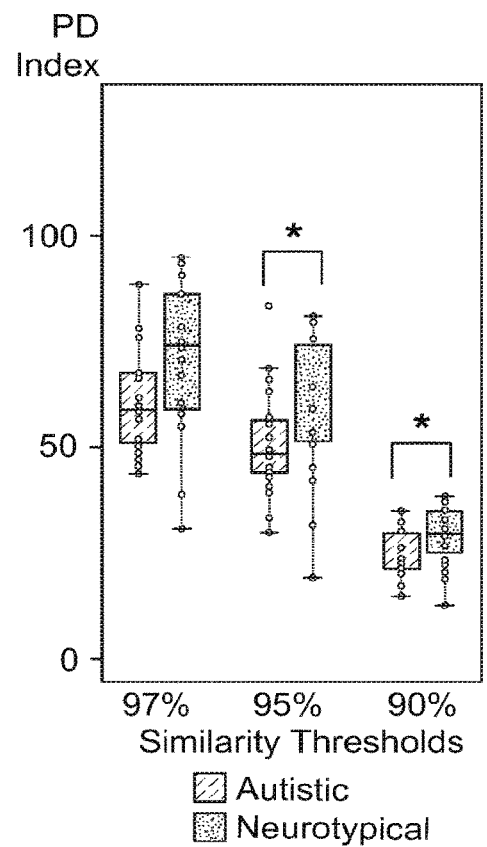
FIG. 1C illustrates the phylogenetic diversity (PD) index between neurotypical (right-side box for each similarity threshold) and autistic (left-side box for each similarity threshold) groups at different similarity thresholds (*: $P<0.05$, **: $P<0.01$ by one-tailed Mann-Whitney test).

Another estimator of microbial diversity, the Shannon diversity index (H), showed similar trends but without statistical significance, and the Shannon evenness index (E) was comparable among groups (see Tables 2, 3). However, the Phylogenetic Diversity (PD) revealed that the neurotypical group harbored more diverse gut microbiota than the autistic group did (P<0.05 by one-tailed Mann-Whitney test, as shown in FIG. 1C and Table 4). In addition, the correlation between bacterial richness/diversity and the severity of GI problems within the autistic group was evaluated, and bacterial richness was negatively correlated with GI severity (see Table 5). Taken together, these data suggest that the presence of autistic symptoms, but not necessarily the severity of GI problems, is strongly associated with reduced richness and diversity of gut microflora, which may result in a decrease in microbial redundancy and, as a result, may alter physiological functionality and robustness in children with ASD.

TABLE 5

Correlation between microbial richness/diversity and severity of GI problems within the autistic group. (P1 and P2: p values from Fisher transformation and permutation test).

| | | UCLUST threshold | | |
|---|---|---|---|---|
| | | 90% | 95% | 97% |
| (A) Chao1 estimator | | | | |
| Pearson | r value | −0.337 | −0.416 | −0.416 |
| | $P_1/P_2$ | 0.158/0.079 | 0.076/0.039 | 0.077/0.038 |
| Spearman rank | r value | −0.267 | −0.378 | −0.395 |
| | $P_1/P_2$ | 0.269/0.133 | 0.111/0.054 | 0.095/0.047 |
| (B) Shannon diversity index | | | | |
| Pearson | r value | −0.21 | −0.125 | 0.013 |
| | $P_1/P_2$ | 0.388/0.193 | 0.609/0.303 | 0.957/0.522 |
| Spearman rank | r value | −0.28 | −0.141 | −0.058 |
| | $P_1/P_2$ | 0.245/0.121 | 0.565/0.278 | 0.815/0.406 |
| (C) Shannon evenness index | | | | |
| Pearson | r value | −0.147 | 0.015 | 0.161 |
| | $P_1/P_2$ | 0.549/0.274 | 0.952/0.524 | 0.509/0.744 |
| Spearman rank | r value | −0.204 | −0.049 | 0.064 |
| | $P_1/P_2$ | 0.402/0.202 | 0.843/0.42 | 0.795/0.6 |
| (D) Phylogenetic Diversity (PD) | | | | |
| Pearson | r value | 0.154 | 0.059 | 0.093 |
| | $P_1/P_2$ | 0.528/0.738 | 0.811/0.592 | 0.705/0.640 |
| Spearman rank | r value | 0.178 | 0.003 | 0.028 |
| | $P_1/P_2$ | 0.465/0.771 | 0.991/0.504 | 0.908/0.544 |

One autistic sample with significantly fewer sequences (about 8,800 reads) than the average (about 25,000 reads) was excluded from further analyses.

Figure 6:
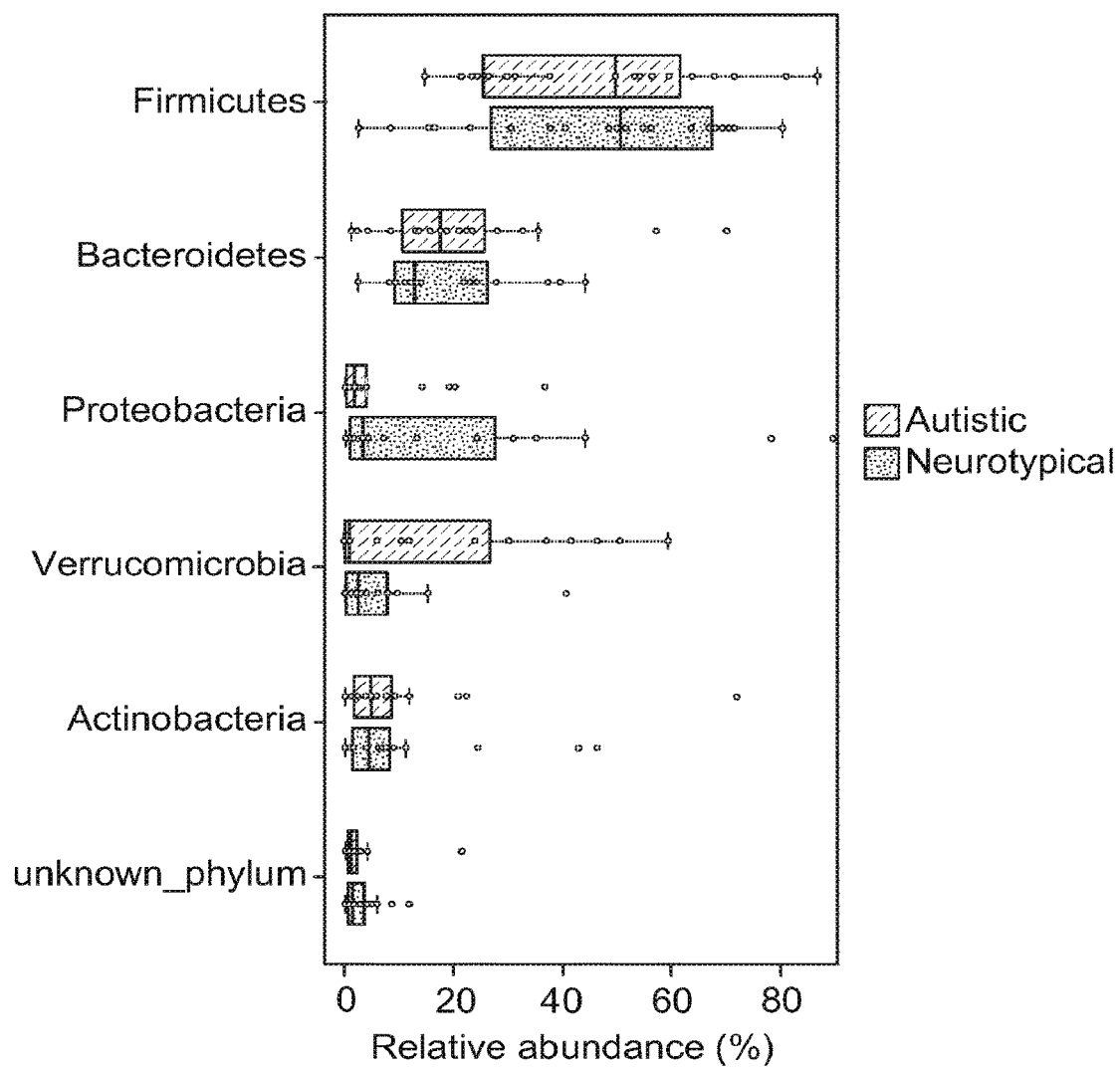
FIG. 6 shows the relative abundance of gut microbiome at the phylum level. The left-side boxes for each bacterium represent autistic children, and the right-side boxes for each bacterium represent neurotypical children.

Additionally, autism-associated changes in gut microflora at phylum level were characterized. For detailed taxonomic analyses, individual sequences were classified by the Ribosomal Database Project ("RDP") classifier described by Wang, Q, G. M. Garrity, J. M. Tiedje, and J. R. Cole, Naïve Bayesian Classifier for Rapid Assignment of rRNA Sequences into the New Bacterial Taxonomy, 73 APPL. ENVIRON MICROBIOL. 16:5261-7 (2007), which is hereby incorporated by reference in its entirety. The RDP classifier assigned approximately 97% of total sequences to fifteen known phyla. *Firmicutes* and Bacteroidetes were the two most dominant phyla, and the phyla *Proteobacteria, Actinobacteria*, and *Verrucomicrobia* were also relatively abundant (as shown in Table 6). These five phyla comprised an average of about 97.2% of total classifiable sequences across samples. Comparison of mean abundance between groups by the Student's t-test showed that the phyla *Proteobacteria* and *Verrucomicrobia* were more abundant in neurotypical and autistic groups, respectively, but this showed no statistical significance after correction for multiple testing (FIG. 6 and Table 6, P adjusted). Because the data were not normally distributed and contained many zero values, the non-parametric Mann-Whitney test was used as the main statistical test throughout this study. The tests showed that there was no significant difference in the relative abundance of individual phyla between the neurotypical and autistic groups (Table 6).

TABLE 6

Relative abundance of fifteen phyla detected in all subjects

| | Median % and 25/75 percentiles | | Student's t-test | | MW-test | |
|---|---|---|---|---|---|---|
| Phylum | Autism | Neurotypical | P | adj. | P | adj. |
| Firmicutes | 52.3 (30.3/62.3) | 53.7 (31.8/68.7) | 0.486 | 0.486 | 0.450 | 0.480 |
| Bacteroidetes | 20.0 (11.8/24.6) | 13.7 (10.6/25.3) | 0.287 | 0.387 | 0.373 | 0.427 |
| Actinobacteria | 4.72 (1.83/8.36) | 4.07 (2.04/7.75) | 0.450 | 0.480 | 0.483 | 0.483 |
| Proteobacteria | 2.08 (0.47/4.66) | 3.45 (1.46/22.7) | 0.049 | 0.248 | 0.063 | 0.263 |
| Verrucomicrobia | 1.02 (0.09/26.2) | 2.62 (0.30/7.46) | 0.039 | 0.248 | 0.363 | 0.427 |
| Unknown phylum | 0.75 (0.67/2.64) | 1.87 (0.87/3.55) | 0.370 | 0.422 | 0.134 | 0.263 |
| Cyanobacteria | 0.01 (<0.01/0.04) | 0.01 (<0.01/0.03) | 0.299 | 0.387 | 0.181 | 0.263 |
| TM7 | 0.01 (<0.01/0.02) | 0.01 (<0.01/0.06) | 0.314 | 0.387 | 0.370 | 0.427 |
| Fusobacteria | <0.01 (<0.01/<0.01) | <0.01 (0/<0.01) | 0.124 | 0.248 | 0.175 | 0.263 |
| Acidobacteria | <0.01 (01<0.01) | <0.01 (0/<0.01) | 0.119 | 0.248 | 0.149 | 0.263 |
| Bacteria_incertae_sedis | <0.01 (0/<0.01) | <0.01 (0/<0.01) | 0.156 | 0.269 | 0.165 | 0.263 |
| Chloroflexi | 0 (0/0) | <0.01 (<0.01/<0.01) | 0.112 | 0.248 | 0.087 | 0.263 |
| Tenericutes | 0 (0/0) | <0.01 (0/<0.01) | 0.075 | 0.248 | 0.044 | 0.263 |
| Synergistetes | 0 (0/0) | <0.01 (01<0.01) | 0.069 | 0.248 | 0.044 | 0.263 |
| Thermotogae | 0 (0/0) | <0.01 (0/<0.01) | 0.111 | 0.248 | 0.087 | 0.263 |
| Nitrospira | 0 (0/0) | <0.01 (0/<0.01) | 0.168 | 0.269 | 0.178 | 0.263 |

Figure 2A:
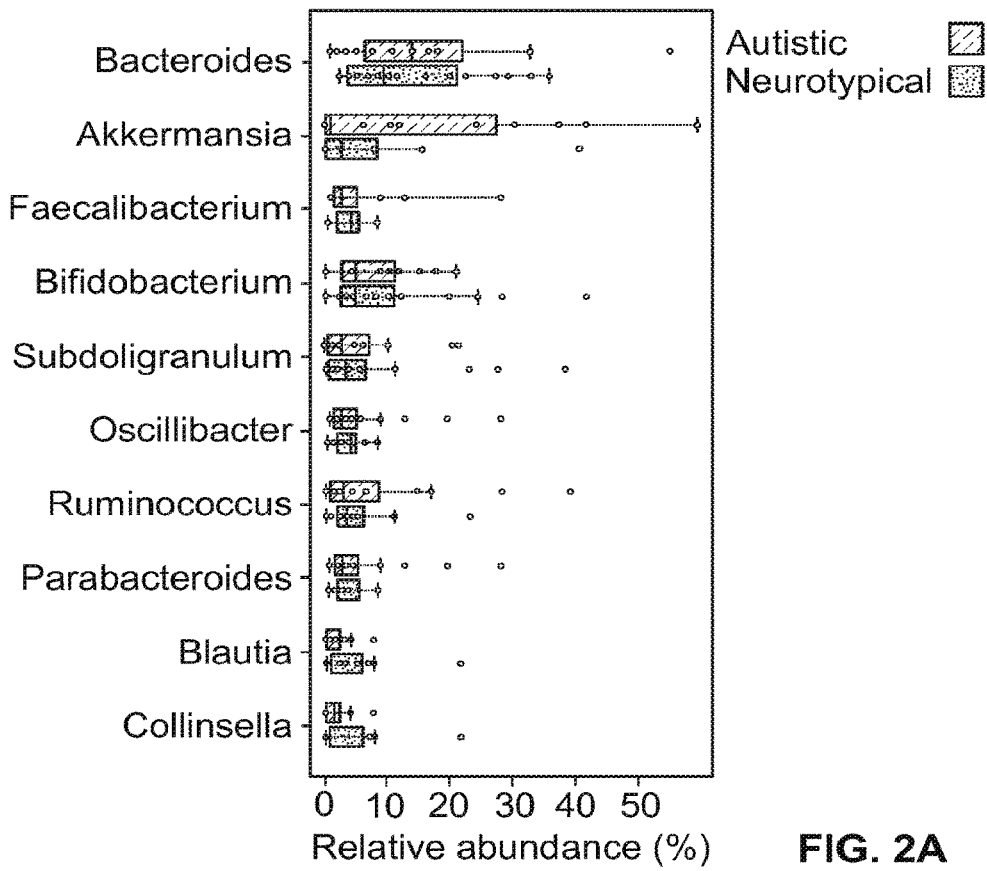
FIG. 2A shows the distribution of 39 subjects based on relative abundance of the top 10 most abundant genera for autistic (top box for each genera) and neurotypical (bottom box for each genera) subjects.

Further, autism-associated changes in gut microflora at the genus level were distinguished. Among 214 genera identified by the RDP classifier, the genera Bacteroides, *Faecalibacterium, Bifidobacterium, Akkermansia*, and *Subdoligranulum* were commonly the top five most abundant genera in both neurotypical and autistic groups, in which the five genera comprised about 38% and about 52% of total sequences, respectively (FIG. 2A and Table 7).

TABLE 7

Top 20 genera out of 214 known genera in neurotypical (N) and autistic (A) subjects.

| Normal | #N (n = 20) | % Total | Autistic | #A (n = 19) | % Total |
|---|---|---|---|---|---|
| *Bacteroides* | 20 | 13.11 | *Bacteroides* | 20 | 17.73 |
| *Faccalibacterium* | 20 | 9.20 | *Akkermansia* | 20 | 12.97 |
| Bifidobacterium | 20 | 5.89 | Bifidobacterium | 16 | 7.41 |
| *Akkermansia* | 19 | 5.22 | *Faecalibacterium* | 18 | 7.35 |
| *Subdoligranulum* | 20 | 4.64 | *Subdoligranulum* | 19 | 6.77 |
| *Oscillibacter* | 20 | 4.38 | *Blautia* | 18 | 3.56 |
| *Ruminococcus* | 19 | 1.88 | *Ruminococcus* | 20 | 2.85 |
| *Parabacteroides* | 20 | 1.82 | *Parabacteroides* | 20 | 2.48 |
| *Escherichia/Shigella* | 14 | 1.80 | *Oscillibacter* | 20 | 1.91 |
| *Collinsella* | 17 | 1.73 | *Parasutterella* | 13 | 1.29 |
| *Prevotella* | 15 | 1.40 | *Phascolarctobacterium* | 11 | 0.82 |
| *Anaerotruncus* | 19 | 1.21 | *Escherichia/Shigella* | 13 | 0.74 |
| *Phascolarctobacterium* | 7 | 1.16 | *Anaerotruncus* | 20 | 0.72 |
| *Blautia* | 20 | 1.12 | *Dialister* | 12 | 0.69 |
| *Paraprevotella* | 10 | 0.86 | *Butyricicoccus* | 16 | 0.67 |
| *Sutterella* | 13 | 0.70 | *Veillonella* | 16 | 0.67 |
| *Roseburia* | 20 | 0.53 | *Coprobacillus* | 18 | 0.67 |
| *Coprobacillus* | 20 | 0.52 | *Collinsella* | 14 | 0.62 |
| *Dialister* | 16 | 0.43 | *Alistipes* | 17 | 0.41 |
| *Citrobacter* | 13 | 0.41 | *Barncsiella* | 4 | 0.33 |

The subject numbers (#N and #A) are counts of subjects that contained corresponding genera in fecal samples. The average percentage of each genus is indicated in the column '% Total.'

Figure 7:
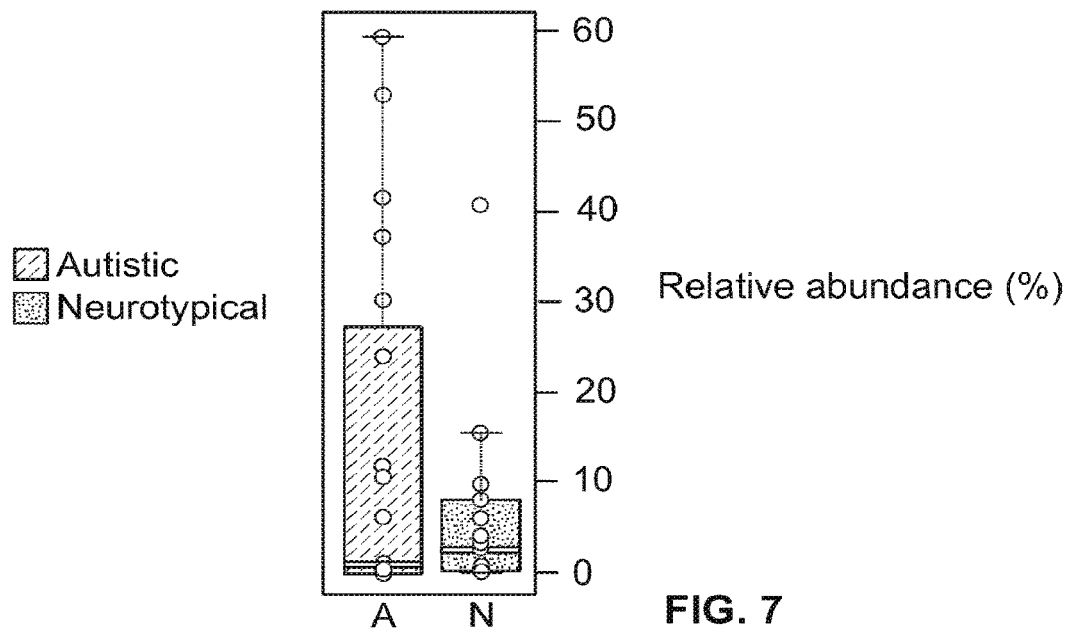
FIG. 7 illustrates the distribution of relative abundance of the genus *Akkermansia* in 39 subjects. N: neurotypical; A: autistic group.

Surprisingly, the *Akkermansia* genus, a mucin degrader, was present at very high levels in several autistic and neurotypical subjects, representing about 30% to about 50% of all sequences (FIG. 7).

When the mean abundance of each genus was compared between groups by the unadjusted Student's t-test, the genera *Prevotella, Oscillibacter*, and *Paraprevotella* were more abundant in the neurotypical group, and the genus *Akkermansia* was more abundant in the autistic group (Table 8).

TABLE 8

Genera having significant difference, relative abundance.

(a) Neurotypical and autistic children (Adjusted P values were 0.245 for all listed genera)

| Family.Genus | P value | Median(25/75 percentiles) Neurotypical | Autism |
|---|---|---|---|
| Lachnospiraceae.*Coprococcus I* | 0.0333 | 0.04(0.02/0.05) | 0.01(0/0.02) |
| Incertae_Sedis_XII.*Fusibacter* | 0.011 | <0.01(0/0.02) | 0(0/0) |
| Desulfovibrionaceae.*Desulfovibrio* | 0.013 | <0.01(0/0.22) | 0(0/0) |
| Coriobacteriaceae.unknown genus | 0.013 | 0.09(0.02/0.26) | 0.02(0.02/0.07) |
| Coriobacteriaceae.*Eggerthella* | 0.013 | 0.02(0.01/0.05) | 0.05(0.02/0.29) |
| Ruminococcaceae.*Oscillibacter* | 0.022 | 2.99(0.93/6.76) | 1.82(0.27/2.46) |
| Peptostreptococcaceae.*Peptostreptococcus* | 0.025 | 0(0/0) | 0(0/0) |
| Incertae_Sedis_XII.unknown_genus | 0.025 | 0(0/<0.01) | 0(0/0) |
| Porphyromonadaceae.unknown_genus | 0.029 | 0.02(0/0.14) | 0(0/<0.01) |
| Prevotellaceae.*Prevotella* | 0.029 | 0.09(0.01/0.73) | 0(0/<0.01) |
| Prevotellaceae.unknown_genus | 0.031 | 0.01(0/0.03) | 0(0/0) |
| Lactobacillaceae.unknown_genus | 0.034 | 0(0/0) | 0(0/0) |
| Veillonellaceae.unknown genus | 0.035 | 0.05(0.01/0.25) | 0(0/0.01) |
| Ruminococcaceae.*Papillibacter* | 0.036 | 0(0/0) | 0(0/0) |
| Coriobacteriaceae.*Olsenella* | 0.037 | 0(0/0) | 0(0/0) |
| Aerococcaceae.*Abiotrophia* | 0.039 | 0(0/0) | 0(0/0) |

TABLE 8-continued

Genera having significant difference, relative abundance.

| | | | |
|---|---|---|---|
| Verrucomicrobiaceae.*Akkermansia* | 0.039 | 2.62(0.30/7.46) | 1.01(0.09/25.93) |
| Staphylococcaceae.*Staphylococcus* | 0.044 | 0(0/0.01) | 0(0/0) |
| Enterobacteriaceae.unknown_genus | 0.045 | 1.28(0.20/17.98) | 0.42(0.1/2.45) |
| Prevotellaceae.*Paraprevotella* | 0.045 | 0(0/0.36) | 0(0/0) |
| Porphyromonadaceae.*Butyricimonas* | 0.045 | 0(0/0.10) | 0(0/0) |
| Eubacteriaceae.*Eubacterium* | 0.046 | 0.04(0.02/0.12) | 0.15(0.07/0.30) |
| Coriobacteriaceae.*Atopobium* | 0.049 | 0(0/0.01) | 0(0/0) |

(b) Autistic children with/without severe GI problems
(Adjusted P values were 0.313 for all genera)

| | | Median (25/75 percentiles) | |
|---|---|---|---|
| Family.Genus | P value | GI+ | GI+ |
| Ruminococcaceae.*Acetivibrio* | 0.029 | 0.04(0/0.07) | <0.01(0/0.01) |
| Ruminococcaceae.*Subdoligranulum* | 0.038 | 1.90(0.54/5.26) | 6.21(1.85/17.76) |
| Ruminococcaceae.*Anaerotruncus* | 0.049 | 0.38(0.23/0.62) | 0.81(0.39/1.10) |
| Enterobacteriaceae.unknown_genus | 0.050 | 1.15(0.07/1.86) | 0.29(0.11/11.54) |

Figure 2B:
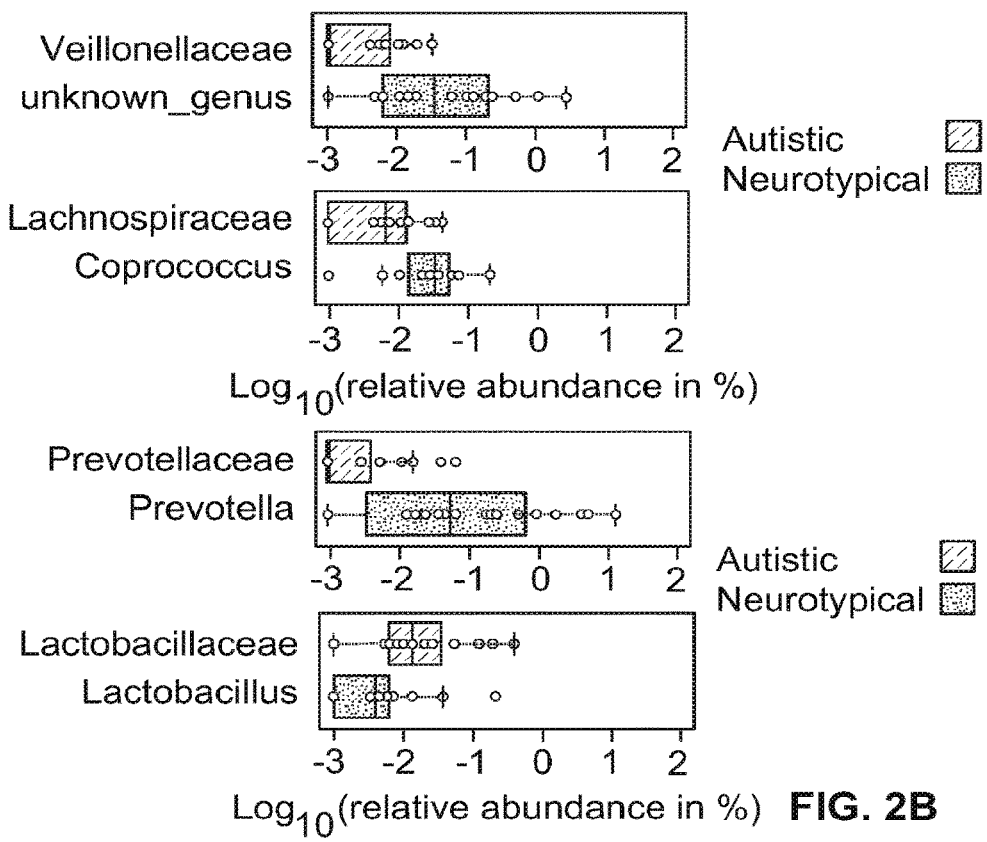
FIG. 2B shows the distribution of 39 subjects based on relative abundance of the 4 most differentially abundant genera for autistic (top box for each genera) and neurotypical (bottom box for each genera) subjects.
Figure 2C:
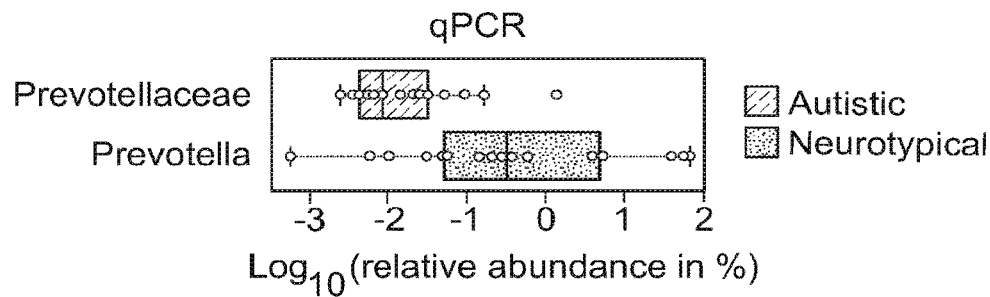
FIG. 2C shows the distribution of 39 subjects based on relative abundance of the genus *Prevotella* obtained by qPCR analysis for autistic (top box for each genera) and neurotypical (bottom box for each genera) subjects.
Figure 2D:
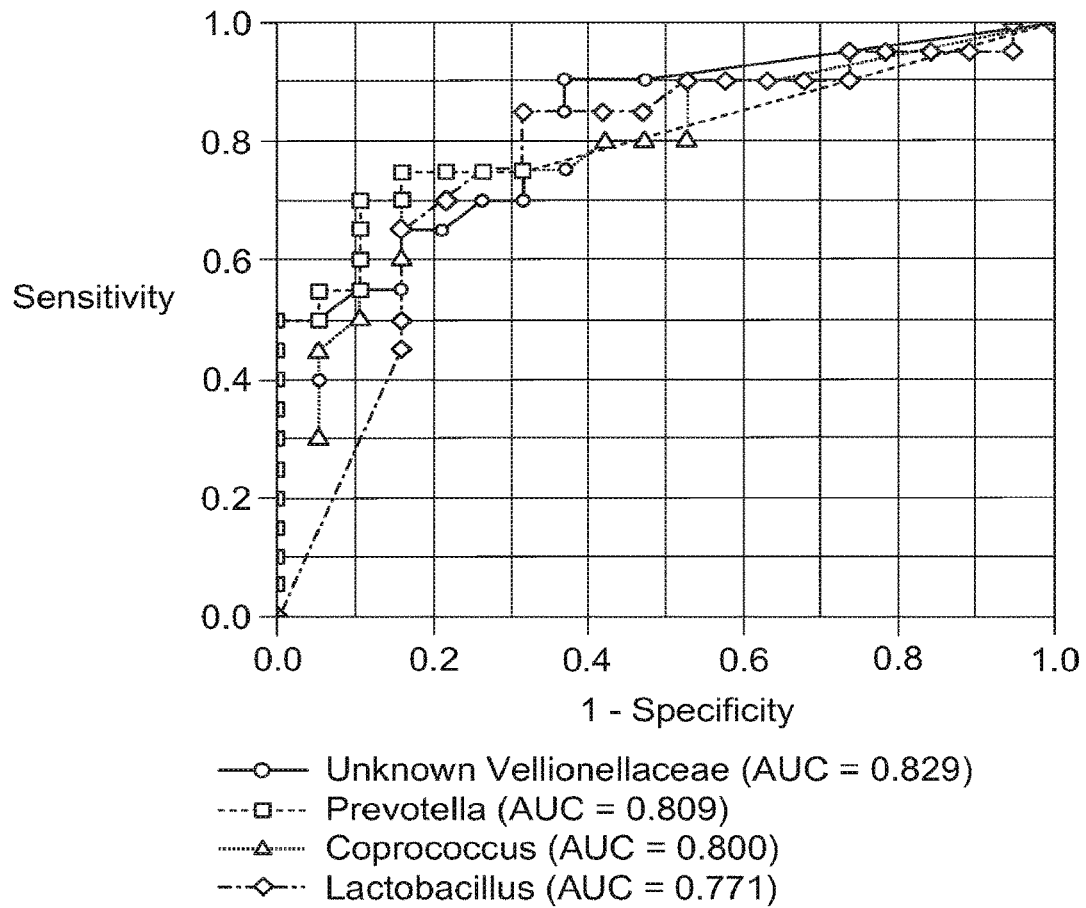
FIG. 2D shows a receiver operating characteristics (ROC) curve of the 4 genera that have the highest area under curve (AUC).

The Mann-Whitney test with multiple testing correction showed that *Prevotella* and unclassified *Veillonellaceae* were significantly more abundant in the neurotypical group than in the autistic group (adjusted P-0.05, Tables 9 and 10, FIG. 2B). The reduced abundance of *Prevotella* in autistic children was confirmed by use of quantitative real-time PCR (qPCR) (Mann-Whitney test P=0.0002, FIG. 2C).

TABLE 9

By nonparametric rank-sum test (Mann-Whitney test)

(a) top ten differentially abundant genera between neurotypical and autistic children

| | | P | Median (25%/75%) | |
|---|---|---|---|---|
| Name | P | adjusted | Neurotypical | Autism |
| Prevotellaceae.*Prevotella* | 0.000 | 0.050 | 0.09(0.01/0.73) | 0(01<0.01) |
| Veillonellaceae.unknown_genus | 0.000 | 0.050 | 0.05(0.01/0.25) | 0(0/0.01) |
| Lachnospiraceae.*Coprococcus* | 0.001 | 0.055 | 0.04(0.02/0.05) | 0.01(0/0.02) |
| Prevotellacae.unknown_genus | 0.001 | 0.055 | 0.01(0/0.03) | 0(0/0) |
| Alcaligenaceae.*Sutterella* | 0.002 | 0.108 | 0.07(0/0.21) | 0(0/0) |
| Lactobacillaceae.*Lactobacillus* | 0.003 | 0.134 | <0.01(0/0.01) | 0.02(0.01/0.05) |
| Porphyromonadaceae.*Butyricimonas* | 0.004 | 0.138 | 0(0/0.10) | 0(0/0) |
| Prevotellaceae.*Prevotella* | 0.004 | 0.140 | 0(0/0.36) | 0(0/0) |
| Incertae_Sedis_XII.*Fusibacter* | 0.005 | 0.144 | <0.01(0/0.02) | 0(0/0) |
| Lachnospiraceae.*Roseburia* | 0.006 | 0.144 | 0.07(0.04/0.21) | 0.03(0.01/0.07) |

(b) differentially abundant genera between autistic
children with or without severe GI problems

| | | P | Median (25%/75%) | |
|---|---|---|---|---|
| Name | P | adjusted | GI− | GI+ |
| Desulfovibrionaceae.*Desulfovibrio* | 0.036 | 0.462 | 0(0/0.01) | 0(0/0) |
| Alcaligenaceae.*Sutterella* | 0.036 | 0.462 | 0(0/0.03) | 0(0/0) |
| Ruminococcaceae.*Anaerotruncus* | 0.038 | 0.462 | 0.38(0.23/0.62) | 0.81(0.39/1.10) |

TABLE 10

By nonparametric rank-sum test (Maim-Whitney test), differentially abundant genera between neurotypical and autistic children

| Name | P | P adjusted | Median (25%/75%) Neurotypical | Median (25%/75%) Autism |
|---|---|---|---|---|
| Prevotellaceae.*Prevotella* | 0.000 | 0.050 | 0.09(0.01/0.73) | 0(01<0.01) |
| Veillonellaceae.unknown_genus | 0.000 | 0.050 | 0.05(0.01/0.25) | 0(0/0.01) |
| Lachnospiraceae.*Coprococcus* | 0.001 | 0.055 | 0.04(0.02/0.05) | 0.01(0/0.02) |
| Prevotellaceae.unknown_genus | 0.001 | 0.055 | 0.01(0/0.03) | 0(0/0) |
| Alcaligenaceae.*Sutterella* | 0.002 | 0.108 | 0.07(0/0.21) | 0(0/0) |
| Lactobacillaceae.*Lactobacillus* | 0.003 | 0.134 | <0.01(0/0.01) | 0.02(0.01/0.05) |
| Porphyromonadaceae.*Butyricimonas* | 0.004 | 0.138 | 0(0/0.10) | 0(0/0) |
| Prevotellaceae.*Prevotella* | 0.004 | 0.140 | 0(0/0.36) | 0(0/0) |
| Incertae_Sedis_XII.*Fusibacter* | 0.005 | 0.144 | <0.01(0/0.02) | 0(0/0) |
| Lachnospiraceae.*Roseburia* | 0.006 | 0.144 | 0.07(0.04/0.21) | 0.03(0.01/0.07) |
| Porphyromonadaceae.unknown_genus | 0.009 | 0.213 | 0.02(0/0.14) | 0(0/<0.01) |
| Staphylococcaceae.*Staphylococcus* | 0.010 | 0.213 | 0(0/0.01) | 0(0/0) |
| Veillonellaceae.*Succinispira* | 0.012 | 0.232 | 0(01<0.01) | 0(0/0) |
| Eubacteriaceae.*Eubacterium* | 0.016 | 0.259 | 0.04(0.02/0.12) | 0.15(0.07/0.30) |
| Incertae_Sedis_XI.*Parvimonas* | 0.016 | 0.259 | <0.01(0/0.01) | 0(0/0) |
| Aerococcaceae.*Abiotrophia* | 0.017 | 0.259 | 0(0/0) | 0(0/0) |
| Coriobacteriaceae.*Eggerthella* | 0.019 | 0.259 | 0.02(0.01/0.05) | 0.05(0.02/0.29) |
| Desulfovibrionaceae.*Desulfovibrio* | 0.019 | 0.259 | <0.01(0/0.022) | 0(0/0) |
| Desulfovibrionaccae.unknown_genus | 0.021 | 0.259 | 0.02(0.01/0.03) | 0.01(0/0.02) |
| Enterobacteriaceae.*Providencia* | 0.023 | 0.259 | 0(0/0) | 0(0/0) |
| Peptostreptococcaceae.*Peptostreptococcus* | 0.023 | 0.259 | 0(0/0) | 0(0/0) |
| Coriobactcriaccae.*Olsenclla* | 0.023 | 0.259 | 0(0/0) | 0(0/0) |
| Lachnospiraceae.*Dorea* | 0.023 | 0.259 | 0.03(0.02/0.10) | 0.02(0.01/0.03) |
| Ruminococcaceae.*Oscillibacter* | 0.024 | 0.259 | 2.99(0.93/6.7) | 1.82(0.27/2.46) |
| Incertae_Sedis_XII.unknown genus | 0.025 | 0.259 | 0(01<0.01) | 0(0/0) |
| Veillonellaceae.*Veillonella* | 0.026 | 0.259 | 0.01(0/0.02) | 0.02(0.01/0.07) |
| Coriobactcriaccac.unknowngenus | 0.030 | 0.268 | 0.09(0.02/0.26) | 0.02(0.02/0.07) |
| Neisseriaceae.*Microvirgula* | 0.031 | 0.268 | 0(0/<0.01) | 0(0/0) |
| Veillonellaceae.*Allisonella* | 0.034 | 0.268 | 0(01<0.01) | 0(0/0) |
| Lactobacillaceae.unknown_genus | 0.036 | 0.268 | 0(0/0) | 0(0/0) |
| Ruminococcaceae.*Papillibacter* | 0.036 | 0.268 | 0(0/0) | 0(0/0) |
| Thermoanaerobacteraceae.unknown_genus | 0.044 | 0.268 | 0(0/0) | 0(0/0) |
| Desulfovibrionaceae.*Desulfocurvus* | 0.044 | 0.268 | 0(0/0) | 0(0/0) |
| Spiroplasmataceae.*Spiroplasma* | 0.044 | 0.268 | 0(0/0) | 0(0/0) |

In addition, with marginal statistical significances, the abundance of *Coprococcus* and unclassified *Prevotellaceae* were also higher in neurotypical samples (adjusted P=0.055, Table 9, FIG. 2B). To measure how correctly two groups of samples could be classified by the relative abundance of each genus, the receiver operating characteristics (ROC) curve was employed, which is closely related to the Mann-Whitney test and commonly used to evaluate the performance of potential biomarkers. The probability of correct prediction by a given binary classifier can be evaluated by measuring the area under curves (AUC) that depict true versus false positives rates, where the AUC value ranges from about 0.5 (random classification) to about 1.0 (perfect classification), as described in Hanley & McNeil, "The meaning and use of the area under a receiver operating characteristic (ROC) curve," 143 Radiol. 29 (1982), which is hereby incorporated by reference in its entirety. The above-mentioned four genera showed the highest AUC values among all genera, at around 0.8 (FIG. 2C and Table 11), which are highly comparable to biomarkers for many clinical disorders, such as for the detection of drug-induced kidney injury and prostate cancer.

TABLE 11

The top 11 genera having the highest area under curves (AUC)

| Genus Name | AUC | Median (25%/75%) Neurotypical | Median (25%/75%) Autism |
|---|---|---|---|
| Veillonellaceae.unknown_genus | 0.812 | 0.05(0.01/0.25) | 0(0/0.01) |
| Prevotellaceae.*Prevotella* | 0.808 | 0.09(0.01/0.73) | 0(01<0.01) |
| Lachnospiraceae.*Coprococcus* | 0.799 | 0.04(0.02/0.05) | 0.01(0/0.02) |
| Prevotellaceae.unknown_genus | 0.754 | 0.01(0/0.03) | 0(0/0) |
| Lactobacillaceae.*Lactobacillus* | 0.754 | <0.01(0/0.01) | 0.02(0.01/0.05) |
| Alcaligenaceae.*Sutterella* | 0.745 | 0.07(0/0.21) | 0(0/0) |
| Lachnospiraccae.*Roseburia* | 0.739 | 0.07(0.04/0.21) | 0.03(0.01/0.07) |
| Porphyromonadaceae.*Butyricimonas* | 0.712 | 0(0/0.10) | 0(0/0) |
| Porphyromonadaceae.unknown_genus | 0.704 | 0.02(0/0.14) | 0(0/<0.01) |

TABLE 11-continued

The top 11 genera having the highest area under curves (AUC)

| Genus Name | AUC | Median (25%/75%) | |
| --- | --- | --- | --- |
| | | Neurotypical | Autism |
| Prevotellaceae.*Paraprevotella* | 0.703 | 0(0/0.36) | 0(0/0) |
| Eubacteriaceae.*Eubacterium* | 0.703 | 0.04(0.02/0.12) | 0.15(0.07/0.30) |

Figure 3A:
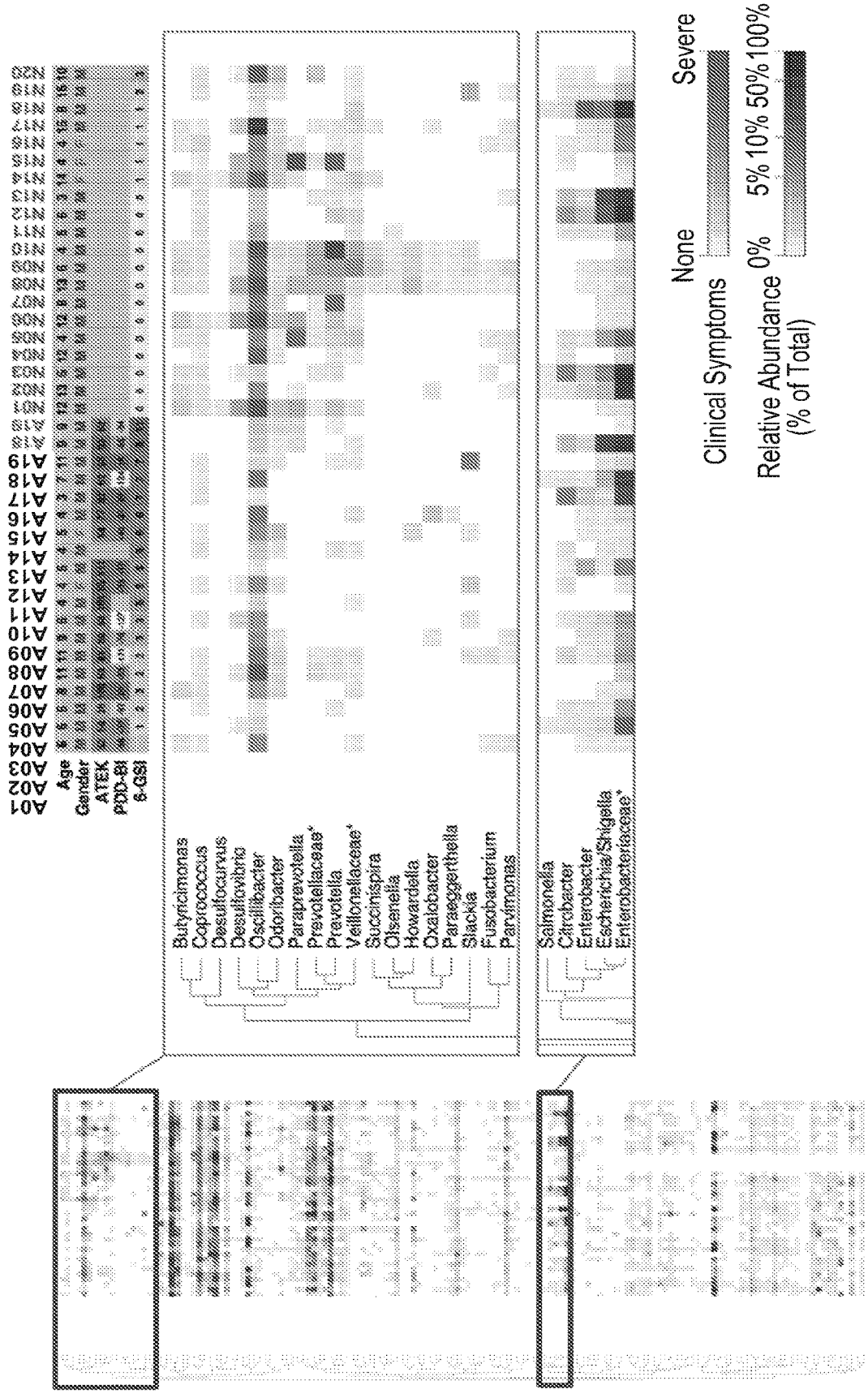
FIG. 3A shows heat map profiles and dendrograms of the all identified genera (A01-A11: autistic children with GI problems; A12-A19: autistic children without GI problems; N01-N20: neurotypical children).
Figure 8A:
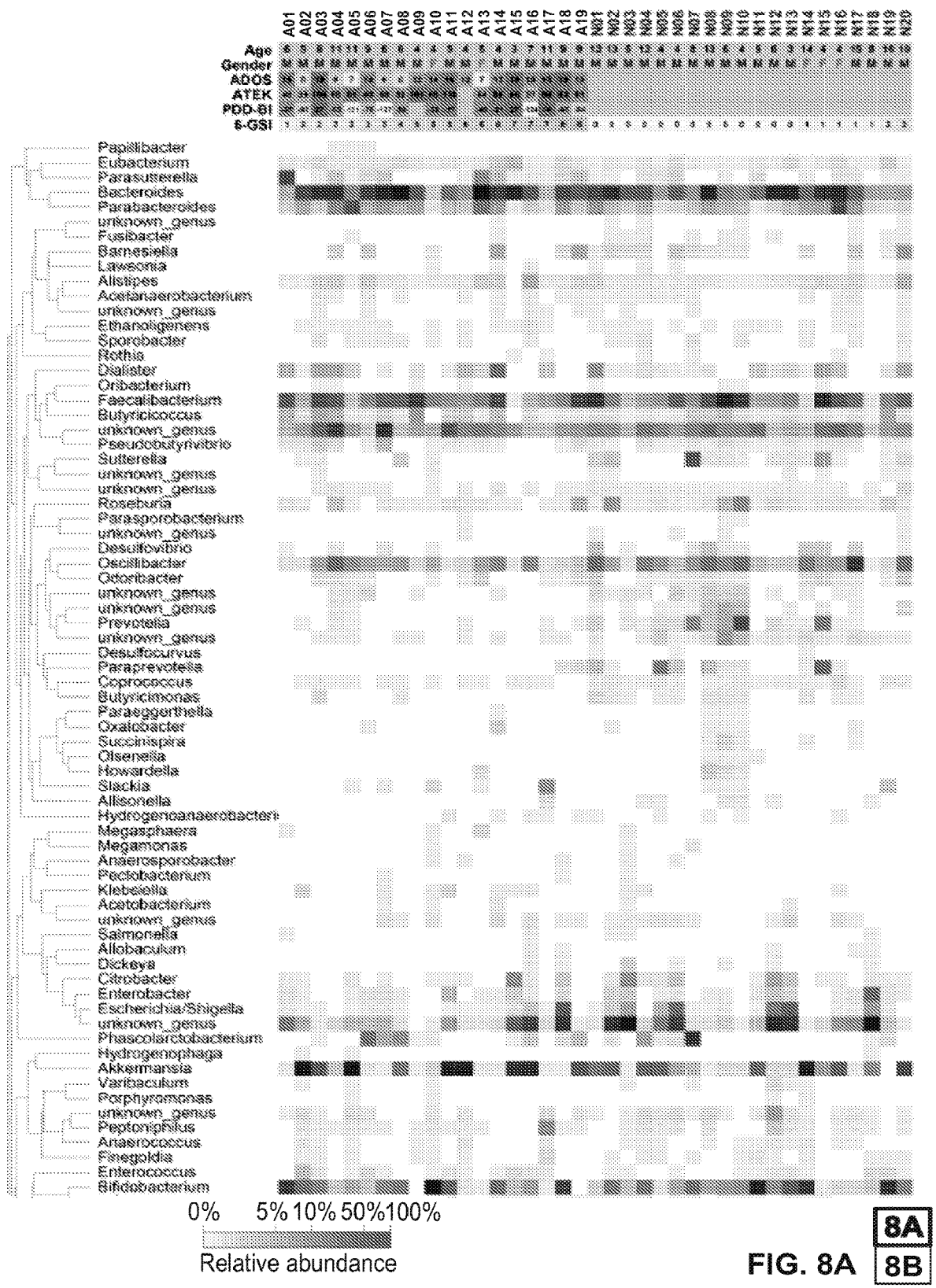
FIG. 8A shows a heat map profile and a dendrogram of the all identified genera (A01-A1 1: autistic children with GI problems; A12-A19: autistic children without GI problems; N01-N20: neurotypical children). A scale bar represents a log scale of the percentile abundance from a total bacteria.
Figure 8B:
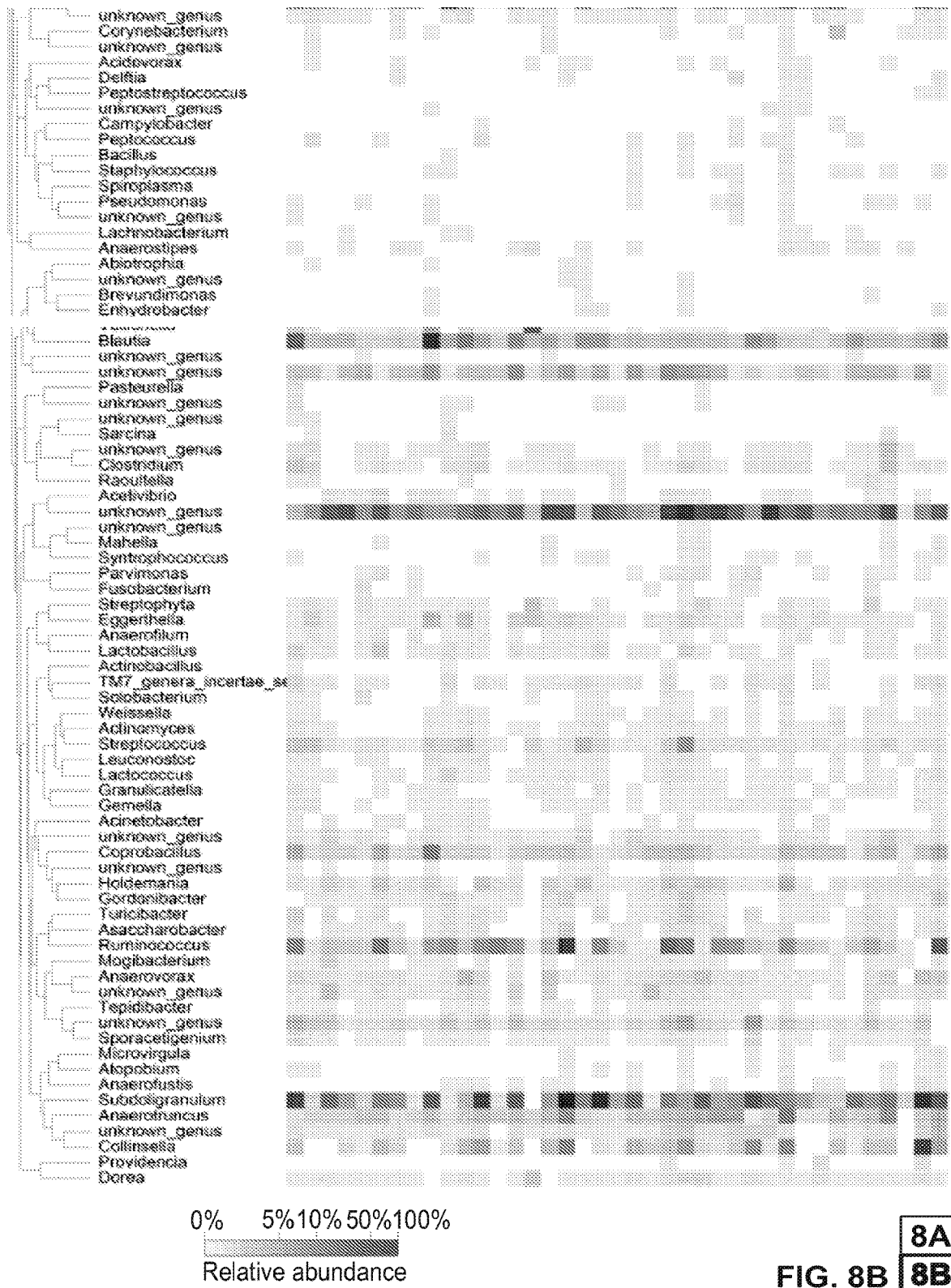
FIG. 8B is a continuation of the heat map profile and dendrogram of FIG. 8A.

Moreover, the present work revealed autism-associated changes in microbial community profile and enterotypes. Like other environmental microbial ecosystems, human intestinal microflora is distinctively shaped by diverse microorganisms and their mutual interactions. Therefore, autism-related microflora alterations could be found at the level of community, rather than at the individual microbe level. In an effort to identify the systematic differences in microbial communities between neurotypical and autistic groups, all genera were hierarchically clustered based on their relative abundance across samples (FIG. 8). Although the majority of clusters showed no apparent difference between the groups, one cluster of eleven genera that included *Prevotella* were, in general, at a greater abundance in neurotypical samples (FIG. 3A). In addition, these genera shared a similar pattern, especially within neurotypical samples, indicating a coherent relationship among them. Surprisingly, another cluster enriched in *Enterobacteriaceae* (FIG. 3A) displayed a negatively correlated pattern to the *Prevotella* cluster within the neurotypical group (Pearson/Spearman rank correlation coefficient r=−0.52/−0.67, Fisher transformation test P=0.02/0.001, and permutation test P=0.0002/0.0008). No increase of the *Enterobacteriaceae* cluster was observed in autistic children, however, despite the significant decrease in *Prevotella*. This suggests that community-wide interrelationship of gut microbiota is generally altered in autistic children.

Principal component analysis (PCA) was performed on 16S rRNA sequencing datasets, and three well-defined 'enterotypes' of human gut microbiota were identified based on the global profiles at the genus level. In addition, the ratio among enterotypes was maintained, regardless of certain disorder conditions, such as obesity and inflammatory bowel disease (IBD), which tend to alter gut microbiota. Notably, *Prevotella* was one of the main classifiers of the three enterotypes, along with Bacteroides and *Ruminococcus*. Moreover, a similar co-occurrence pattern to the present data, in which *Desulfovibrio* and *Veilonella* (as an unidentifiable *Veilonellaceae* in the cluster, FIG. 3A) co-occurred with *Prevotella*, while *Escherichia/Shigella* showed a negative correlation (FIG. 3A). Therefore, given that *Prevotella* was the main difference between neurotypical and autistic groups, any changes in the enterotype profile associated with autism were analyzed. PCA was performed on all thirty-one samples with the relative abundance of sixteen selected genera (Table 12) that commonly appeared in both studies.

TABLE 12

Bacterial groups in co-occurrence networks of enterotype study Genus

| | | |
| --- | --- | --- |
| *Akkermansia*† | *Gordonibacter*† | *Prevotella*† |
| Alkaliphilus | Helicobacter | Rhodospirillum |
| *Bacteroides*† | *Holdemania*† | Ruminococcaceae |
| *Catenibacterium*† | Lachnospiraceae | *Ruminococcus*† |
| Clostridiales | *Lactobacillus*† | Slackia |

TABLE 12-continued

Bacterial groups in co-occurrence networks of enterotype study Genus

| | | |
| --- | --- | --- |
| *Desulfovibrio*† | Leuconostoc | Sphingobacterium |
| *Dialister*† | Marvinbryantia | *Staphylococcus*† |
| *Eggerthellata*† | Methanobrevibacter | *Subdoligranulum*† |
| *Escherichia/Shigellata*† | *Parabacterioides*† | Symbiobacterium |
| Geobacter | Peptostreptococcaceae | *Veillonella*† |

Figure 3B:
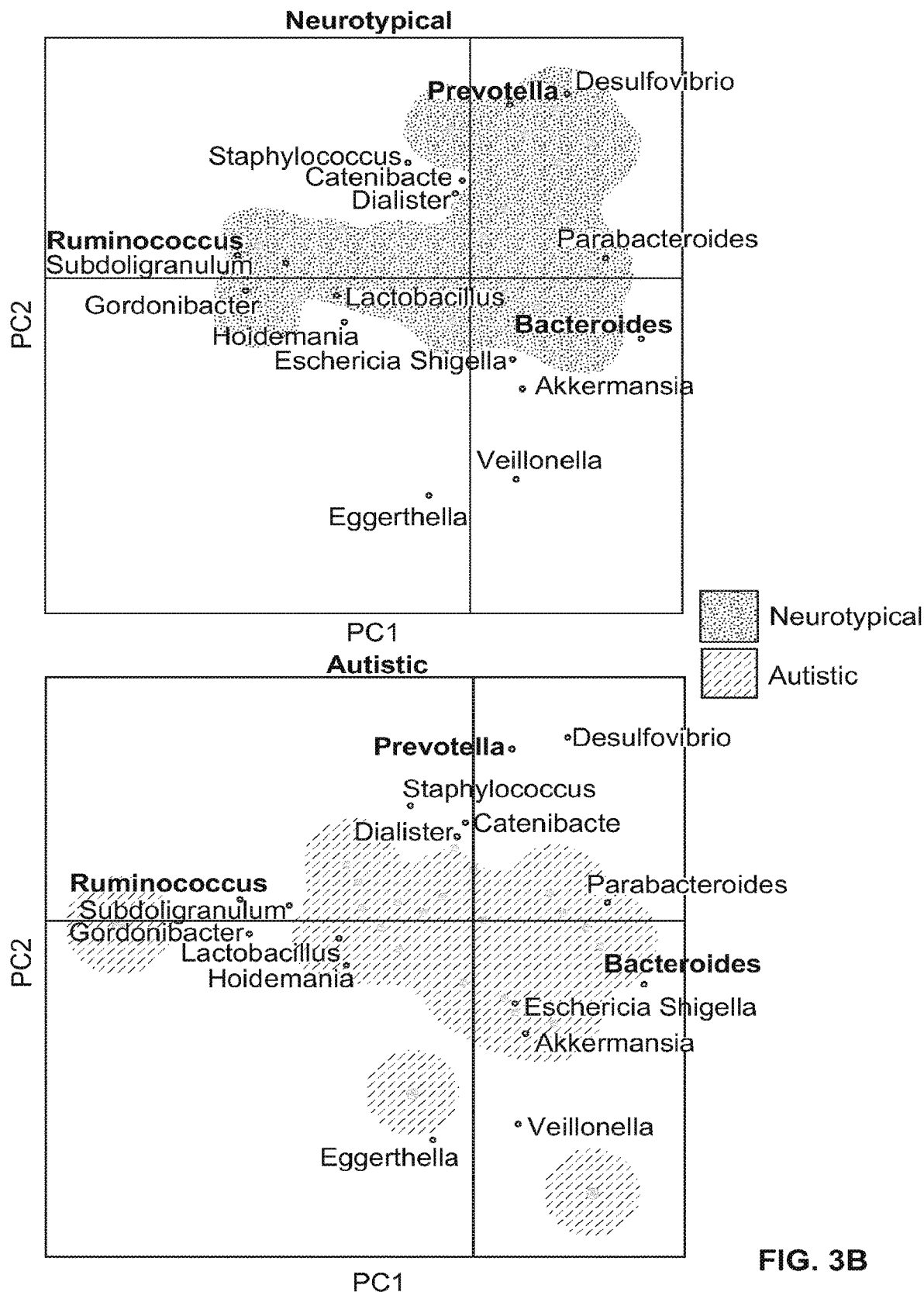
FIG. 3B shows Principal Component Analysis at the genus level from the neurotypical group and the autistic group, both with and without GI problems. Three genera representing enterotypes are identified in bold (*Prevotella, Ruminococcus,* and Bacteroides).
Figure 9:
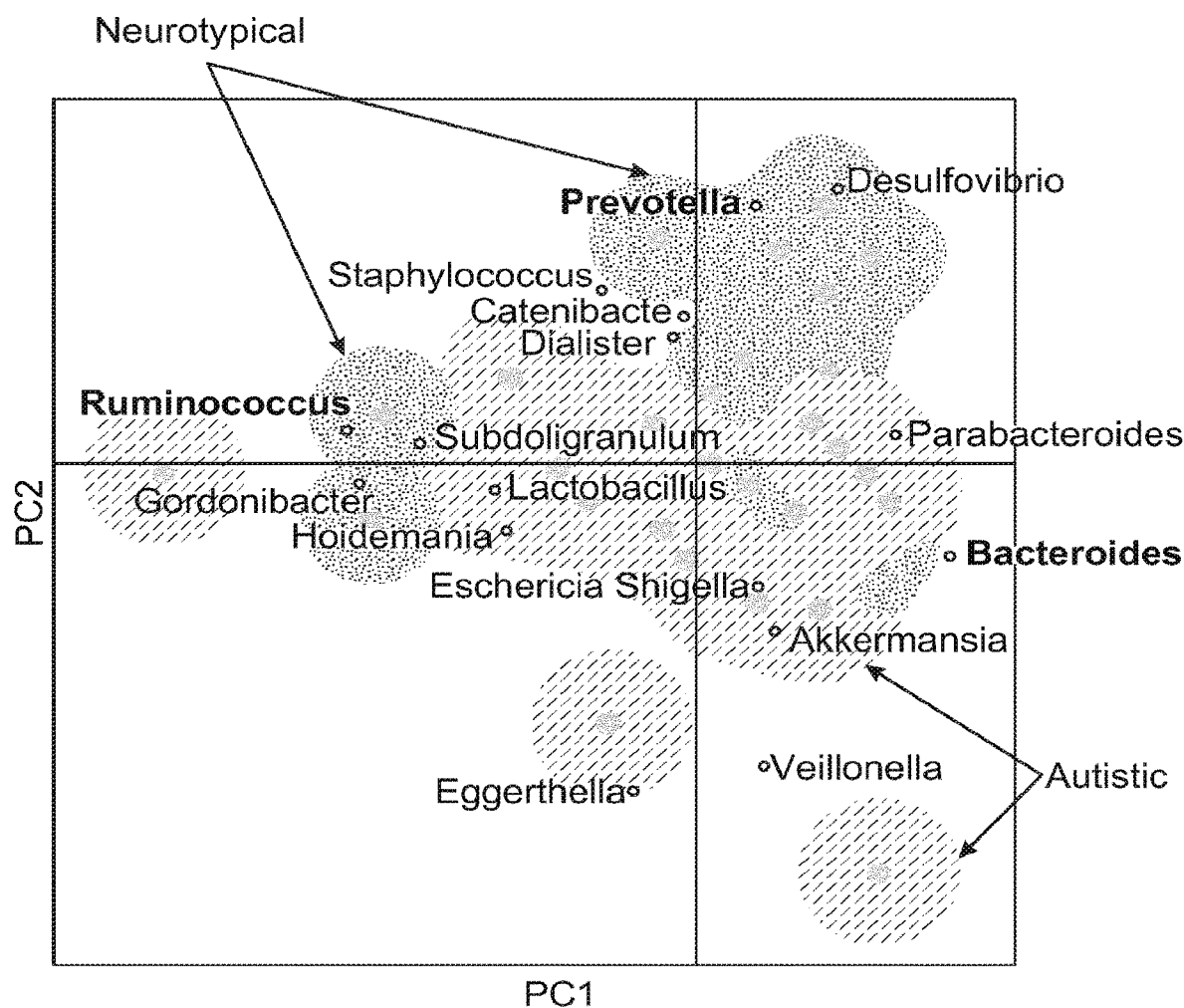
FIG. 9 illustrates an overlapped graph of the Principal Component Analyses of FIG. 3B.

†used for the present PCA analysis. The remaining genera were not considered because of no/little observation through the samples Three core genera of enterotypes (e.g., *Prevotella*, *Bacteroides*, and *Ruminococcus*) were also among the main contributors of the first and the second principal components (FIGS. 3B and 9, Table 13).

TABLE 13

Genera considered for principle component analysis.

| Genera | PC1 | PC2 |
| --- | --- | --- |
| Bacteroidaceae.*Bacteroides* | −0.35† | −0.13 |
| Coriobacteriaceae.*Eggerthella* | 0.08 | −0.48† |
| Coriobacteriaceae.*Gordonibacter* | 0.46† | −0.03 |
| Desulfovibrionaceae.*Desulfovibrio* | −0.19 | 0.40† |
| Enterobacteriaceae.*Escherichia/Shigella* | −0.09 | −0.18 |
| Erysipelotrichaceae.*Catenibacterium* | 0.02 | 0.22 |
| Erysipelotrichaceae.*Holdemania* | 0.26 | −0.10 |
| Lactobacillaceae.*Lactobacillus* | 0.27 | −0.04 |
| Porphyromonadaceae.*Parabacteroides* | −0.27† | −0.04 |
| Prevotellaceae.*Prevotella* | −0.08 | 0.38† |
| Ruminococcaceae.*Ruminococcus* | 0.47† | 0.05 |
| Ruminococcaceae.*Subdoligranulum* | 0.38 | 0.03 |
| Staphylococcaceae.*Staphylococcus* | 0.13 | 0.25 |
| Veillonellaceae.*Dialister* | 0.03 | 0.19 |
| Veillonellaceae.*Veillonella* | −0.09 | −0.44† |
| Verrucomicrobiaceae.*Akkermansia* | −0.11 | −0.24 |

†Main contributors of respective principal component

Surprisingly, when the frequencies of enterotypes were compared between groups, the '*Prevotella*-like enterotype' was absent in the autistic group, while neurotypical samples showed an even distribution among three enterotypes. Furthermore, it appeared that the severity of GI symptoms did not influence the enterotype profile within the autistic group (FIG. 9). Taken together with clustering analyses, these data demonstrate that autistic children have a very distinct gut microbial community structure, which is more profoundly associated with the presence of autistic symptoms than with having GI problems.

Figure 4A:
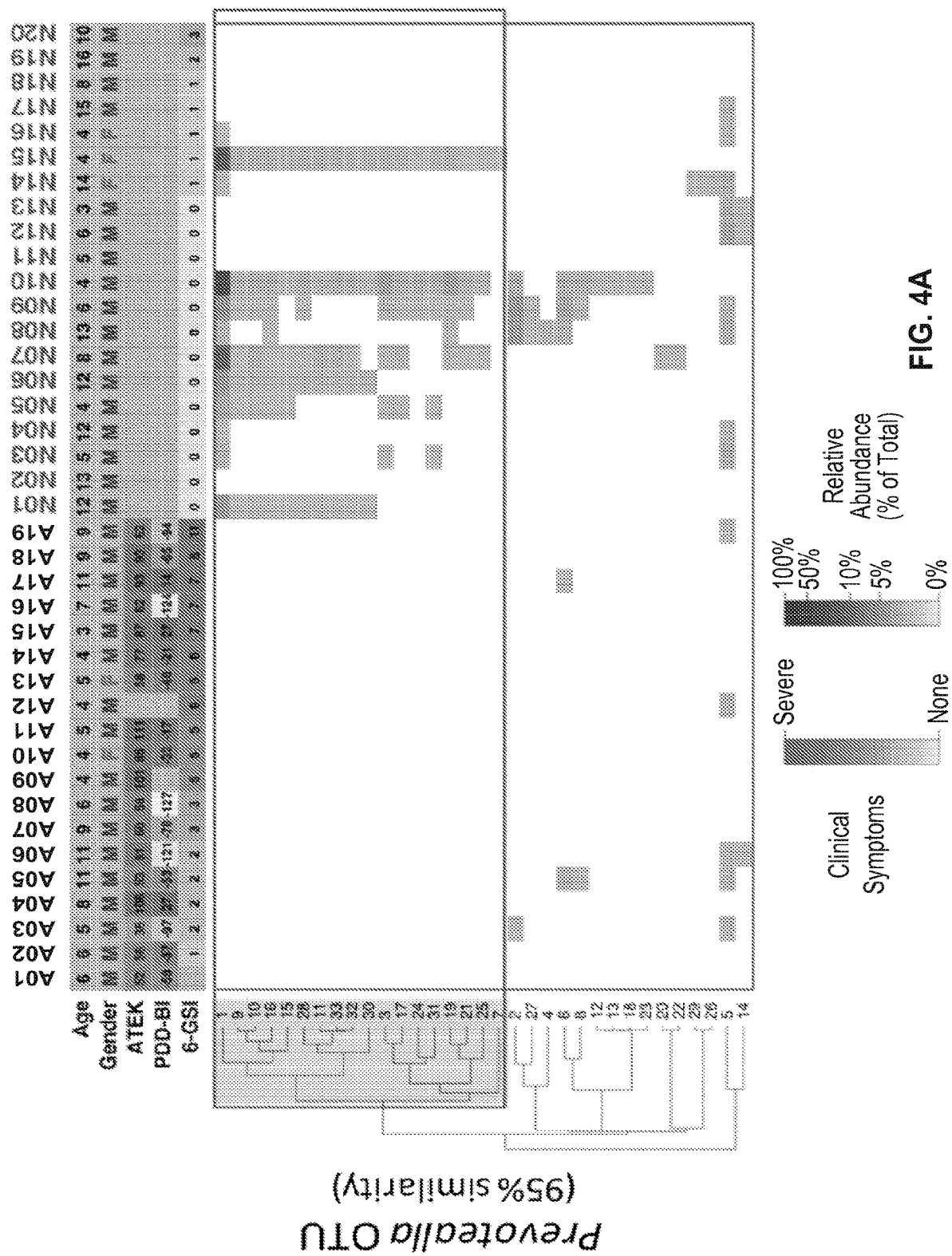
FIG. 4A is a heatmap profile and dendrogram within the genus *Prevotella* (OTUs with 95% threshold) (A01-A11: autistic children with GI problems; A12-A19: autistic children without GI problems; N01-N20: neurotypical children). A scale bar represents a log scale of the percentile abundance from the total bacteria.
Figure 4B:
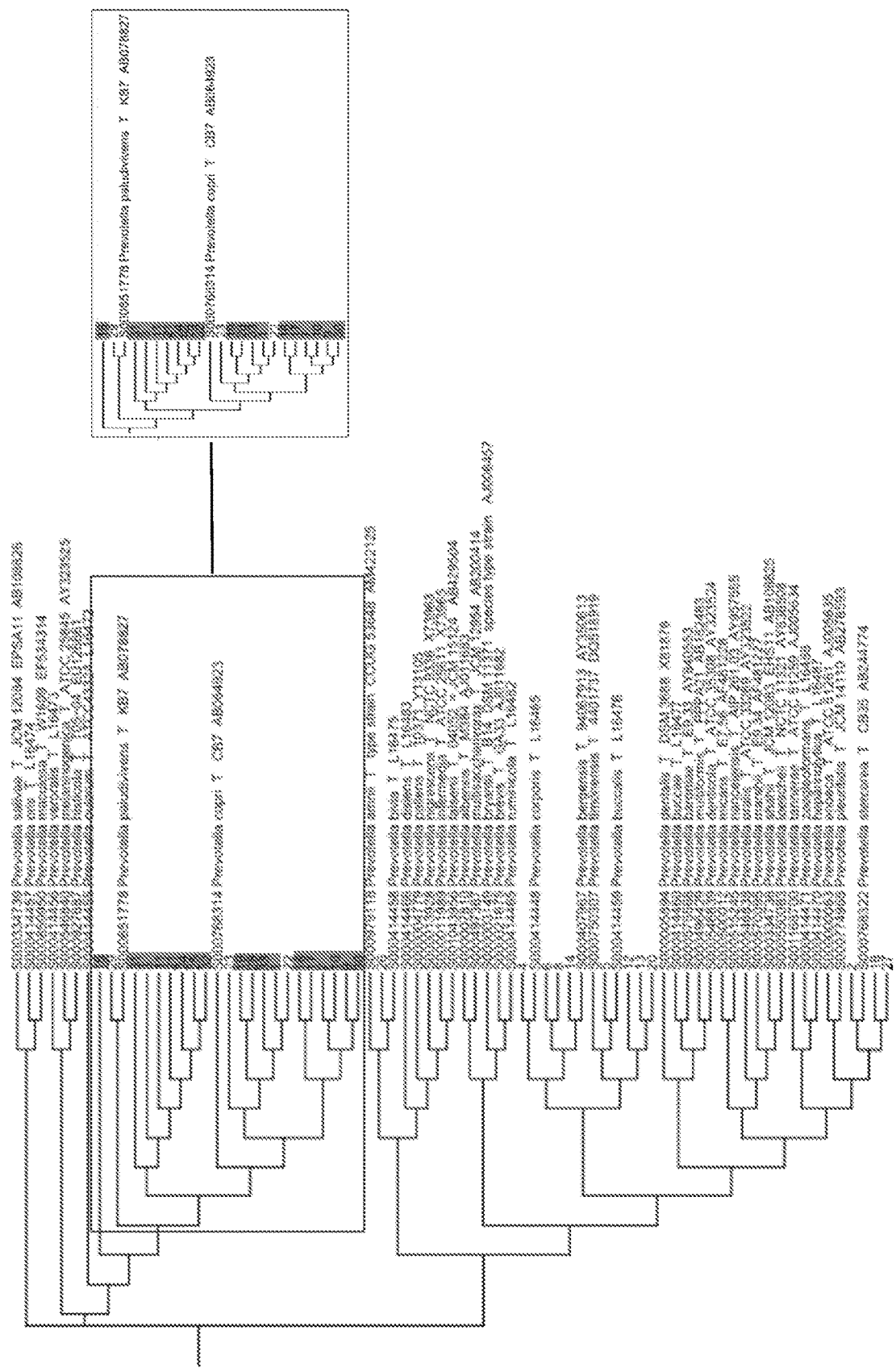
FIG. 4B is a phylogenetic tree within the genus *Prevotella*.

Further characterization of the microbiome included a species-level analysis of *Prevotella*. Most of the 16S rRNA-based metagenomic analyses were done at a genus level due to a low confidence level of classification by using a limited length of sequence reads. Because it is highly likely, however, that a given genus contains multiple species or strains, the genus-level interpretation may suffer intrinsic noise derived from the heterogeneity of data. Therefore, because of the importance of the *Prevotella* genus in the present study, a more in-depth conclusion from the sub-genus level analyses might be inferred. First, all sequences that belonged to *Prevotella* were re-classified into discrete OTUs at an about 95% similarity level by the UCLUST algorithm. The thirty-three identified OTUs were then clustered based on their relative abundance across samples and visualized as a heat map (FIG. 4A). Noticeably, a major cluster of 18 OTUs was exclusively present in neurotypical samples (FIG. 4A), while the other OTUs showed a scattered distribution in both groups. Thus, the *Prevotella* genus in the samples likely consisted of at least two distinct species, and the major cluster of eighteen OTUs dominantly contributed to the abundance difference between neurotypical and autistic groups. In order to see if these OTUs represented any known species, the OTU sequences were then combined with 16S rRNA sequences of forty-two known type-cultured *Prevotella* species, and a phylogenic analysis by multiple alignments was performed. The dendrogram showed that twenty-one *Prevotella* OTUs had higher sequence similarities to *Prevotella copri* and *Prevotella paludivivens* (FIG. 4B). When the OTUs were cross-matched between two independently generated clusters (i.e., based on their relative abundance vs. sequence similarities), surprisingly, all of the eighteen OTUs in the major cluster identified in FIG. 4A were mapped to the sequence cluster that contained *P. copri* and *P. paludivivens* (FIG. 4B). These data strongly suggest that autistic children have significantly low levels of these two or other closely-related *Prevotella* species in their GI tracks, while those species are more frequently found in neurotypical children.

Given the crucial role of gut microorganisms in maintaining GI health, increasing evidence of more frequent occurrence of GI problems in autistic children strongly implies a link between autism and gut microbiota. Although direct causality between autism and GI complications is still unclear, it is important to identify the specific microorganism(s) that can be targeted for diagnosis as well as for treatment of autism-related GI problems and, possibly, other autistic symptoms. As a stepping-stone to reach this long-term goal, the studies described herein compared the composition of intestinal microbiota between neurotypical and autistic children by 16S rRNA-based pyrosequencing and discovered several key differences: (1) autistic children tend to have less a diverse gut microbiome; (2) several individual genera, most notably *Prevotella*, are found at a significantly lower abundance in autistic children; and (3) there are autism-associated global changes (e.g., enterotype profiles) in the intestinal microbial community.

Samples from neurotypical children had higher richness and diversity than the samples from autistic children. As such, higher diversity of gut bacteria may allow better microbial integrity and ability to protect the human intestine from pathogenic gut microbes. It has also been observed in that rural African children tend to have a higher diversity of gut bacteria than European children. It has been hypothesized that the typically fiber-rich diet of African children provided greater resistance to disorders such as diarrhea than the typically lower-fiber diets of European children. A metagenomic analysis showed about 25% fewer genes in the gut of irritable bowel syndrome patients than in the healthy controls. In contrast, a higher diversity has been recorded in children with autism versus neurotypical children. The higher diversity in autistic children was attributed to an increase of pathogenic bacteria. Neurotypical children with higher bacterial richness and diversity are possibly favored, however, by a microbial defense mechanism and may be less vulnerable to bacterial infections that may trigger sudden GI symptoms and neurological problems, such as the increase of anxiety-like behavior by a food-born pathogen.

Through a series of screening tests described herein, a long list of genera was narrowed, and the findings related to the genus *Prevotella* brought worthy insights into the gut microbiota. The detected *Prevotella* species, most closely related to *P. copri* or *P. paludivivens*, were exclusively present in the neurotypical children (FIG. 4B). *Prevotella* was popularized as an oral pathogen and also as a commensal microbe in human large intestines, pig intestines, and the rumen of cattle.

The role of *Prevotella* species in human large intestine has brought more attention because of its ability to degrade a broad spectrum of plant polysaccharides. *Prevotella* species were prevalent in African children who often have a plant-polysaccharide rich diet, which implies that *Prevotella* play a key role in extracting energy from a specific diet. Previous results show that carbohydrate-based diets shift intestinal microbiota towards the *Prevotella*-enterotype. The near absence of *Prevotella* in autistic children suggests that autistic children may have different diet habits, such as less plant-based carbohydrate compared with neutropical subjects (e.g., gluten/casein free diet for autistic children). In fact, autistic children are often known to have significant deficiencies of dissacharides, especially lactase in the upper GI track. In addition, *Prevotella* was one of many dominant gut microbes in individuals whose diets included fish-oil. Fish-oil is a precursor of omega-3 fatty acids, and the high level of omega-3 is helpful to normal brain development. *Prevotella* species may also have a metabolic link to vitamin B1 production, which is beneficial to mitigate ASD because enzymes related to vitamin B1 biosynthesis were overrepresented when *Prevotella* species was enriched. Although these commensal microbes have not been previously linked to autism, the carbohydrate content in diets of autistic children may exert a profound effect on the composition of gut microflora, and, consequently, their GI health. The present disclosure supports a correlation between *Prevotella* and the diets of autistic children.

The prevalence of *Akkermansia* in several autistic subjects also warranted attention (FIG. 7). Although *Akkermansia* is not a generally-known pathogen and is actually considered as a biomarker as a good condition in gut health, it is able to degrade mucins in the large intestine. Therefore, the extremely high abundance of *Akkermansia* may cause increased intestinal permeability and, consequently, a higher chance of developing GI problems such as infection, as previously reported in some children with autism. As discussed herein, a correlation between the abundance of *Akkermansia* and the severity of GI problems was not found.

As presented herein, the cluster analysis and PCA identified a meaningful relation between autism and gut microbe communities. The enterotype approach accounts for the unique position of *Prevotella* in autism-associated changes in gut microflora. Moreover, the network surrounding *Prevotella* species also corresponds to previous human gut studies. In detail, the *Prevotella*-cluster, as shown in FIG. 3, includes a group of noteworthy genera *Desulfovibrio, Oscilibacter*, and *Coprococcus* that were significantly more abundant in the neurotypical group than in the autistic group. It is contemplated that *Desulfovibria* species may work synergistically with *Prevotella* species to degrade mucin. *Desulfovibrio, Prevotella*, and *Oscilibacter* also use microbial exopolysaccharides (EPS) synthesized by *Bifidobacterium* to produce short-chain fatty acids (SCFAs) in the human intestine. *Coprococcus* species are butyrate-producing bacteria that belong to *Clostridium* XIVa of the family Lachnospiraceae, and may be beneficial to sustain mucosal health of neurotypical children. Meanwhile, the *Enterobacteriaceae* cluster possesses an opposite trend of abundance to the *Prevotella*-cluster among the neurotypical group. The *Enterobacteriaceae* cluster included several potentially pathogenic genera—*Salmonella, Escherichia/Shigella*, and *Citrobacter* which has appeared along with *Prevotella* species. A significantly low abundance of *Escherichia/Shigella* in African children has generally been observed. The generally low occurrence of GI disorders in African children has been attributed to the suppression of pathogenic *Escherichia/Shigella* by *Prevotella*, and the genus *Escherichia/Shigella* showed a negative correlation with the genus *Prevotella* in the co-occurrence network. This negative correlation disappeared in the autistic group, however, which implicated the possibility of altered microbial networks in the gut of autistic children. Previously, it was found that the core genera of the enterotypes were independent to factors such as body mass index (BMI) and inflammatory bowel disease. Surprisingly, certain enterotypes can be linked to a human disorder, as the present disclosure has done.

The present disclosure also contradicts with studies and general beliefs in the field of neurobiology or nutritional physiology. For example, as described herein, there was no significant difference of Bacteroidetes and *Firmicutes* between neurotypical and autistic children. Previous studies, on the other hand, reported significantly higher levels of *Firmicutes* and lower levels of Bacteroidetes in neurotypical children over autistic children. Further, other studies showed an opposite trend in ileum and cecum biopsy samples when they compared neurotypical and autistic children, both with GI problems. Additionally, analysis of biopsy samples revealed the genus *Sutterella* to be predominant in autistic children with GI problems compared to neurotypical children with GI problems. Here, however, a relatively lower abundance of the genus *Sutterella* was found in fecal samples of autistic children compared with neurotypical ones. Differences in sample characteristics (feces versus biopsies), human sampling (subject characteristics), experimental methods (e.g., PCR primer selection), and types of statistical tests used to analyze the data may have affected the results. Thus, the present disclosure has used rigorous correction methods for multiple testing. Pyrosequencing using different primer sets and quantifying genes by quantitative PCR, as shown herein, can fortify the understanding of microbial community.

By way of summary, autistic children have been shown to have distinct gut microflora, which can be characterized by a reduced richness, as well as significant alterations in composition and structure, of the microbial community. Furthermore, gut microbiota seems to have a close association with autistic symptoms but not with GI problems. Notably, the unique absence of *Prevotella* in the autistic group compared to the neurotypical group led suggests *Prevotella* as a potential probiotic or "health specific" biomarker. The list of significant microorganisms determined herein provides a better understanding of the association between gut microbiota and autism and potential targets for diagnosis or treatment.

The present aspects provide for the characterization of the normal flora in the GI tract and/or gut of healthy, neurotypical subjects, and identifying biomarkers for a healthy gut microbiome. In particular, one embodiment provides for the characterization of the gut microbiome in ASD subjects, which microbiome differs from that of neurotypical subjects. Namely, autistic children tend to harbor a unique gut flora compared to neurotypical children, characterized by reduced richness and significant loss of the genus *Prevotella*. In addition to *Prevotella*, the relative abundance of genera *Coprococcus, Prevotellaceae*, and *Veillonellaceae* were also significantly lower in autistic children than in neurotypical children. Further, *Prevotella*, a versatile carbohydrate-degrading microbe, has been reported as one of the three main classifiers for the human enterotypes, along with Bacteroides and *Ruminococcus*. These three core genera were among the main contributors in the principle component analysis. '*Prevotella*-like enterotype' was absent in the autistic group, while neurotypical samples showed an even distribution among three enterotypes, which suggests an altered ability to digest carbohydrates in the autism group.

The present aspects provide for an understanding of the association between gut microbiota, health, and disease states. The present aspects also provide for potential diagnostic and therapeutic targets. More specifically, for example, *Prevotella* can serve as a "healthy gut" biomarker and as a probiotic to improve human gut function and health.

Thus, disclosureone aspect of the processes described herein provides for modifying the intestinal microbiota as a means to establish a neurotypical/healthy profile or as a means for alleviating ASD or ASD symptoms, including GI disorders in ASD subjects. In some aspects, a probiotic therapy is administered as an exemplary embodiment that achieves these goals comprises administering to a subject a composition comprising *Prevotella, Coprococcus, Prevotellaceae*, and/or *Veillonellaceae*. In some aspects, as a probiotic therapy. Another embodiment provides for the ingestion of prebiotics are ingested in the form of non-digestible foods that support the growth and metabolism of these organisms. For example, *Prevotella* can be obtained, for example, from commercial sources such as the AMERICAN TYPE CULTURE COLLECTION® (ATCC, Manassas, VA) and cultured anaerobically, e.g., in tryptone-based media, or grown in a ruminant gut and harvested therefrom. *Prevotella* may be provided as a probiotic in means as known in the art, for example, as described in Vidhyalakshmi et al., "Encapsulation 'The Future of Probiotics'— A Review," 3 Adv. Biol. Res. 96 (2009), which is hereby incorporated by reference in its entirety.

Another embodiment provides for the act of ingesting agents (such as antibiotics) that affect the microbiota of the gut. For example, agents that inhibit the growth of microbes present in the ASD microbiome at levels higher than those found in the neurotypical microbiome may be administered. If agents of sufficient specificity are not available, broad spectrum antibiotics may be used in conjunction with probiotic therapy to disrupt the flora of the ASD subject and repopulate the gut with neurotypical flora. In other words, broad-spectrum antibiotics of may be used where probiotics are reintroduced either concurrently, regularly, or subsequently to replace the bacteria killed by the antibiotics. An example antibiotic is the semi synthetic, rifamycin-based, non-systemic antibiotic rifaximin (XIFAXAN®, Salix Pharmaceuticals, Inc., Morrsiville, NC), that is essentially non-absorbed from the gut and is being employed for certain gastrointestinal problems. The antibiotic therapy may be long-term or short-term, depending on the maintenance or establishment of the desired microbiota or the obesity management goals of the subject in consultation with the physician. The efficacy of this approach may be monitored by known laboratory and clinical techniques, and may be adjusted accordingly. Other agents that target specific enzymes or pathways of target bacteria include iRNAs, small molecules, combinations thereof, or the like.

As used herein, the terms "treating," "treatment", and "to treat" are used to indicate the production of beneficial or desired results, such as to alleviate symptoms, or eliminate the causation of a disease or disorder (either on a temporary or a permanent basis), slow the appearance of symptoms and/or progression of the disorder, and/or prevent progression of disease. For methods of prevention, a subject to be administered the treatment (e.g., probiotic therapy) is generally a subject having ASD or at risk for ASD and/or pure gut health. The terms "treat" or "treatment" may refer to both therapeutic treatment and prophylactic or preventative measures, wherein the object is to prevent or slow the development of ASD-gut related symptoms. Beneficial or desired clinical results include, but are not limited to, alleviation of symptoms, diminishment of extent of autism, stabilized (i.e., not worsening) state of the ASD-gut-related or GI involvement, delay, or slowing of disease progression, amelioration or palliation of the disease state.

Additionally, therapy or treatment can be measured by monitoring the intestinal biome and/or monitoring the organisms identified herein as associated with ASD versus neurotypical flora. Such an "effective regimen" may be administered over an effective course (a sufficient treatment and/or amount of treatment over a sufficient period of time) to achieve a microbial biome in the body sufficient for increasing bacteria (e.g., *Prevotella*) identified herein as a biomarker of neurotypical flora lacking in ASD subjects or to reduce the relative concentration of bacteria identified as increased in ASD subjects.

The examples below are intended to illustrate the embodiments of the present invention to one of ordinary skill in the art and should not be interpreted as limiting the scope of the invention set forth in the claims.

EXAMPLES

Example 1. Subject Recruitment and Characteristics

Fifty-six (56) applicants, which included thirty (30) neurotypical and twenty-six (26) autistic subjects ranging from 3 to 15 years of age, were enrolled. Neurotypical children that were first-degree relatives of children with ASD were excluded. The twenty-six children with Autism Spectrum Disorders (ASD) were assessed with the Autism Diagnostics Interview Revised (ADI-Revised) and the Autism Diagnostics Observation Schedule (ADOS) to confirm their autism diagnosis. The Autism Treatment Evaluation Checklist (ATEC) and Pervasive Developmental Disorder Behavior Inventory (PDD-BI) assessments were also used to evaluate autism severity. The ATEC consists of four subscales: (1) speech/language/communication; (2) sociability; (3) sensory/cognitive awareness; and (4) health/physical behavior. The total ATEC score is the sum of the scores from each subscale. For PDD-BI scores, a modified "Autism Composite" was determined based on the addition of scores from three subscales-"sensory/perceptual approach behaviors," "ritualisms/resistance to change," and "social pragmatic problems." Scores from "social approach behaviors" and "expressive language" were then subtracted. Higher ATEC and PDD-BI scores indicate more severe ASD.

Also assessed were the gastrointestinal symptoms of the children with a modified version of the Gastro-Intestinal Severity index (GSI) questionnaire. The GSI subscales included six categories of symptoms (constipation, diarrhea, stool consistency, stool smell, flatulence, and abdominal pain). Each category had a 3-point scale and summed up the points to get the total six GI Severity Index (6-GSI). The excluded subscales were "unexplained daytime irritability," "nighttime awakening," and "abdominal tenderness."

Out of the initial twenty-six autistic subjects enrolled, six children were excluded from the further data evaluation: (1) two children who did not meet the ADOS criteria described above; (2) two children who received antibiotic/antifungal treatment during the previous month; (3) one child who did not sufficiently submit required information; and (4) one child who dropped out. Out of the initial thirty neurotypical subjects enrolled, one subject was excluded because of improper sample shipment, and nine female children were not included to balance the number of gender with autistic children. The final forty participants are listed in the Table 14 below.

TABLE 14

Characterization of participants

| | Neurotypical | Autism-GI⁻ | Autism-GI |
|---|---|---|---|
| Total # participants | 20 | 12 | 8 |
| Male/Female | 17/3 | 11/1 | 7/1 |
| Age (years) | 8.3 ± 4.4 | 7.5 ± 3.4 | 6.5 ± 2.9 |
| ATEC | — | 71.5 ± 24.2 | 72.1 ± 21.8 |
| PDD-BI | — | −56 ± 46.8 | −43.3 ± 55.2 |
| 6-GSI | 0.5 ± 0.8 | 3.1 ± 1.4 | 7.0 ± 1.1 |

Autism-GI+ autistic children with severe GI problems;
Autism-GI⁻ autistic children without severe GI problems Example 2. Sample Collection and DNA Extraction Parents collected and froze a single fecal sample from each subject. Frozen fecal samples were shipped overnight to Arizona State University with a cold pack, and stored in a temperature of about 80° C. until DNA extraction. Genomic DNA was isolated from human stool samples (wet weight: about 1.0 g) using QIAamp DNA Stool Mini Kit (Qiagen, CA) following the manufacturer's instructions. The quantity and quality of DNA were assessed by measuring the absorbance at about 260 nm and about 280 nm using a NanoDrop ND-1000 spectrophotometer (NanoDrop Technology, Rockland, DE) and agarose gel (about 1%, w/v) electrophoresis.

Example 3. Pyrosequencing Analysis of Community Structures

Extracted genomic DNA was processed at the Research and Testing Laboratory (Lubbock, TX), where the bacterial tag-encoded FLX amplicon pyrosequencing (bTEFAP) was performed by the Genome Sequencer FLX-Titanium System and its Titanium protocol (Roche, Indianapolis, IN), as described in Sun et al., in "Tag-Encoded FLX Amplicon Pyrosequencing for the Elucidation of Microbial and Functional Gene Diversity in Any Environment" METHS. MOLEC. BIO. 129, which is hereby incorporated by reference for its Methods and analysis of pyrosequencing. Bacterial primers 104F (5'-GGCGVACGGGTGAGTAA-3') (SEQ ID NO:1) and 530R (5'-CCGCNGCNGCTGGCAC-3') (SEQ ID NO:2) were used to amplify the combined V2 and V3 regions of 16S rRNA, and the amplicon was sequenced by the procedure described in Wolcott et al., "Evaluation of the bacterial diversity among and within individual venous leg ulcers using bacterial tag-encoded FLX and Titanium amplicon pyrosequencing and metagenomic approaches," 9 BMC Microbiol. (2009), which is hereby incorporated by reference in its entirety. Unqualified sequences were eliminated as described in Garcia-Pena et al., "Anaerobic digestion and c-digestion processes of vegetable and fruit residue," 102 Bioresource Tech. 9447 (2011), which is hereby incorporated by reference in its entirety, and after excluding sequences shorter than 200 bp, about one million non-chimeric sequences, in total, from all forty samples, were obtained, and most samples yielded more than 20,000 sequences (Table 15). It is contemplated that other sequences may be used. Such sequences are available from publicly available resources such as the Green Genes database available at greengenes.lbl.gov:

TABLE 15

High-throughput pyrosequencing data summary and OTUs defined by 95% similarity.

| Subject ID | Subject description | Total Sequences # | Qualified Sequences # | OTUs | Chao1 estimate |
|---|---|---|---|---|---|
| N1 | Neurotypical (N) | 56659 | 27186 | 1116 | 1618 |
| N2 | N | 50072 | 27258 | 784 | 1108 |
| N3 | N | 51837 | 23746 | 1580 | 2439 |
| N4 | N | 57447 | 25463 | 1020 | 1395 |
| N5 | N | 52997 | 21863 | 704 | 1040 |
| N6 | N | 54602 | 21141 | 1313 | 1876 |
| N7 | N | 52987 | 26326 | 732 | 960 |
| N8 | N | 79139 | 46701 | 678 | 977 |
| N9 | N | 51470 | 22064 | 1049 | 1377 |
| N10 | N | 53466 | 22213 | 845 | 1136 |
| N11 | N | 63879 | 26188 | 1292 | 1821 |
| N12 | N | 48537 | 21381 | 711 | 980 |
| N13 | N | 35607 | 17156 | 868 | 1293 |
| N14 | N | 53791 | 20094 | 852 | 1108 |
| N15 | N | 47146 | 19328 | 1169 | 1601 |
| N16 | N | 47295 | 25287 | 556 | 701 |
| N17 | N | 75380 | 43412 | 346 | 427 |
| N18 | N | 52168 | 23583 | 514 | 702 |
| N19 | N | 55706 | 27099 | 438 | 598 |
| N20 | N | 52407 | 25617 | 492 | 605 |
| A1 | Autistic without GI problems (A-GI⁻) | 36430 | 17687 | 428 | 587 |
| A-excl. | A-GI⁻ (excluded subject) | 50829 | 8830 | 176 | 266 |
| A2 | A-GI | 51190 | 29633 | 860 | 1156 |
| A3 | A-GI | 49703 | 32744 | 527 | 673 |
| A4 | A-GI | 44868 | 21717 | 812 | 1086 |
| A5 | A-GI | 48341 | 19575 | 465 | 641 |
| A6 | A-GI | 60063 | 24336 | 434 | 557 |
| A7 | A-GI | 49571 | 15991 | 614 | 816 |
| A8 | A-GI | 43171 | 16267 | 627 | 826 |
| A9 | A-GI | 59110 | 30088 | 886 | 1241 |
| A10 | A-GI | 53074 | 20344 | 462 | 627 |
| A11 | A-GI | 55065 | 29424 | 593 | 717 |
| A12 | Autistic with GI problems (A-GI⁺) | 54599 | 25731 | 354 | 411 |
| A13 | A-GI⁺ | 60877 | 28639 | 856 | 1256 |
| A14 | A-GI⁺ | 60902 | 28284 | 1066 | 1503 |
| A15 | A-GI⁺ | 59135 | 30979 | 747 | 973 |
| A16 | A-GI⁺ | 55105 | 27784 | 488 | 646 |
| A17 | A-GI⁺ | 48550 | 19213 | 447 | 681 |
| A18 | A-GI⁺ | 49048 | 20954 | 768 | 1031 |
| A19 | A-GI⁺ | 58397 | 26475 | 599 | 833 |

To obtain the operational taxonomic units (OTUs), the sequencing readouts were clustered at about 90%, 95%, 97%, and 99% similarity with the UCLUST algorithm described in Edgar, "Search and clustering orders of magnitude faster than BLAST," 26 Bioinformatics 2460 (2010), which is hereby incorporated by reference in its entirety.

Thisese percentages are roughly equivalent to the taxonomic terms of family, genus, species, and strain, respectively. Mothur software, described by Schloss et al., "Introducing mothur: Open-Source, Platform-Independent, Community-Supported Software for Describing and Comparing Microbial Communities," 75 Appl. Environ. Microbiol. 7537 (2009), which is hereby incorporated by reference in its entirety, was used to obtain ecological indices of Chao1 estimator and Shannon diversity/richness indices. Finally, sequences were classified by the RDP Classifier software at an about 50%- and about 80%-confidence threshold for sequence length less than about 250 bp and more thanabout 250 bp, respectively.

Regarding statistical and data analysis, amplicon numbers from each sample were individually normalized to a percentage of total sequences before statistical analyses. Student's t-test and Mann-Whitney test were performed with SciPy library for Python, and the P values were then adjusted for multiple testing by p.adjust function (method=the Benjamini-Hochberg method) in the package that R programming provides (ver.2.11.1). Hierarchical clustering (complete linkage) was performed with a Biopython package, and clustergrams were generated by the Reportlab package for Python (ver.2.6.5). ROC curves and AUC values were obtained using the caTools package in R. Principal, and component analysis was performed using the prcomp function (scaled and centered) in R, from which the coordinates for genus and samples were obtained.

Example 4. Quantitative Real-Time PCR Analysis 16S rDNA-targeting quantitative real-time PCR (qPCR) with triplicate PCR reactions in an REALPLEX® 4S Real-Cycler (Eppendorf AG, Hamburg, Germany). were performed For *Prevotella* species, a seven-point standard curve was constructed using genomic DNA of *Prevotella copri* (DSM18205). The PCR reagent mixture for each reaction was about 20 μL of including about 84 of 2.5×SYBR Premix Ex Taq Mix (Takara Bio Inc, Japan), about 1 μL, of about 10 μL *Prevotella*-specific forward and reverse primers, as described in Larsen et al., "Gut Microbiota in Human Adults with Type 2 Diabetes Differs from Non-Diabetic Adults."6 Plos One 5 (2010), which is hereby incorporated by reference in its entirety, about 2 pL 10-fold diluted DNA as a template, and about 8 pL PCR grade water. The PCR amplification was conducted with an initial about 10 minute denaturation at about 95° C., followed by about 35 cycles of denaturation (at about 95° C. for about 15 s), and annealing/extension (60° C. about for about 60 s). For general bacteria, qPCR was performed following the protocols described in Ziv-El et al. "Development and characterization of DehaloRA2, a novel anaerobic microbial consortium performing rapid dechlorination of TCE to ethane," 92 Appl. Microbio. & Biotech. 1063-71 (2011), which is hereby incorporated by reference in its entirety.

Alternative Embodiment a

In at least one embodiment, a method of detecting, in a stool sample, a relative abundance of *Prevotella, Coprococcus, Prevotellaceae*, or *Veillonellaceae* bacteria that are indicative of autism spectrum disorders (ASD) includes determining the relative abundance of *Prevotella, Coprococcus, Prevotellaceae*, or *Veillonellaceae* bacteria in the stool sample, wherein a decreased relative abundance of *Prevotella, Coprococcus, Prevotellaceae* or *Veillonellaceae* bacteria relative to a neurotypical population of said bacteria relative to a neurotypical population of said bacterium, is indicative of pure gut health and/or ASD-gut related problems.

Alternative Embodiment B

In at least one embodiment, a method of detecting, in a stool sample, the relative abundance of *Prevotella*-genus, which is indicative of ASD-gut related problems includes determining the relative abundance of *Prevotella*-genus bacteria in a test stool sample, wherein a decreased relative abundance of *Prevotella*-like enterotype bacteria relative to a neurotypical relative abundance of said bacteria is indicative of ASD.

Alternative Embodiment C

In at least one embodiment, the determining comprises obtaining nucleic acids from said stool sample and sequencing with any deep sequencing technique (e.g., 454 pyrosequencing, illumine, ion torrent) the nucleic acids.

Alternative Embodiment D

In at least one embodiment, the nucleic acids to be sequenced are bacterial 16S rRNA genes.

Alternative Embodiment E

In at least one embodiment, an assay comprises a set of primers that allow for the detection of a relative abundance *Prevotella*-genus in a biological sample. The primers may include, for example, a mixture of primers directed to the 16S rRNA species for *Prevotella* or the like. The absence of *Prevotella*-genus relative to a healthy relative abundance of said bacteria is indicative of poor gut health.

Alternative Embodiment F

In at least one embodiment, a method for quantifying the population of *Prevotella, Coprococcus, Prevotellaceae*, or *Veillonellaceae* indicative of ASD includes contacting a stool specimen of a subject with a reagent that detects said bacteria. The method further includes detecting a lower relative abundance of said bacteria compared with the relative abundance of said bacteria in a neurotypical sample being indicative of ASD.

Alternative Embodiment G

In at least one embodiment, a method of treating ASD-gut-related symptoms in a subject in need thereof includes assaying a stool sample from said subject for decreased relative abundance of at least one of *Prevotella, Coprococcus, Prevotellaceae*, or *Veillonellaceae*. The method further includes administering a therapeutically effective amount of probiotic, prebiotic, or pharmaceuticaltherapy to the subject when the at least one of *Prevotella, Coprococcus, Prevotellaceae*, or *Veillonellaceae* is lower than an abundance of said bacteria in a neurotypical population of said bacteria.

Alternative Embodiment H

In at least one embodiment, the assay determines relative abundance of at least one of a group comprising *Prevotella, Coprococcus, Prevotellaceae*, or *Veillonellaceae*.

Alternative Embodiment I

In at least one embodiment, the assay determines relative abundance of at least one of a group consisting essentially of *Prevotella, Coprococcus, Prevotellaceae*, or *Veillonellaceae*.

Alternative Embodiment J

In at least one embodiment, the assay determines relative abundance of at least one of a group consisting of *Prevotella, Coprococcus, Prevotellaceae*, or *Veillonellaceae*.

Alternative Embodiment K

In at least one embodiment, the at least one of *Prevotella, Coprococcus, Prevotellaceae*, or *Veillonellaceae* is at least two of *Prevotella, Coprococcus, Prevotellaceae*, or *Veillonellaceae*.

Alternative Embodiment L

In at least one embodiment, the at least one of *Prevotella, Coprococcus, Prevotellaceae*, or *Veillonellaceae* is at least three of *Prevotella, Coprococcus, Prevotellaceae*, or *Veillonellaceae*.

Alternative Embodiment M

In at least one embodiment, the at least one of *Prevotella, Coprococcus, Prevotellaceae*, or *Veillonellaceae* is all four of *Prevotella, Coprococcus, Prevotellaceae*, or *Veillonellaceae*.

Alternative Embodiment N

In at least one embodiment, the assaying comprises sequencing multiple nucleic acid chains concurrently, for example, 16S rRNA sequences from various species. This comprises contacting the sample with primers that are specific for each species' 16S rRNA gene as are readily available from the publicly available database

Alternative Embodiment O

In at least one embodiment, the at least one of *Prevotella, Coprococcus, Prevotellaceae*, or *Veillonellaceae* is at least one of:
  a. *Prevotella, Coprococcus, Prevotellaceae*, and *Veillonellaceae;*
  b. *Coprococcus, Prevotellaceae*, and *Veillonellaceae;*
  c. *Prevotella, Prevotellaceae*, and *Veillonellaceae;*
  d. *Prevotella, Coprococcus*, and *Veillonellaceae;*
  e. *Prevotella, Coprococcus*, and *Prevotellaceae;*
  f. *Prevotellaceae* and *Veillonellaceae;*
  g. *Coprococcus* and *Veillonellaceae;*
  h. *Coprococcus* and *Prevotellaceae;*
  i. *Prevotella* and *Veillonellaceae;*
  J. *Prevotella* and *Prevotellaceae;*
  k. *Prevotella* and *Coprococcus;*
  l. *Veillonellaceae;*
  m. *Prevotellaceae;*
  n. *Coprococcus;* or
  o. *Prevotella.*

Alternative Embodiment P

In at least one embodiment, 8. The method of claim 7, further comprising administering an agent to inhibit growth of at least one microorganism in the subject, wherein the microorganism is one having a higher relative abundance in a microbiome of ASD subjects compared with a microbiome of neurotypical subjects.

Alternative Embodiment Q

In at least one embodiment, 9. A method for treating ASD-gut related symptoms/complications in a subject comprising: administering probiotic to said subject, wherein said subject, prior to administration, has tested deficient for *Prevotella*, and/or *Coprococcus*, and/or *Prevotellaceae*, and/or *Veillonellaceae*, wherein a deficiency of *Prevotella, Coprococcus, Prevotellaceae*, or *Veillonellaceae* relative to a neurotypical population of said bacteria is indicative of ASD.

Alternative Embodiment R

In at least one embodiment, 10 A method for treating ASD gut related symptoms in a subject comprising: administering a prebiotic that stimulates the growth of *Prevotella*, and/or *Coprococcus*, and/or *Prevotellaceae*, and/or *Veillonellaceae* to said subject, wherein said subject, prior to administration, has tested deficient for *Prevotella*, and/or *Coprococcus*, and/or *Prevotellaceae*, and/or *Veillonellaceae*, wherein a deficiency of *Prevotella, Coprococcus, Prevotellaceae*, or *Veillonellaceae* relative to a neurotypical/healthy population of said bacteria is indicative of pure gut health and/or ASD gut related symptoms/complications.

Alternative Embodiment S

In at least one embodiment, 10. The use of *Prevotella* as biomarker for health of the human gut, wherein the absence or diminished relative abundance of *Prevotella* indicates poor gut health.

Alternative Embodiment T

In at least one embodiment, 11. DNA targeted detection methods for any of the above claims above can be extended to be: qPCR, RT-qPCR, clone libraries, DGGE, T-RFLP, ARISA, microarrays, FIFH, dot-blot hybridization, and any other DNA hybridization methods that will detect a specific sequence in *Prevotella, Coprococcus, Prevotellaceae*, or *Veillonellaceae*.

Alternative Embodiment U

In at least one embodiment, 12. Protein detection methods for any of the above claims such as 2-Dimensional Gel Electrophoresis (2D-GE), Difference Gel Electrophoresis (2D-DIGE), MALDI TOF-MS, (2D-) LC-ESI-MS/MS, AQUA and iTRAQ, can also be applied to detect multiple or a specific protein in *Prevotella, Coprococcus, Prevotellaceae*, or *Veillonellaceae*.

---

The invention claimed is:

1. A method of treating Autism Spectrum Disorder in a human subject in need thereof, comprising:
   a. determining or having determined abundance of a bacteria in the genus *Prevotella* in a fecal microbiota obtained from the subject;
   b. identifying the subject as having Autism Spectrum Disorder if the subject is determined to have a lower relative abundance of *Prevotella copri* or *Prevotella paludivivens* compared to a neurotypical person; and
   c. administering to the subject a pharmaceutical composition comprising a probiotic that modulates the abundance of the bacteria in the genus *Prevotella* in the subject's fecal microbiota.

2. The method of claim 1, wherein the subject has an Autism Spectrum Disorder associated immune disorder.

3. The method of claim 1, wherein the method increases the abundance of *Prevotella* in the subject's fecal microbiota.

4. The method of claim 1, wherein the method improves one or more symptoms of the subject's Autism Spectrum Disorder.

5. The method of claim 1, wherein the subject further exhibits a gastrointestinal symptom.

6. The method of claim 1, wherein step a. comprises detecting a 16S rRNA nucleic acid of said bacteria in the genus *Prevotella*.

7. The method of claim 1, wherein said probiotic comprises a cultured bacteria of the genus *Prevotella*.

8. The method of claim 1, wherein said pharmaceutical composition comprises cultured *Prevotella* bacteria.

9. The method of claim 1, wherein said determining is by detecting a protein or a small molecule.

* * * * *

SEQUENCE LISTING

```
Sequence total quantity: 2
SEQ ID NO: 1            moltype = DNA  length = 17
FEATURE                 Location/Qualifiers
misc_feature            1..17
                        note = Synthetic
source                  1..17
                        mol_type = other DNA
                        organism = synthetic construct
SEQUENCE: 1
ggcgvacggg tgagtaa                                                    17

SEQ ID NO: 2            moltype = DNA  length = 16
FEATURE                 Location/Qualifiers
misc_feature            1..16
                        note = Synthetic
misc_difference         5..8
                        note = a, c, t, g, unknown or other
source                  1..16
                        mol_type = other DNA
                        organism = synthetic construct
SEQUENCE: 2
ccgcngcngc tggcac                                                     16
```